(12) United States Patent
Yun et al.

(10) Patent No.: US 9,719,947 B2
(45) Date of Patent: Aug. 1, 2017

(54) X-RAY INTERFEROMETRIC IMAGING SYSTEM

(71) Applicant: Sigray, Inc., Concord, CA (US)

(72) Inventors: Wenbing Yun, Walnut Creek, CA (US); Sylvia Jia Yun Lewis, San Francisco, CA (US); Janos Kirz, Berkeley, CA (US)

(73) Assignee: Sigray, Inc., Concord, CA (US)

(*) Notice: Subject to any disclaimer, the term of this patent is extended or adjusted under 35 U.S.C. 154(b) by 60 days.

(21) Appl. No.: 14/700,137

(22) Filed: Apr. 29, 2015

(65) Prior Publication Data
US 2015/0243397 A1    Aug. 27, 2015

Related U.S. Application Data

(63) Continuation-in-part of application No. 14/527,523, filed on Oct. 29, 2014, now abandoned.
(Continued)

(51) Int. Cl.
*G01N 23/02* (2006.01)
*A61B 6/00* (2006.01)
(Continued)

(52) U.S. Cl.
CPC ..... *G01N 23/20075* (2013.01); *A61B 6/4007* (2013.01); *A61B 6/4291* (2013.01);
(Continued)

(58) Field of Classification Search
CPC ..... A61B 6/4007; A61B 6/4291; A61B 6/484; A61B 6/508; G01N 23/20075; G21K 1/02;
(Continued)

(56) References Cited

U.S. PATENT DOCUMENTS

| 2009/0092227 A1* | 4/2009 | David | A61B 6/4233 378/36 |
|---|---|---|---|
| 2012/0041679 A1* | 2/2012 | Stampanoni | A61B 6/00 702/1 |
| 2012/0163554 A1* | 6/2012 | Tada | A61B 6/4035 378/154 |

FOREIGN PATENT DOCUMENTS

JP    2008-200359 A    4/2008

OTHER PUBLICATIONS

Shimura et al., Hard x-ray phase contrast imaging using a tabletop Talbot-Lau interferometer with multiline embedded x-ray targets, Jan. 9, 2013, Optics Letters, vol. 38, No. 2, pp. 157-159.*

(Continued)

*Primary Examiner* — Glen Kao
(74) *Attorney, Agent, or Firm* — Franklin Schellenberg

(57) ABSTRACT

An x-ray interferometric imaging system in which the x-ray source comprises a target having a plurality of structured coherent sub-sources of x-rays embedded in a thermally conducting substrate. The system additionally comprises a beam-splitting grating $G_1$ that establishes a Talbot interference pattern, which may be a π phase-shifting grating, and an x-ray detector to convert two-dimensional x-ray intensities into electronic signals. The system may also comprise a second analyzer grating $G_2$ that may be placed in front of the detector to form additional interference fringes, a means to translate the second grating $G_2$ relative to the detector. The system may additionally comprise an antiscattering grid to reduce signals from scattered x-rays. Various configurations of dark-field and bright-field detectors are also disclosed.

16 Claims, 42 Drawing Sheets

Related U.S. Application Data

(60) Provisional application No. 61/898,019, filed on Oct. 31, 2013, provisional application No. 61/901,361, filed on Nov. 7, 2013, provisional application No. 61/981,098, filed on Apr. 17, 2014, provisional application No. 61/987,106, filed on May 1, 2014, provisional application No. 61/989,743, filed on May 7, 2014, provisional application No. 61/991,889, filed on May 12, 2014, provisional application No. 61/993,811, filed on May 15, 2014.

(51) Int. Cl.
*G21K 1/02* (2006.01)
*G01N 23/20* (2006.01)
*H01J 35/08* (2006.01)

(52) U.S. Cl.
CPC .............. *A61B 6/484* (2013.01); *A61B 6/508* (2013.01); *G21K 1/02* (2013.01); *H01J 35/08* (2013.01); *G21K 2207/005* (2013.01); *H01J 2235/086* (2013.01); *H01J 2235/087* (2013.01)

(58) Field of Classification Search
CPC .......... G21K 2207/005; H01J 2235/086; H01J 2235/087; H01J 35/08
See application file for complete search history.

(56) References Cited

OTHER PUBLICATIONS

Weitkamp et al., Design Aspects of X-ray Grating Interferometry, Conference presentation date Mar. 2012, International Workshop on X-ray and Neutron Phase Imaging with Gratings, AIP Conf. Proc. 1466, pp. 84-89.*

Morimoto et al., "X-ray phase contrast imaging by compact Talbot-Lau interferometer with a signal transmission grating", Jul. 16, 2014, Optics Letters, vol. 39, No. 15, pp. 4297-4300.*

* cited by examiner

X-RAY INTERFEROMETRIC IMAGING SYSTEM

CROSS-REFERENCE TO RELATED APPLICATIONS

This patent application is a continuation-in-part of U.S. patent application Ser. No. 14/527,523, filed Oct. 29, 2014 and entitled "X-RAY INTERFEROMETRIC IMAGING SYSTEM", which claims the benefit of U.S. Provisional Patent Application No. 61/898,019, entitled "X-ray Phase Contrast imaging System" and filed on Oct. 31, 2013; 61/901,361, entitled "An X-ray Source Consisting of an Array of Fine Sub-Sources" and filed on Nov. 7, 2013; and 61/981,098 entitled "Two Dimensional Phase Contrast Imaging Apparatus" and filed Apr. 17, 2014, all of which are incorporated herein by reference in their entirety. The present application additionally claims the benefit of U.S. Provisional Patent Application No. 61/987,106, filed on May 1, 2014 and entitled "METHODS OF REDUCING SCATTER RADIATION USING TALBOT EFFECT"; 61/989,743, filed on May 7, 2014 and entitled "Methods of Improving Detector MTF and DQE and Reducing Scatter Background of an X-ray Imaging System Using Coherence Effect"; 61/991,889, filed May 12, 2014 and entitled "Method of Single-Shot Imaging to Obtain Absorption and Differential Phase, and/or Scattering, and/or Phase Contrast Images"; and 61/993,811, filed May 15, 2014 and entitled "Method of Talbot Effect based X-ray Imaging with High Image Contrast and Design of Apparatus Using Such", all of which are incorporated herein by reference in their entirety.

FIELD OF THE INVENTION

The embodiments of the invention disclosed herein relate to interferometric imaging systems using x-rays, and in particular, interferometric imaging systems comprising high-brightness sources of x-rays for generating phase-contrast images. The high brightness x-ray sources may use anodes or targets comprising periodic microstructures of x-ray generating materials embedded in a thermally conducting substrate of low atomic number material.

BACKGROUND OF THE INVENTION

The initial discovery of x-rays by Röntgen in 1895 [W. C. Röntgen, "Eine Neue Art von Strahlen" (Würzburg Verlag, 1896); "On a New Kind of Rays," Nature, Vol. 53, pp. 274-276 (Jan. 23, 1896)] occurred when Röntgen was experimenting with electron bombardment of targets in vacuum tubes. The contrast between the absorption from bone containing calcium (atomic number Z=20) and soft tissue containing mostly carbon (Z=6), was immediately apparent because the absorption difference between the two materials at x-ray energies between 5 and 30 keV can differ by a factor of 10 or more, as illustrated in FIG. 1. These high energy, short wavelength photons are now routinely used for medical applications and diagnostic evaluations, as well as for security screening, industrial inspection, quality control and failure analysis, and for scientific applications such as crystallography, tomography, x-ray fluorescence analysis and the like.

Although x-ray shadowgraphs have become a standard medical diagnostic tool, there are problems with simple absorption contrast imaging. Notably, for tests such as mammograms, variations in biological tissue may result in only a subtle x-ray absorption image contrast, making unambiguous detection of tumors or anomalous tissue difficult.

In the past decade, a new kind of x-ray imaging methodology has emerged, based on x-ray phase contrast interferometry. The method relies on the well-known Talbot interference effect, originally observed in 1837 [H. F. Talbot, "Facts relating to optical science No. IV", *Philos. Mag.* vol. 9, pp. 401-407, 1836] and fully explained by Lord Rayleigh in 1881 [Lord Rayleigh, "On copying diffraction gratings and some phenomena connected therewith," *Philos. Mag.* vol. 11, pp. 196-205 (1881)].

This effect is illustrated in FIG. 2. For an absorbing grating G of period p, the diffraction pattern from a monochromatic beam of a wavelength $\lambda$ with sufficient coherence forms a repeating interference pattern that reconstructs the original grating pattern, (known as a "self-image") at multiples of a distance known as the Talbot Distance $D_T$. For the case when the incident beam is a plane wave (equivalent to a source located at infinity from the grating G), $D_T$ is given by:

$$D_T = \frac{2p^2}{\lambda} \quad \text{[Eqn. 1]}$$

Between the grating G and the Talbot Distance, other periodic interference patterns emerge as well. The periodicity and the position of the Talbot fringes depend on the transmission properties of the grating G, including amount of phase-shift and percent of absorption, and grating line-to-space (opening) ratio, or duty factor. For example, for a periodic absorption grating, a fringe pattern that reconstructs the original grating pattern with a lateral shift by half the grating period occurs at half the Talbot Distance $D_T/2$, and a fringe pattern with a period of half of the original grating period occurs at one quarter of the Talbot Distance $D_T/4$ and at three quarters of the Talbot Distance $3D_T/4$, as illustrated in FIG. 2. These 2-D interference patterns are sometimes called a "Talbot Carpet" because of the resemblance of these complex patterns to ornate oriental carpets. [Note: this image of an Optical Talbot Carpet in FIG. 2 is adapted from a file created by Ben Goodman and available at commons.wikimedia.org/wiki/File:Optical_Talbot_Carpet.png.]

FIGS. 3 and 4 illustrate a prior art Talbot interferometric comprising a partially coherent source 200 (shown as a microfocus source) of x-rays 288 and a beam splitting grating $G_1$ 210 of period $p_1$ that establishes a set of Talbot interference fringe patterns 289. It should be noted that the coherence length of the x-ray source is preferably set to be comparable to or larger than the period $p_1$ of the beam splitting grating $G_1$ 210, so that the Talbot interference fringes will have high contrast (Talbot fringes may be well defined if the fringe contrast is, for example, greater than 20%). The beam splitting grating 210 may be an amplitude (also known an absorption or transmission) grating, creating intensity fringes as illustrated in FIG. 2, but is more typically a phase grating for efficient use of the illuminating x-rays, introducing periodic phase-shifts to the x-ray pattern that also form periodic Talbot fringes 289. Henceforth in this application, a transmission grating will be used to describe gratings in which the x-ray transmission through the grating lines is less than 10% and a phase grating will be used to describe gratings in which the phase shift through the grating lines is a fraction (e.g. ½) or odd integer multiple of $\pi$.

The Talbot fringes 289 are detected using an x-ray detector 290, preferably with a spatial resolution equal to or better than one third of the Talbot fringe period and having a high x-ray quantum detection efficiency. The detector 290 transforms the x-ray intensity pattern into electronic signals that are transmitted over a connector 291 to an image processing system 295. When an object is placed in the beam path, the image processing system 295 is used to process the x-ray intensity pattern intensity information 298 to obtain absorption, phase, and scattering contrast images.

In practice, the spatial resolution of the detector 290 (such as a flat panel detector, or a charge coupled device (CCD) detector coupled with a scintillator that converts x-rays to visible light) is often on the order of tens of micrometers or larger, and the Talbot fringes 289 may be too fine to detect directly with the detector 290. In this case, an analyzer grating $G_2$ 220 of period $p_2$ is often used to produce Moiré fringes. To record a complete set of images, the analyzer grating $G_2$ 220 will be moved in predetermined distances orthogonal to the grating period and relative to the detector to collect multiple interference patterns in a process called "phase-stepping", or less commonly, rotated at a small angle relative to $G_1$ to obtain a Moiré pattern in a single-shot image for Fourier analysis. The image(s) are then processed to reconstruct the wavefront and determine the shapes, structures, and composition of the objects that created them.

It should also be noted that, instead of physically moving the analyzer grating 220, the position of the x-ray source may also be displaced to create a translation of the interference images that allows the collection of phase-shift information. This can be accomplished electronically by moving the position of the electron beam that bombards the x-ray generating material that serves as the source for the x-rays [see, for example, H. Miao et al., "Motionless phase stepping in X-ray phase contrast imaging with a compact source", *Proceedings of the National Academy of Sciences*, vol. 110(48) pp. 19268-19272, 2013] or by physically moving the x-ray source relative to a fixed position of the analyzer grating 220.

These grating-based x-ray phase-contrast imaging (XPCI) techniques are generally referred to as "grating-based interferometry" (GBI).

As illustrated so far, the grating interferometer only produces interference fringes, and the analysis of these fringes will reveal the structure of the already known grating $G_1$ 210 or the wavefront of the illumination beam. However, when an object is introduced in the path of the x-ray beam, variations in the wavefront introduced by the object result in corresponding changes in the pattern of the Talbot interference fringes, generally known as Moiré fringes. Interferometric image reconstruction techniques may then be used to analyze the wavefront and reconstruct images representing the structure of the unknown object.

In FIG. 5, the prior art Talbot interferometer of FIGS. 3 and 4 is illustrated being used as an imaging technique for a biological sample, in this case, a mouse 240-M, placed between the source 200 and the beam splitting grating $G_1$ 210. The x-rays 288 from the coherent source 200 pass through the mouse 240-M and the beam splitting grating $G_1$ 210 and create a perturbed set of Talbot fringes 289-M. The local phase shifts create angular deviations that translate into changes of locally transmitted intensity when analyzed by the analyzer grating $G_2$ 220 and detector 290. Collecting multiple images from the x-ray detector 290 for situations where the analyzer grating $G_2$ 220 has been displaced by multiple predetermined positions allow a recording of the interference pattern 289-M.

As before, the detector 290 transforms the x-ray intensity pattern into electronic signals that are transmitted over a connector 291 to an image processing system 295 used to produce one or more images 298-M with absorption, differential phase, phase, and scattering contrast information. Numerical processing of the images, including images collected by the system with and without the object under investigation, can be used to infer the shapes and structure of the objects that created them, including objects such as the mouse 240-M. The recorded intensity oscillations can be represented by a Fourier series, and with the proper image processing algorithms, differential phase shift and absorption signals can be extracted, and images corresponding to x-ray absorption, phase contrast, and scattering by the object can be synthesized. [See, for example, A. Momose et al., "Demonstration of x-ray Talbot interferometry", *Jpn. J Appl. Phys*. vol. 42, pp. L866-L868, 2003; A. Momose, U.S. Pat. No. 7,180,979, issued Feb. 20, 2007; and T. Weitkamp et al. "Hard X-ray phase imaging and tomography with a grating interferometer", *Proc. SPIE* vol 5535, pp. 137-142, 2004, and "X-ray phase imaging with a grating interferometer", *Optics Express* vol. 13(16), pp. 6296-6304, 2005.]

It should be noted that other configurations exist in which the object, such as a mouse 240-M, can be placed between the beam splitting grating $G_1$ 210-A and the analyzer grating $G_2$ 220 and detector 290, as illustrated in FIG. 6. Other configurations using various phase and amplitude gratings, or using detector 290 with higher resolution pixels without the analyzer grating 220, may also be known to those skilled in the art.

Aside from imaging the anatomy of mice, clinical applications of phase-contrast x-ray imaging may be found in mammography, where the density of cancerous tissue may have a distinct phase signature from healthy tissue [see, for example, J. Keyriläinen et al., "Phase contrast X-ray imaging of breast", *Acta Radiologica* vol. 51 (8) pp. 866-884, 2010], or for bone diseases like osteoporosis or osteoarthritis, in which the angular orientation of the bone structures may be an early indicator of bone disease [see, for example, P. Coan et al., "In vivo x-ray phase contrast analyzer-based imaging for longitudinal osteoarthritis studies in guinea pigs", *Phys. Med. Biol*. vol. 55(24), pp. 7649-62, 2010].

However, for the prior art configurations described so far, x-ray power is a problem. An x-ray source with a full-width half maximum diameter S given by $$S \leq \frac{\lambda L}{2\pi p_1} \quad \text{[Eqn. 2]}$$

where $p_1$ is the period of the beam splitting grating $G_1$ 210 and L the distance between the source 200 and the beam splitting grating $G_1$ 210, is required for the technique to produce high contrast fringes and Moiré patterns. For practical applications and system geometries, this implies a microfocus source. However, electron bombardment of the target also causes heating, and the x-ray power that can be achieved is limited by the maximum total electron power that can fall on the microspot without melting the x-ray generating material. A limited electron power means a limited x-ray power, and the low x-ray flux achievable with typical x-ray targets may lead to unacceptable long exposure times when used, for example, for mammography or other diagnostic tests involving live patients or animals. The total x-ray flux can be increased by distributing higher electron power over a larger area, but then the source becomes less coherent, degrading the image contrast.

Coherent x-rays of higher brightness and sufficient flux can be achieved by using a synchrotron or free-electron laser x-ray source, but these machines may occupy facilities that cover acres of land, and are impractical for use in clinical environments.

One innovation that has been shown to enable greater x-ray power employs an additional grating $G_0$ [see, for example, John F. Clauser, U.S. Pat. No. 5,812,629, issued Sep. 22, 1998]. Such a system is illustrated in FIG. 7. In this configuration, a source grating $G_0$ 308 with period $p_0$, which is typically an x-ray transmission grating, is used in front of an x-ray source 300. In this case, the x-ray source may be a high-power extended source with a large incident electron beam area (and not a microfocus source) that produces a higher total flux of x-rays.

The x-rays 388 pass through the grating $G_0$ 308 and emerge from the grating apertures as an array of individually spatially coherent (similar to a microfocus source described above) but mutually incoherent sub-sources of illumination for the beam splitting grating $G_1$. To ensure that each x-ray sub-source in $G_0$ contributes constructively to the image-formation process, the geometry of the setup should satisfy the condition:

$$p_0 = p_2 \frac{L}{D} \qquad [\text{Eqn. 3}]$$

When the condition is met, the x-rays from the many apertures of $G_0$ produce the same (overlapping) Talbot interference pattern, and because the various mutually incoherent sources do not interfere with each other, these Talbot patterns will add as intensities. The effect at the detector 290 is therefore to simply increasing the signal (along with it the signal-to-noise ratio) over what a single coherent source can provide.

This configuration is called the Talbot-Lau interferometer [see Franz Pfeiffer et al., "Phase retrieval and differential phase-contrast imaging with low-brilliance X-ray sources", *Nature Physics* vol. 2, pp. 258-261, 2006; and also Described in U.S. Pat. No. 7,889,838 by Christian David, Franz Pfeiffer and Timm Weitkamp, issued Feb. 15, 2011].

FIGS. 8A-8C illustrate x-ray images of a live mouse collected using a Talbot-Lau interferometer, as reported by Martin Bech [M. Bech et al., "In-vivo dark-field and phase-contrast x-ray imaging", *Scientific Reports* 3, Article number: 3209, 2013, FIG. 1]. The x-ray energy used was 31 keV, and the gratings were fabricated by lithographically etching structures in silicon (Z=14). Absorption gratings $G_0$ for the source and $G_2$ for the analyzer were created by additionally coating the patterned silicon with gold (Z=79).

All of the images of FIGS. 8A-8C were reported as reconstructed from the same set of 5 interferometric images, each collected over an exposure time of 10 seconds. The raw images were Fourier processed and ramp corrected to obtain the three image modalities. FIG. 8A illustrates an intensity image based on x-ray attenuation, showing the absorption contrast between the bones and soft tissue. FIG. 8B illustrates a phase-contrast image, which clearly identifies soft tissue structures such as the trachea (illustrated with an arrow). FIG. 8C illustrates an additional dark-field contrast image due to x-ray scattering from fine features with linear dimensions less than the spatial resolution of the imaging system, which strongly highlights the fur and lungs.

Unfortunately, the current art of Talbot-Lau GBIs have many constraints for most practical applications such as clinical imaging, including a requirement that both the source grating $G_0$ and the analyzer grating $G_2$ have fine pitches and apertures with large aspect ratios.

The requirement for the source grating $G_0$ is to create fine individual well-separated x-ray sub-sources to minimize the reduction in image contrast due to unwanted transmission of x-rays through the aperture defining structures. However, for a 1:1 line-to-space ratio grating, simple x-ray shadowing dictates that the x-ray transmission through the grating is limited to less than 50%, and is reduced further when the angular shadowing (limiting the angular range of the x-rays from the source to reach the object) is included. Furthermore, the optimal line-to-space ratio for $G_0$ that reduces the radiation dose to the object (which is important to preclinical and clinical imaging applications) is closer to 3:1 rather than 1:1. In this case, about 75% of the x-rays from the source are blocked due to area shadowing alone, and when gratings with large aspect ratios are used, greater losses occur due to angular shadowing.

The requirement for the analyzer grating $G_2$ is to be able to sample the Talbot interference fringes with sufficient resolution without losing contrast. As a result, both the $G_0$ and $G_2$ gratings must have small apertures and be of thickness sufficient to minimize unwanted x-ray transmission, which limits the efficient use of the x-rays from the source. Furthermore, the loss from the analyzer grating $G_2$ further results in a significantly higher dose (relative to the same system without a $G_2$ grating) for the object under investigation to produce an image with good characteristics due to multiple exposures for phase-stepping and absorption of x-rays resulting in lower signal-to-noise. When the object under investigation is a live animal or human, higher doses of ionizing radiation are undesirable and generally discouraged.

If the aperture dimensions of the grating $G_0$ are larger, angular collimation can be reduced (although not the area shadowing) so that x-ray transmission is not reduced as severely, but this reduces the spatial coherence length of the x-ray beam downstream from the apertures, and leads a reduction in image contrast. Smaller apertures can increase the possible image contrast and resolution by improving spatial coherence, but decreases the overall number of x-rays in the system, thus requiring longer exposure times. Moreover, with smaller apertures, these fine gratings become more difficult to manufacture.

The problem is exacerbated when attempting to use a Talbot-Lau interferometer for higher energy x-rays, which are often desired to obtain sufficient transmission through an object and to reduce radiation dose. In general, as was illustrated in FIG. 1, the absorption of x-rays for biological tissue is far lower for x-rays with energy greater than 5 keV, and the use of higher energy x-rays will reduce the absorbed dose of potentially harmful ionizing radiation by orders of magnitude. However, 5 keV photons have a wavelength of 0.248 nm, and 50 keV have a wavelength 10 times smaller (0.0248 nm). Furthermore, building absorbing gratings such as $G_0$ and $G_2$ for these higher-energy, shorter-wavelength x-rays can present difficulties, as the thickness of the gratings must increase exponentially to maintain the same absorption factor for higher energy x-rays (the x-ray attenuation length is approximately proportional to $E_{kev}^3$).

The preceding problems of Talbot-Lau GBIs using linear gratings, which can be used for collecting interference data in one dimension only, become more severe if one wishes to generate phase-contrast images in two orthogonal directions.

This is often required to make the image reconstruction robust and images more understandable, and because features parallel to the grating lines in the 1-D case are typically less accurately measured. One simple approach is to perform XPCI in two orthogonal directions and then subsequently register the two datasets properly. In addition to challenges associated with the imaging and registration processes, this approach may not be practical, especially when used with living subjects who may move or simply become impatient, and who will incur increased dosage (doubled) if the phase stepping must be performed in two directions. Simultaneous two-dimensional XPCI would be desirable, especially if data collection in a single exposure (shot) and at high x-ray energies is possible to reduce exposure times and the absorbed dosage.

There is therefore a need for an x-ray interferometric imaging system that offers the resolution and detection capabilities of the Talbot-Lau interferometer, but employing a brighter compact source of x-rays and, ideally, a brighter source of higher energy x-rays, especially one that could provide simultaneous two-dimensional phase-contrast imaging.

BRIEF SUMMARY OF THE INVENTION

We disclose here an x-ray interferometric imaging system in which the x-ray source comprises a target having a plurality of micro structured x-ray generating materials arranged within a periodic array pattern to form periodic sub-sources of x-rays. The system additionally comprises a beam-splitting grating $G_1$ that creates a Talbot interference pattern, and an x-ray detector to convert two-dimensional x-ray intensities into electronic signals.

If the spatial resolution of the detector is equal to or better than one third of the Talbot fringe period, the detector may record the fringes directly. The system may also comprise a second analyzer grating $G_2$ that may be placed in front of the detector to form additional interference fringes, and a means to translate the analyzer grating $G_2$ relative to the detector to create Moiré fringes at the detector. Additionally, the system may comprise a means of translating the phase grating $G_1$ relative to the analyzer grating $G_2$.

The x-ray source target comprises a plurality of microstructures of x-ray generating materials (such as molybdenum or tungsten) in close thermal contact with a thermally conducting substrate of a low atomic number material, such as diamond or beryllium. The x-ray generating microstructures may be arranged in a periodic pattern, with each periodic element of the pattern corresponding to a single discrete microstructure or alternatively, with each periodic element of the pattern comprising multiple discrete microstructures. One or more sources of electrons bombard the plurality of x-ray generating materials, which are generally arranged within a periodic array, so that the x-ray generated from each periodic array element serves as an individually coherent sub-source of x-rays of illumination for the beam splitting grating $G_1$. In some embodiments, the microstructures have lateral dimensions measured on the order of microns, and with a thickness on the order of one half of the electron penetration depth within the substrate material. In some embodiments, the microstructures are formed in a regular two-dimensional array.

The beam splitting grating $G_1$ may be a phase grating or an absorption grating. The analyzer grating $G_2$ is generally a transmission grating. Both gratings $G_1$ and $G_2$ may be fabricated as lithographically produced microstructures in silicon, and may comprise 1-D structures, 2-D structures, or combinations thereof.

A particular advantage of the invention is that high x-ray brightness and large x-ray power may be achieved by using an x-ray target in which the microstructures of a high Z material are in close thermal contact with, or embedded in, a substrate of low Z material and high thermal conductivity, such as beryllium or diamond. The ability of the substrate to draw heat away from the x-ray generating material allows higher electron density and power to be used, generating greater x-ray brightness and power from each of the sub-sources. This results in the creation of individual, well-separated spatially coherent x-ray sub-sources from the high Z material, while the use of a substrate with low Z and low mass density minimizes the production of x-rays from the substrate that can lead to a reduction in image contrast.

Figure 1:
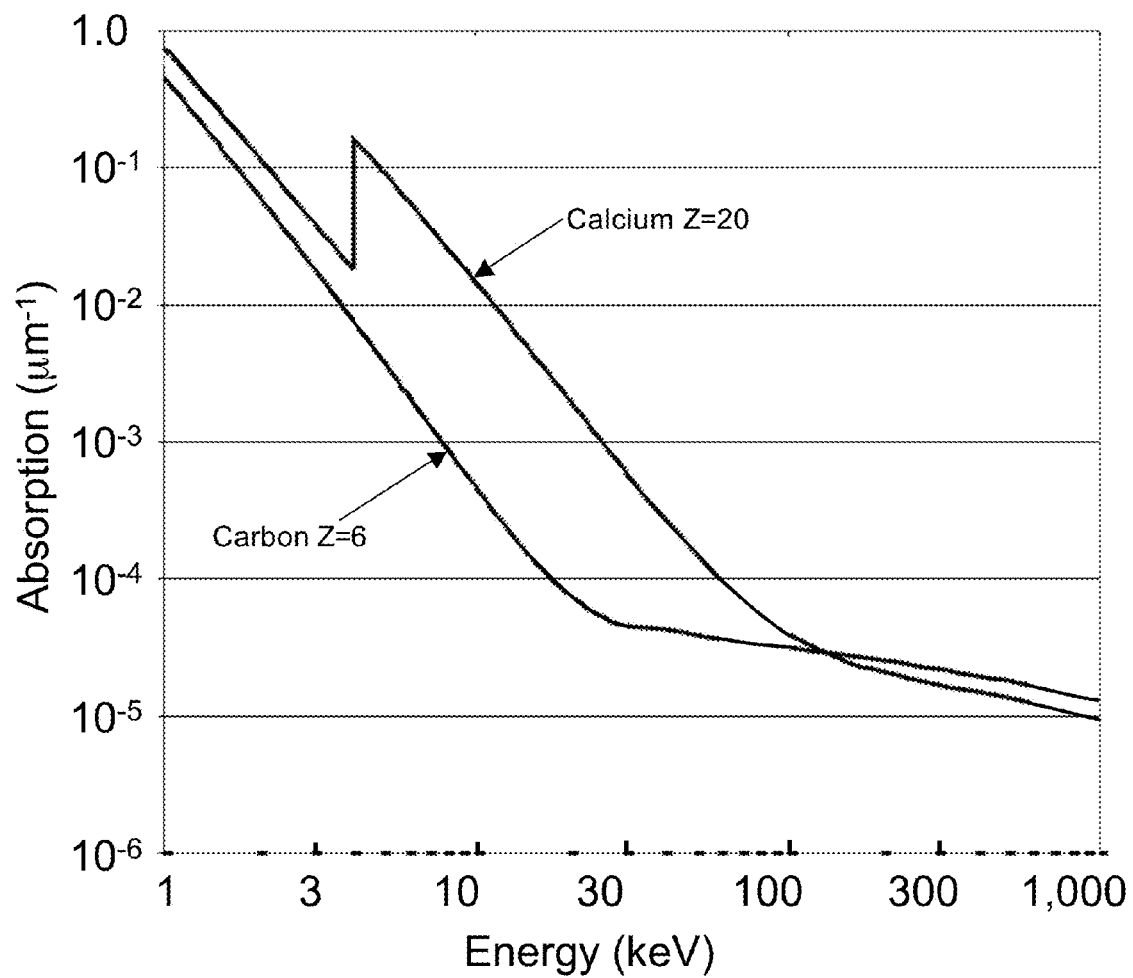
FIG. 1 illustrates a plot of the x-ray absorption of carbon and calcium as a function of x-ray energy.
Figure 2:
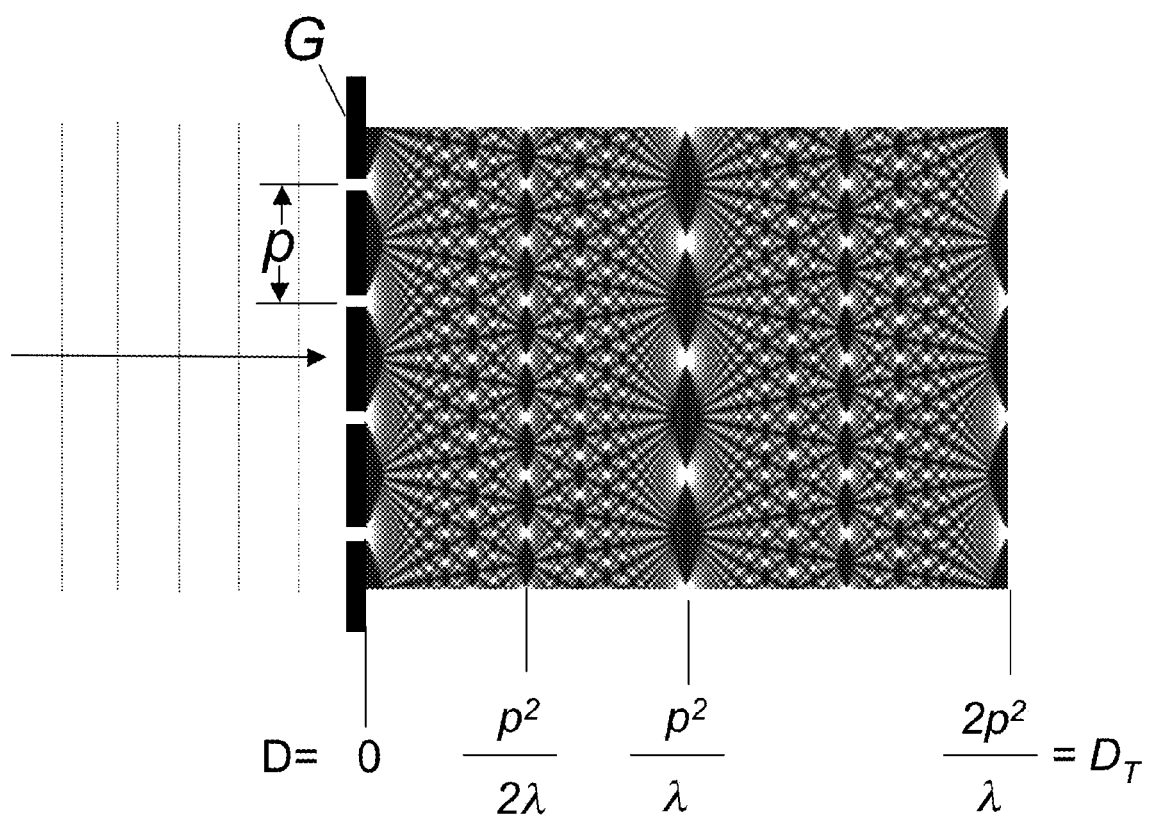
FIG. 2 illustrates a prior art Talbot interference pattern produced by a transmission grating.
Figure 3:
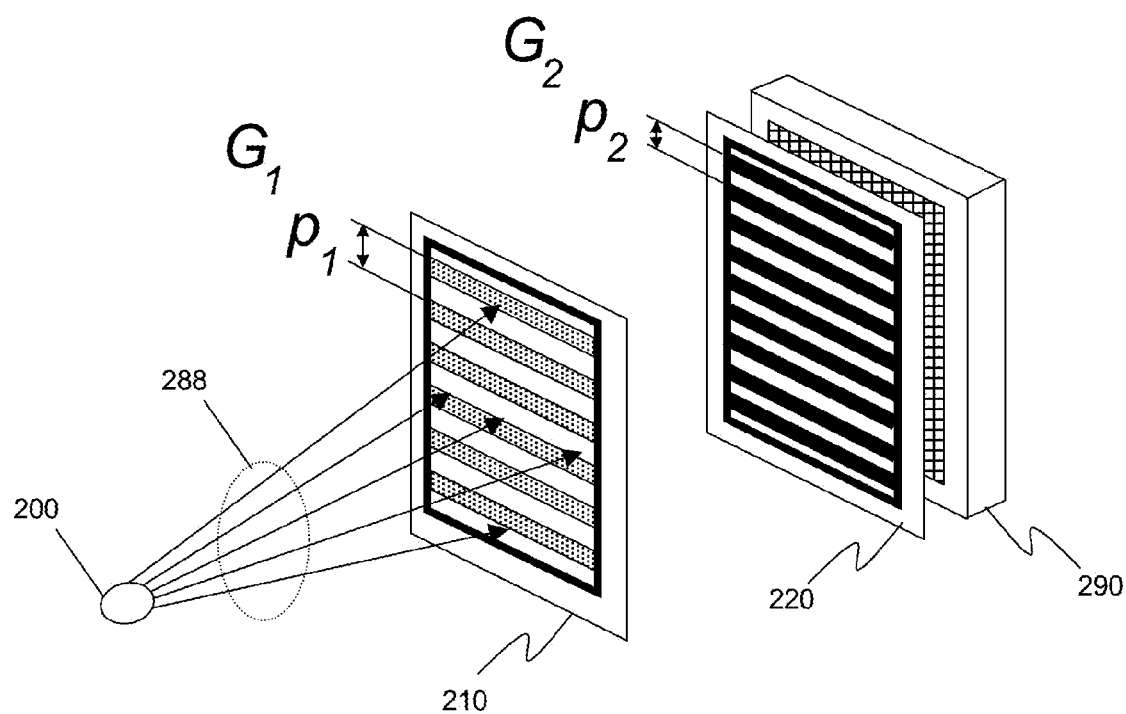
FIG. 3 illustrates a prior art x-ray grating interference system using a microfocus source.
Figure 4:
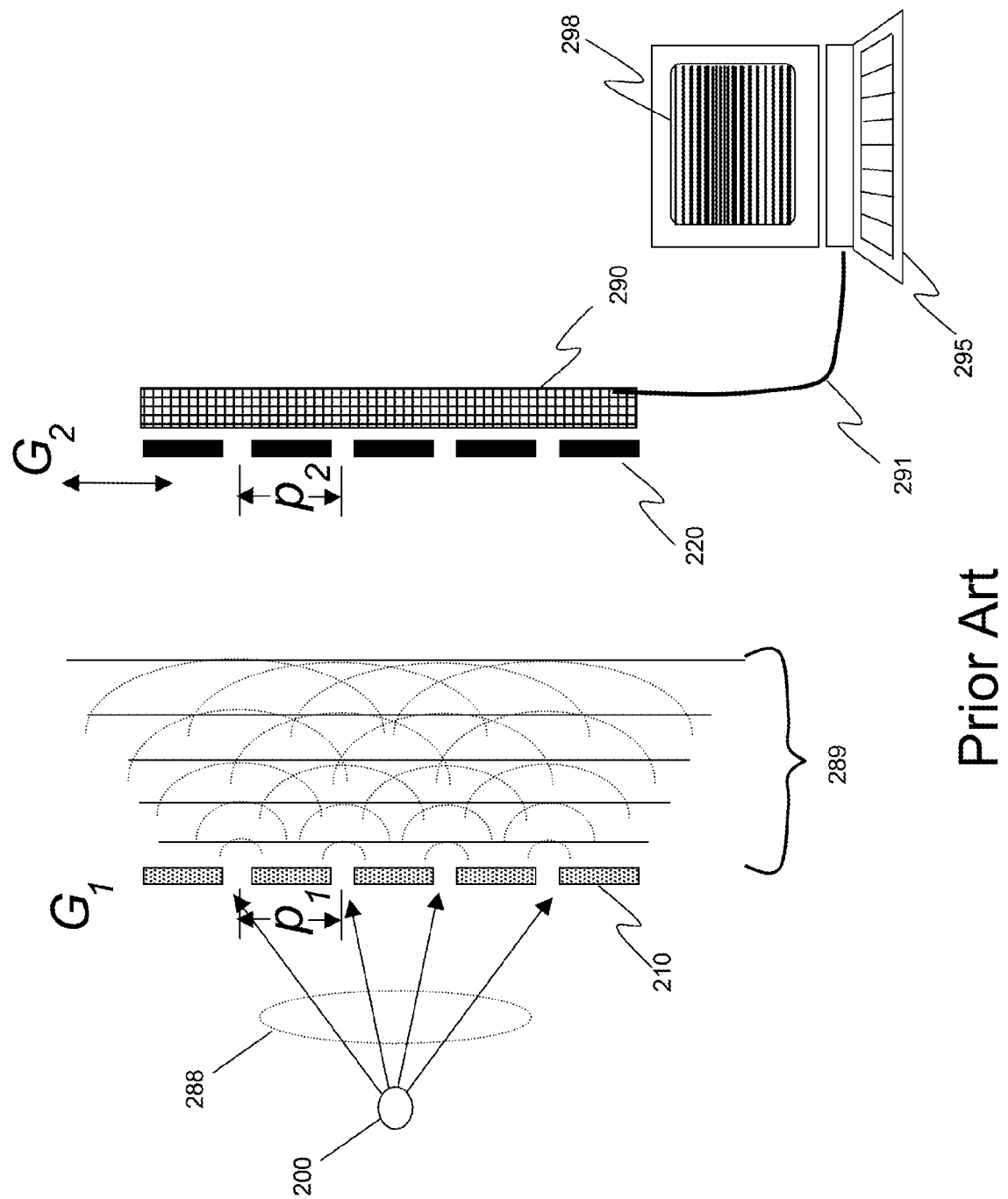
FIG. 4 illustrates a cross section view of the prior art x-ray grating interference system of FIG. 3.
Figure 5:
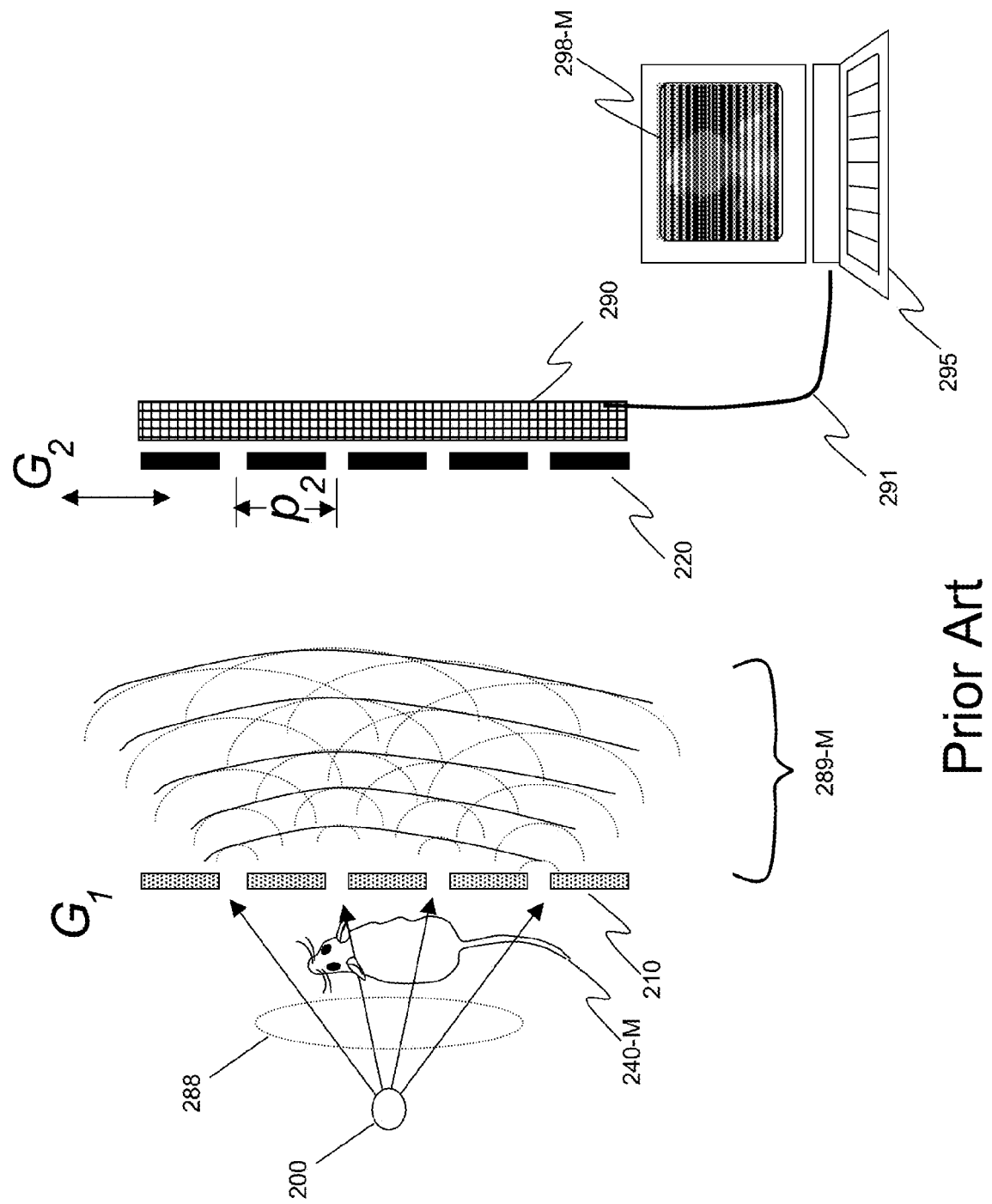
FIG. 5 illustrates the prior art x-ray grating interference system of FIG. 3 used to form an x-ray contrast image of a mouse.
Figure 6:
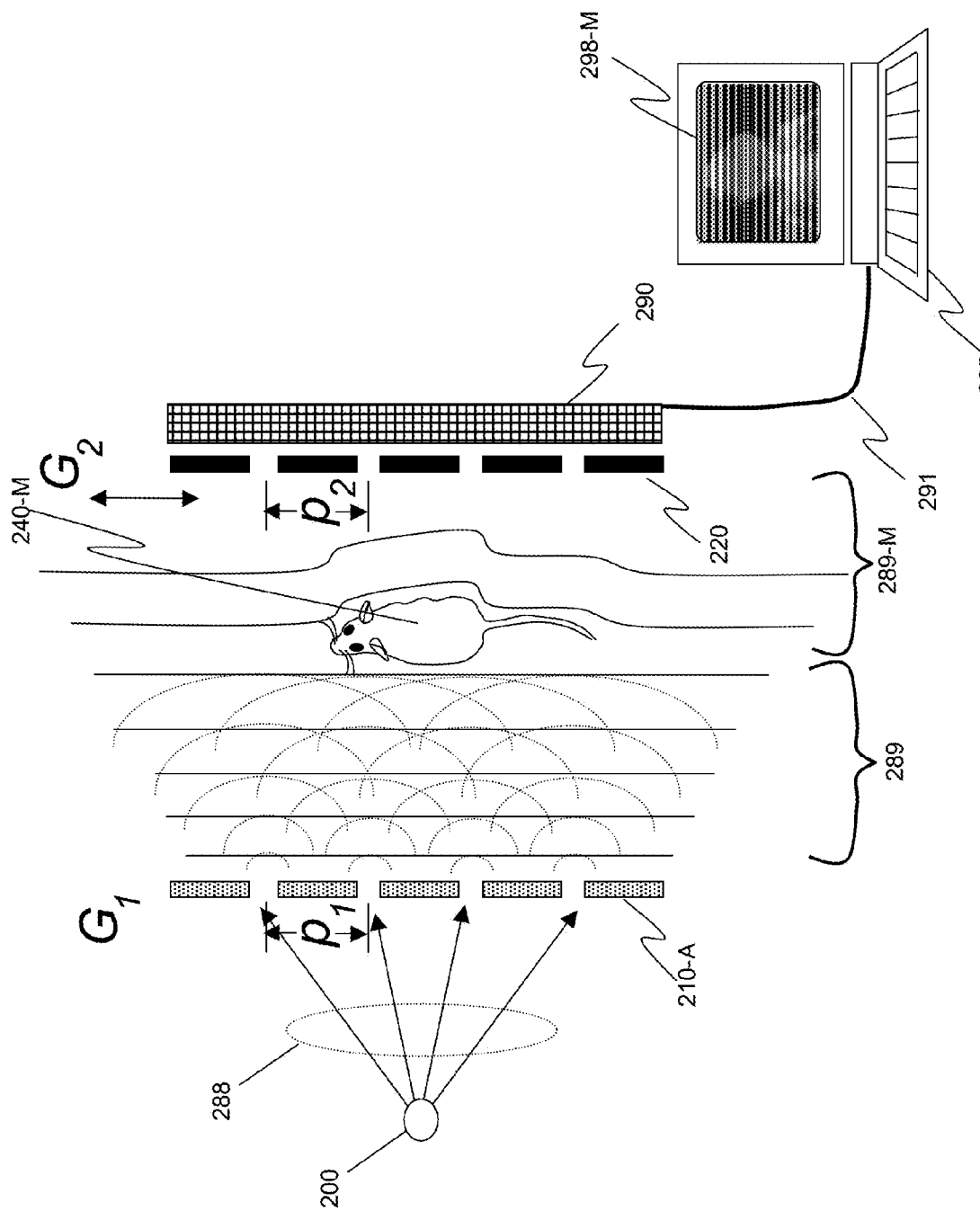
FIG. 6 illustrates a variation of the prior art x-ray grating interference system of FIG. 3 used to form an x-ray contrast image of a mouse.
Figure 7:
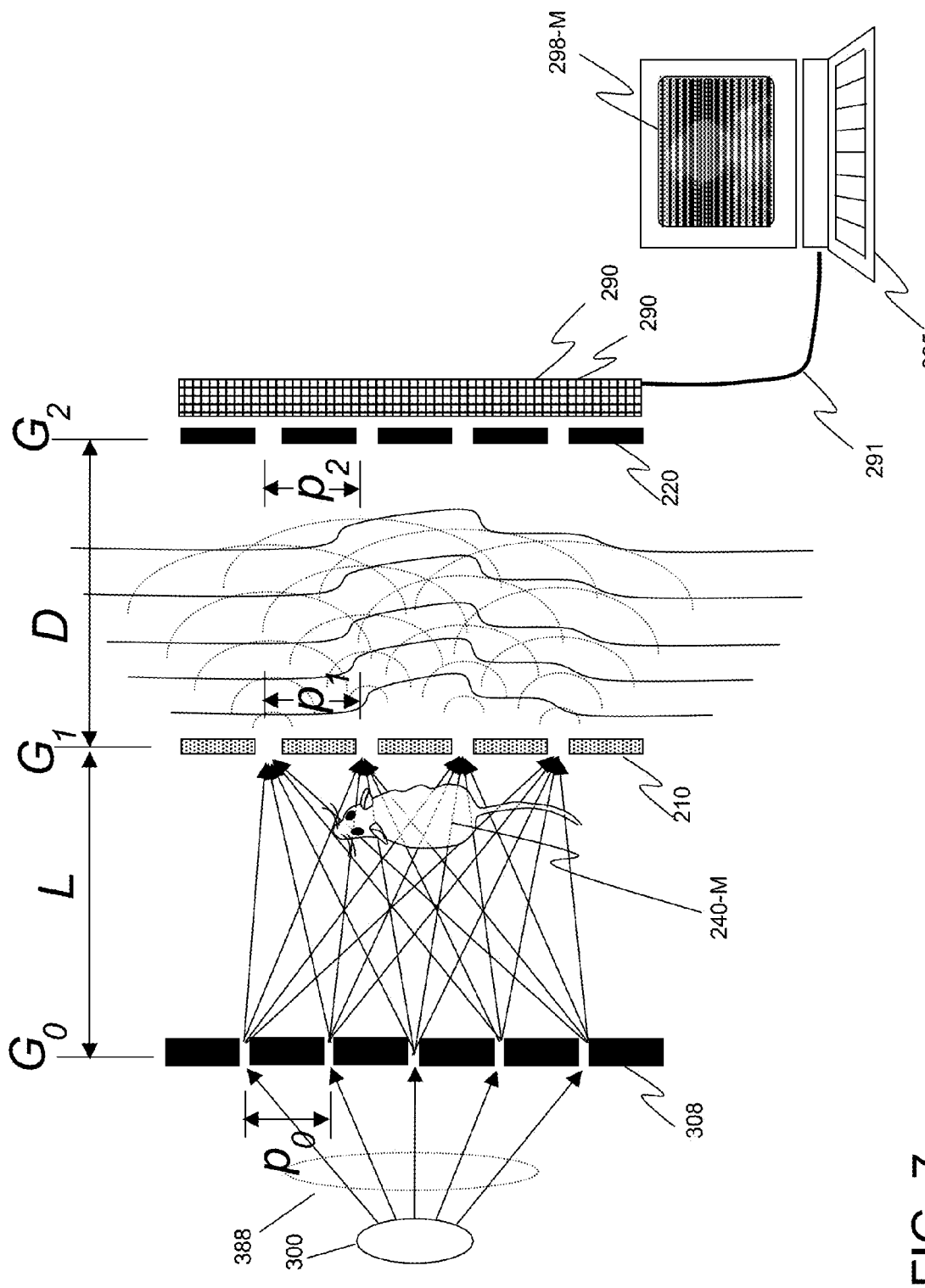
FIG. 7 illustrates a prior art Talbot-Lau interferometer being used to form an x-ray contrast image of a mouse.
Figures 8A, 8B, 8C:
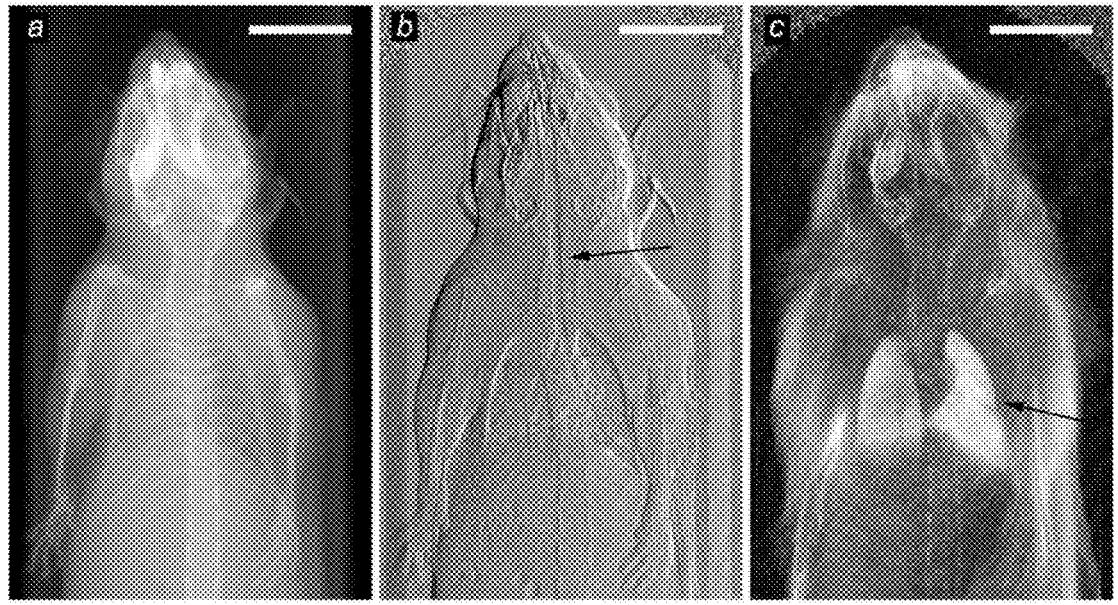
FIG. 8A illustrates a published x-ray absorption image of a mouse gathered using a prior art Talbot-Lau interference system.
FIG. 8B illustrates a published x-ray phase-contrast image of a mouse gathered using a prior art Talbot-Lau interference system.
FIG. 8C illustrates a published x-ray dark field scattering image of a mouse gathered using a prior art Talbot-Lau interference system.

Note: The illustrations in the Drawings disclosed in this application are typically not shown to scale, and are meant to illustrate the principle of the invention and its function only, and not specific relationships between the microstructures in the target and the various grating periods $p_1$, $p_2$, $p_3$, $p_4$, $p_5$, and $p_6$. Please refer to the descriptions in the text of the Specification for specific details of the dimensions of these objects.

DETAILED DESCRIPTIONS OF EMBODIMENTS OF THE INVENTION

Descriptions of Various Embodiments of the Invention

Figure 9:
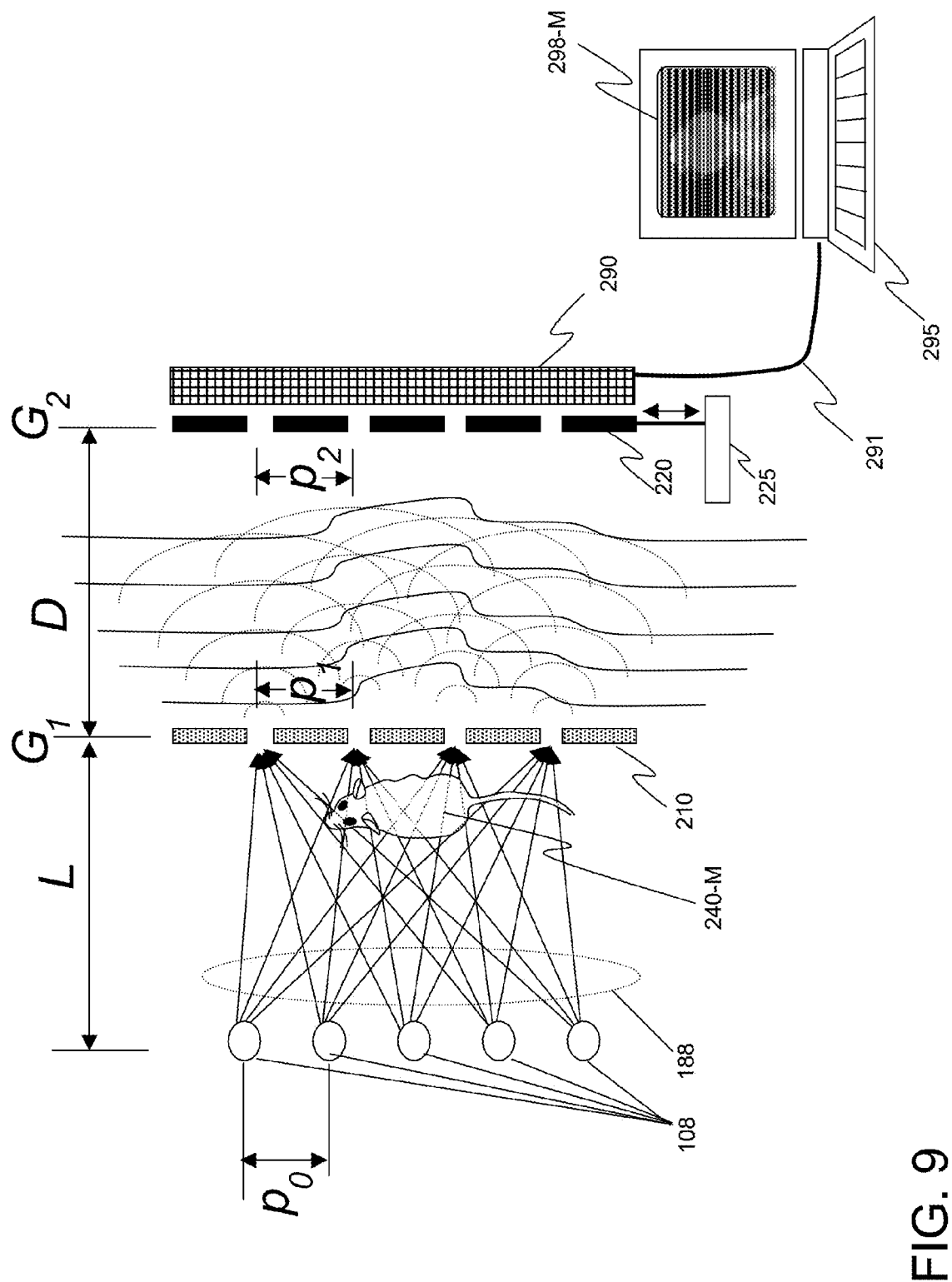
FIG. 9 illustrates a schematic cross-section view of an embodiment of an x-ray interferometric imaging system according to the invention.

One embodiment of the invention disclosed herein is an x-ray phase-contrast imaging (XPCI) system as illustrated in FIG. 9. The system bears some similarity to the prior art Talbot-Lau interferometer, in that it comprises a beam splitting grating $G_1$ 210 of period $p_1$ that establishes a Talbot interference pattern, and an x-ray detector 290 typically comprising an array of sensors to convert two-dimensional x-ray intensities into electronic signals.

The beam splitting grating $G_1$ 210 may be a phase grating or a transmission grating, and may comprise 1-D periodic patterns (linear gratings), or may comprise more complex 2-D structures such as a grid that is periodic in two orthogonal directions.

The system may also comprise an analyzer grating $G_2$ 220 of period $p_2$ that may be placed in front of the detector to form additional interference fringes, such as Moiré fringes. The system may additionally comprise a means 225 to translate the analyzer grating $G_2$ 220 relative to the detector, and a connector 291 to transmit electronic signals corresponding to the detected x-ray intensity to an image processing system 295 for processing.

However, instead of using an extended x-ray source and an additional grating $G_0$ to create a plurality of x-ray source spots, as was done in the Talbot-Lau system, the embodiments of the present invention use an x-ray source comprising a plurality of x-ray generating sub-sources 108 arranged in a periodic array that generate x-rays 188 from electron beam bombardment, such that each sub-source is individually coherent, but together function as a set of mutually incoherent or partially coherent sub-sources of illumination for the beam splitting grating $G_1$. As with the combination of the extended x-ray source and the source grating of the Talbot-Lau interferometer, these sub-sources 108 form the Talbot interference fringe patterns that are created by the beam splitting grating $G_1$ 210 and perturbed by an object 240-M, and may be recorded by detector 290. If the spatial resolution of the detector 290 has a spatial resolution equal to or better than one third of the Talbot fringe period, the detector may record the fringes directly. If a lower resolution detector is used, an analyzer grating $G_2$ 220 may also be used to create Moiré fringes, as was described for the Talbot-Lau interferometer.

The plurality of discrete x-ray sub-sources can be considerably brighter than the x-ray source of the Talbot-Lau system. Because the source comprises sub-sources that are self-coherent but may be mutually incoherent, there is no need for an attenuating transmission grating $G_0$ to create an array of sub-sources from an extended x-ray source.

A system according to the invention comprising multiple sub-sources in a structured target may be designated a Talbot-ST interferometer.

Figure 10:
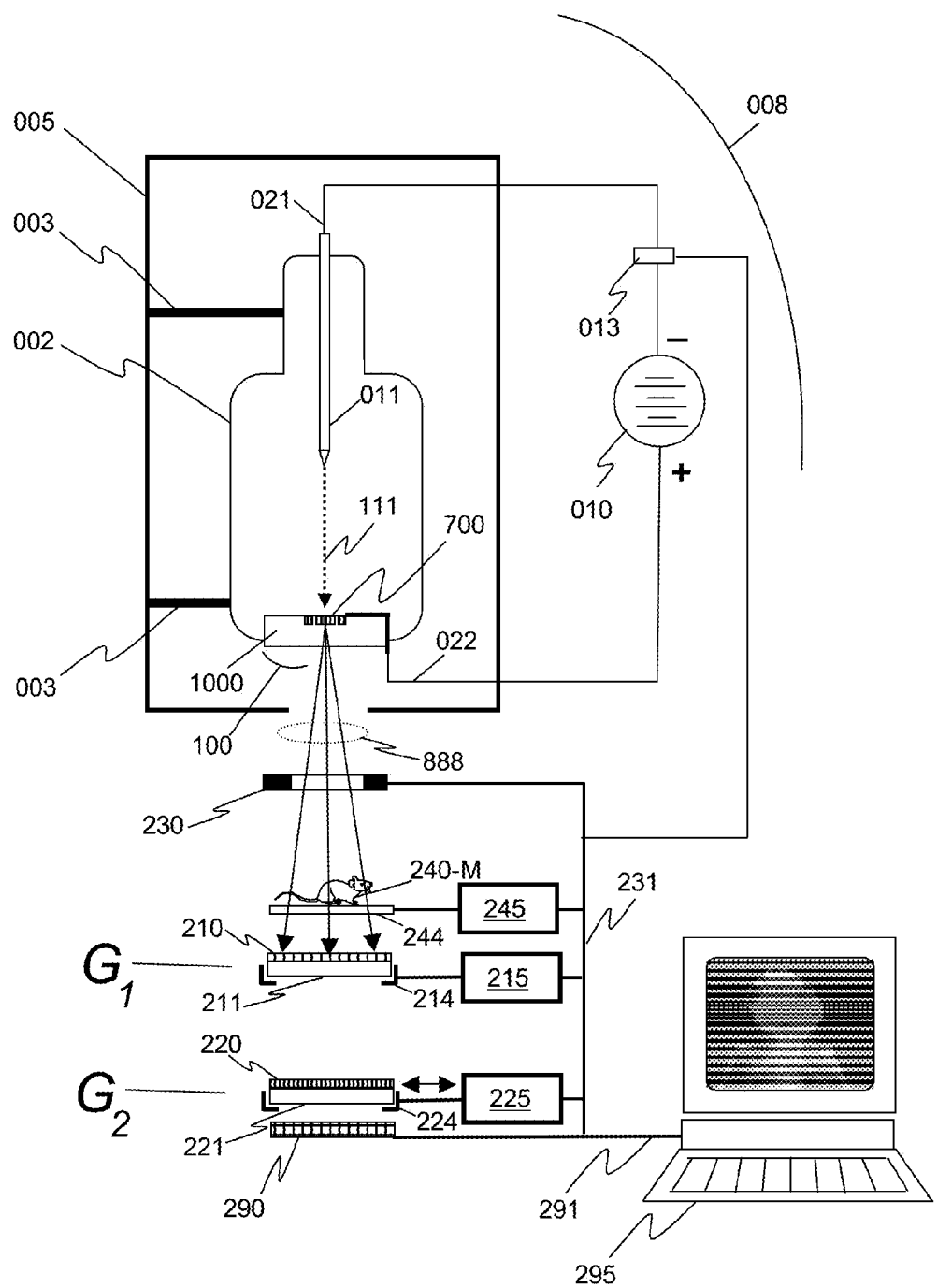
FIG. 10 illustrates a schematic cross-section view of an embodiment of the invention.
Figure 11:
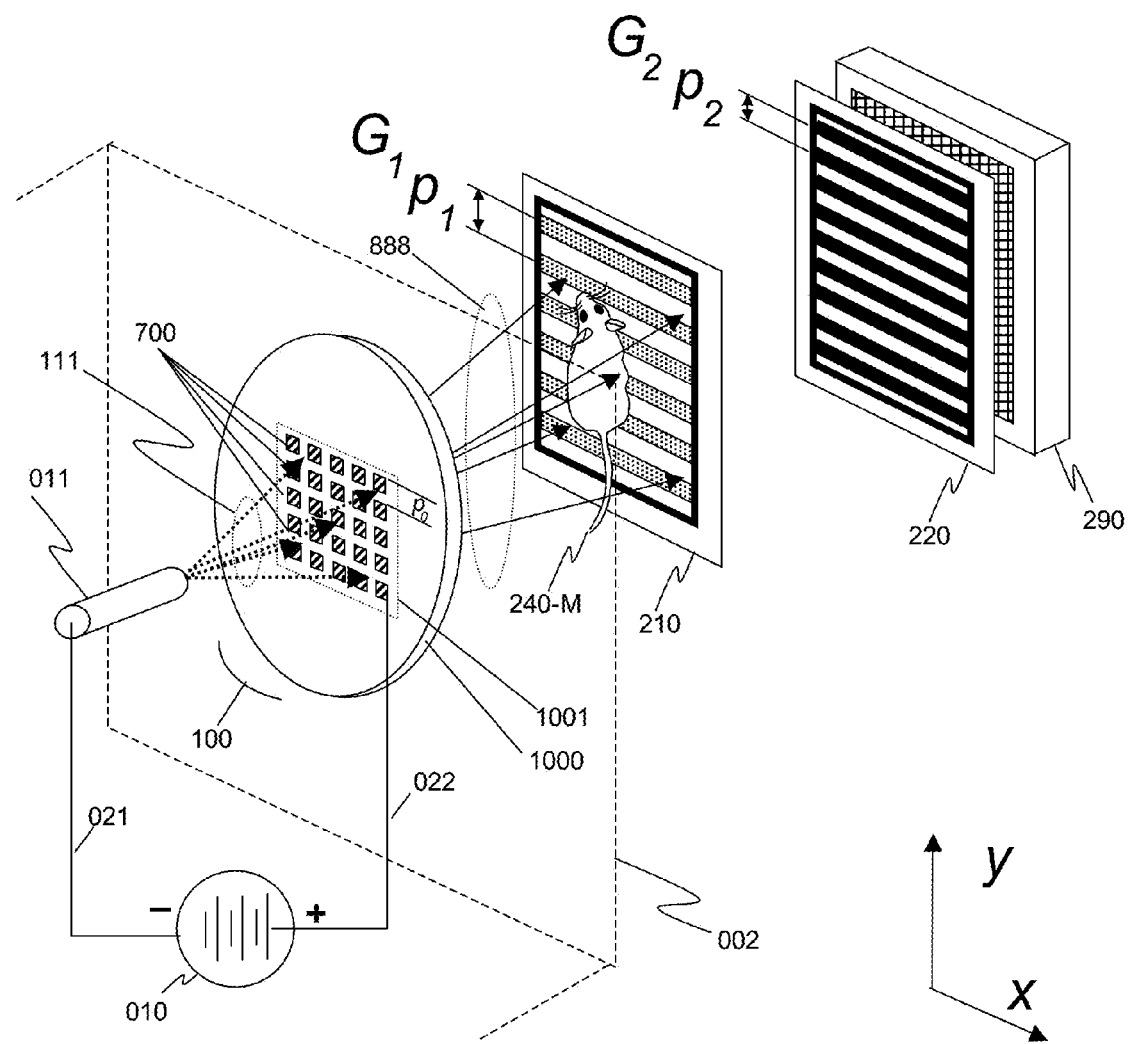
FIG. 11 illustrates a perspective view of the embodiment of the invention shown in FIG. 10, in which the x-ray target comprises two dimensional periodic array of x-ray generating microstructures.
Figure 12:
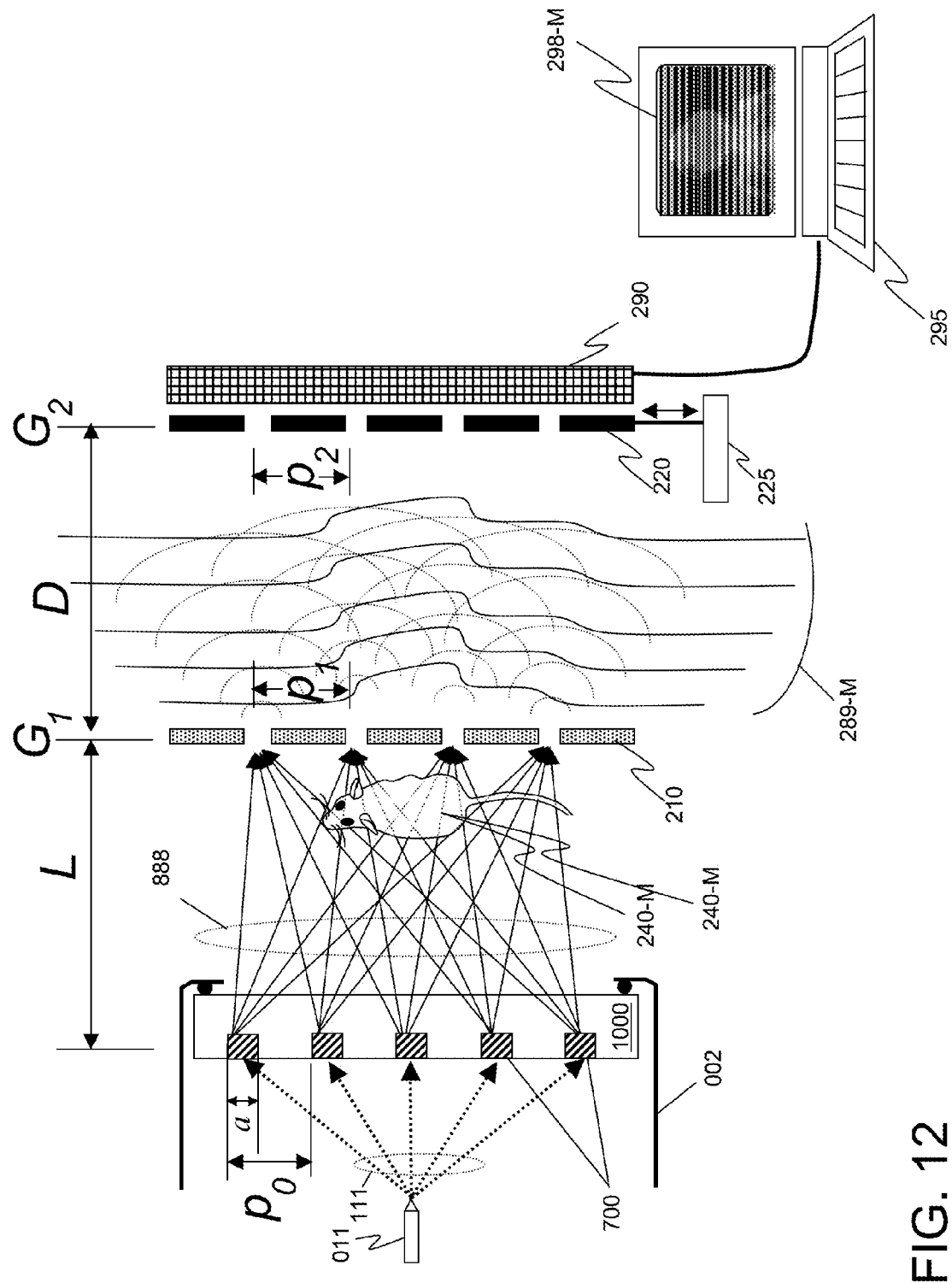
FIG. 12 illustrates a detailed schematic cross-section view of the embodiment of the invention shown in FIGS. 10 and 11.

FIGS. 10, 11 and 12 show a more detailed illustration of one embodiment of the invention, in which the array of sub-sources are formed using microstructures of x-ray generating material embedded in a thermally conducting substrate. In this embodiment, an x-ray source 008 illuminates an object 240-M and a beam-splitting grating $G_1$ 210, and the interference pattern they form is detected by a detector 290.

For the x-ray source 008, a high voltage power supply 010 provides electrons through a lead 021 to an electron emitter 011 in a vacuum chamber 002 held to a shielding housing 005 by supports 003. The electron emitter 011 emits electrons 111 towards a target 100. The target 100 comprises a substrate 1000 and a region that comprises a periodic array of discrete microstructures 700 comprising x-ray generating material (typically a high Z metallic material such as copper, molybdenum or tungsten) positioned on or embedded or buried in the substrate (typically a low Z material such as beryllium, diamond, silicon carbide). The discrete microstructures 700 may be any number of sizes or shapes, but are generally designed to be periodic arrays of right rectangular prisms with lateral dimensions on the order of microns in size in at least one dimension, such that the emission from each microstructure acts as a sub-source of x-rays with a spatial coherence length that is comparable to or larger than the grating period $p_1$ at the beam splitting grating $G_1$ 210. Additionally, the microstructures are preferably of a thickness (as typically measured orthogonal to the target surface) that is on the order of one half of the electron penetration depth within the substrate material.

The period $p_0$ of the microstructures 700 that form the x-ray sub-sources is related to the other geometric parameters in the system by:

$$p_0 = p_2 \frac{L}{D} \qquad \text{[Eqn. 4]}$$

where L is the distance from the x-ray sub-sources 700 to the grating $G_1$ 210, and D is the distance from the grating $G_1$ to the detector/analyzer grating $G_2$ 220 with period $p_2$. In some embodiments, D will be set to be one of the fractional Talbot distances with interference fringes of high contrast (visibility), defined by:

$$\text{Contrast} = \frac{I_{max} - I_{min}}{I_{max} + I_{min}} \qquad \text{[Eqn. 5]}$$

where $I_{max}$ and $I_{min}$ is the intensity peak and valley of the Talbot interference fringes without an object in the beam path, respectively.

For plane wave illumination (i.e. equivalent to the x-ray source being located at infinity) of a beam-splitting grating with a $\pi$ phase-shift, the distance D is preferably given by:

$$D = D_N = N \frac{p_1^2}{8\lambda} = \frac{N}{16} D_T \qquad \text{[Eqn. 6]}$$

where $D_N$ is the fractional Talbot distance for a plane wave illumination, $\lambda$ is the mean x-ray wavelength, and N is referred to as a Talbot fractional order. The preferred value of D is dependent on the attenuating or phase shifting properties of the beam-splitting grating $G_1$, the line-space ratio of the beam-splitting grating $G_1$, and the source-to-grating distance L. For a $\pi$ phase-shifting grating with a line-to-space ratio of 1:1, an odd integer fractional Talbot order N (N=1, 3, 5 . . . ) is preferred for determining the distance D. For an x-ray source located at a finite distance (e.g. L not infinity), D is increased to:

$$D = \frac{L \times D_N}{L - D_N} \qquad \text{[Eqn. 7]}$$

The Talbot fringe period $p_f$ for a given fractional order is given by:

$$p_f = K p_1 \frac{L+D}{L} \qquad \text{[Eqn. 8]}$$

where K is a parameter dependent on the attenuating or phase shifting properties of the beam-splitting grating $G_1$. K equals ½ when the beam-splitting grating is a π phase-shift grating, and equals 1 when the beam splitting grating is a π/2 phase shift grating.

Likewise, the Talbot fringe contrast is improved if a smaller x-ray sub-source size (i.e. more spatially coherent x-rays) is used, and in which the pitch $p_1$ used for the beam splitting grating $G_1$ is related to the size of the sub-source a and the distance L between them, satisfying the following requirement:

$$p_1 < \frac{\lambda L}{a} \qquad [\text{Eqn. 9}]$$

where λ is a predetermined x-ray wavelength that will generally correspond to the wavelength of the monochromatic x-rays produced by the corresponding sub-source, or the mean x-ray wavelength for an x-ray sub-source with a broader spectrum.

In the vacuum chamber 002, electrons 111 bombard the target, and generate heat and x-rays 888 in the microstructures 700. The material in the substrate 1000 is selected such that it has relatively low energy deposition rate for electrons in comparison to the microstructures of the x-ray generating material, typically by selecting a low Z material for the substrate, and therefore will not generate a significant amount of heat and x-rays. The substrate 1000 material may also be chosen to have a high thermal conductivity, typically larger than 100 W/(m ° C.). The microstructures of the x-ray generating material are also typically embedded within the substrate, i.e. if the microstructures are shaped as rectangular prisms, it is preferred that at least five of the six sides are in close thermal contact with the substrate 1000, so that heat generated in the microstructures 700 is effectively conducted away into the substrate 1000. However, targets used in other embodiments may have fewer direct contact surfaces. In general, when the term "embedded" is used in this disclosure, at least half of the surface area of the microstructure will be in close thermal contact with the substrate.

The microstructures are typically connected electrically with a lead 022 to the positive terminal of the high voltage source 010 to allow the target to serve as an anode in the electrical system. Alternatively, the target may be grounded while the cathode (electron emitter) is of negative charge, or the target may be connected to a positive terminal while the cathode is grounded, so long as the anode is of relative higher voltage than the cathode. Additionally, in some embodiments, electron optics such as electrostatic lenses or magnetic coils may be placed inside or outside of the vacuum chamber 002 around or near the path of electrons 111 to further direct and focus the electron beam.

The target 100 as illustrated may additionally serve as a window in the vacuum chamber 002 so that the x-ray generating material is facing the interior of the vacuum chamber and the electron source, but x-rays 888 are also propagate through the back side of the target 100 towards the beam-splitting grating $G_1$ 210. In other embodiments, a separate window is used, and additional x-ray filters may also be used Once generated by the source 008, the x-rays 888 may pass through an optional shutter 230, an x-ray spectral filter to obtain a desired spectral bandwidth with a desired wavelength, and an object 240-M to be investigated. The x-rays then diffract off the beam splitting grating $G_1$ 210, which may additionally be mounted on a substrate 211, and then fall on the analyzer grating $G_2$ 220, which may also be mounted on a substrate 221. The final interference pattern will be detected by an array detector 290 that provides electrical signals corresponding to the x-ray intensity through a connector 291 to an image processing system 295 for analysis.

In addition to the x-ray source and interference detection system, means to move the object 240-M and the various gratings relative to each other, to the detector, and to the source may be used. In FIG. 10, the image processing system 295 may also be connected through a network 231 to a means 245 of controlling a stage 244 that sets the position and angle of the object 240-M, to a means 215 of controlling a mount 214 that sets the position and angle of the beam splitting grating $G_1$ 210, and to a means 225 of controlling a mount 224 that sets the position and angle of the analyzer grating $G_2$ 220, as well as a possible connection to the shutter 230 or to a switch 013 for the high voltage supply 010 to allow the x-rays to be moved and modulated (such as being turned on and off). Software run by processors in the image processing system 295 may control the motion of the gratings $G_1$ 210, $G_2$ 220, the object 240-M, and also the x-ray exposure to allow the collection of the multiple images needed to obtain detailed amplitude, differential phase, phase-contrast, and scattering contrast images of the object 240-M.

Additional embodiments may also include controls that allow the electron beam to be moved or modulated. For example, embodiments may be designed that additionally comprise a means of translating the x-ray source anode relative to the analyzer grating $G_2$. Additional embodiments that also allow the position and angle of the x-ray detector 290 to be adjusted may also be designed.

Figure 13:
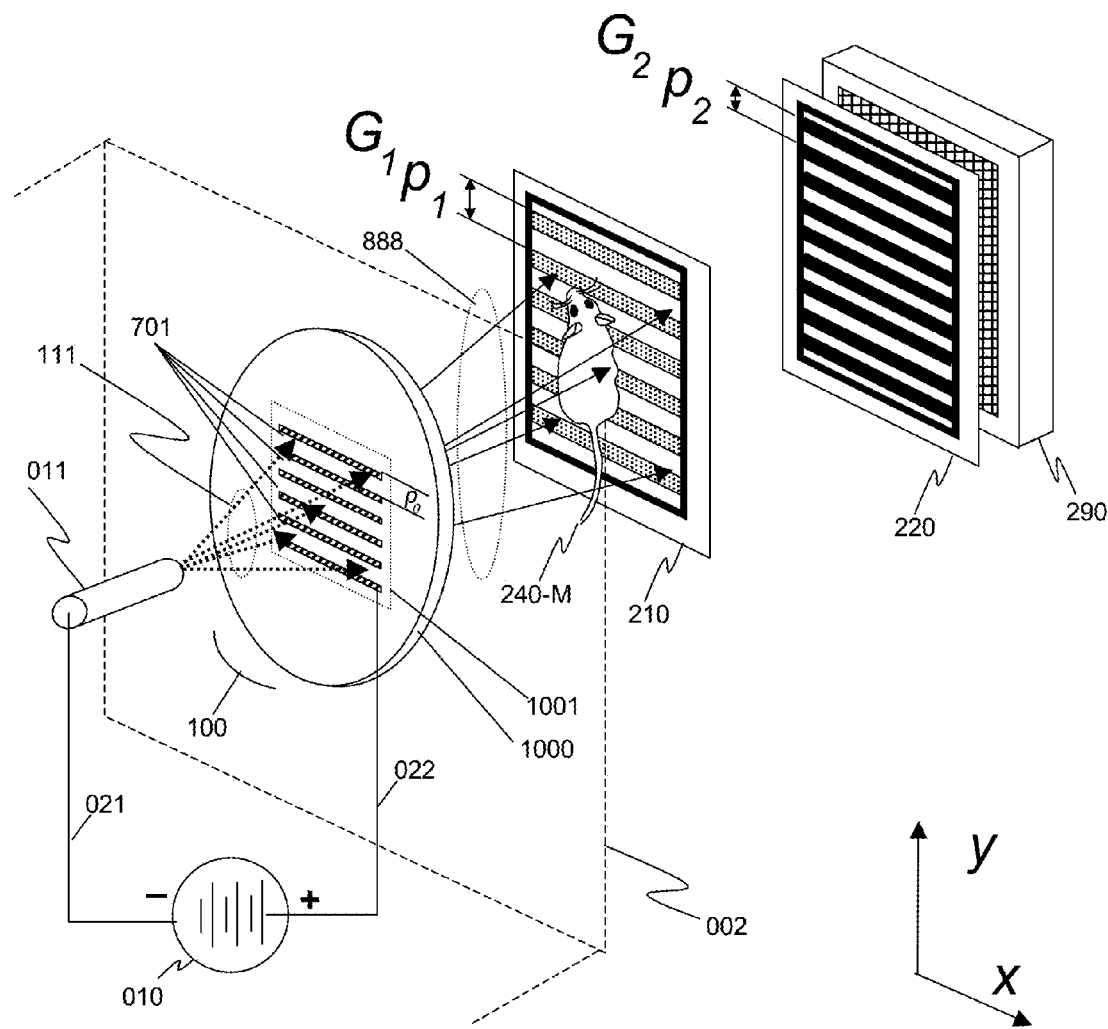
FIG. 13 illustrates a perspective view of an embodiment of the invention in which the x-ray target comprises of x-ray generating microstructures in the form of parallel lines.

FIG. 13 illustrates an embodiment of the invention in which the target 100 comprises a substrate 1000 and a plurality of microstructured line sources 701. These microstructured line sub-sources 701 will typically be a few microns wide in one direction (corresponding to the sub-source size parameter a, generally in the dimension orthogonal to the direction of the lines of the gratings $G_1$ 210 and $G_2$ 220, which corresponds to the y-direction in FIG. 13) but much longer (e.g. up to 1000 microns or several millimeters) in the direction parallel to the lines (which corresponds to the x-direction in FIG. 13). The pitch of the microstructures 701 as sub-sources as shown in FIG. 13 is $p_0$, and is related to the pitch of the analyzer/detector by Equation 4.

Figure 14:
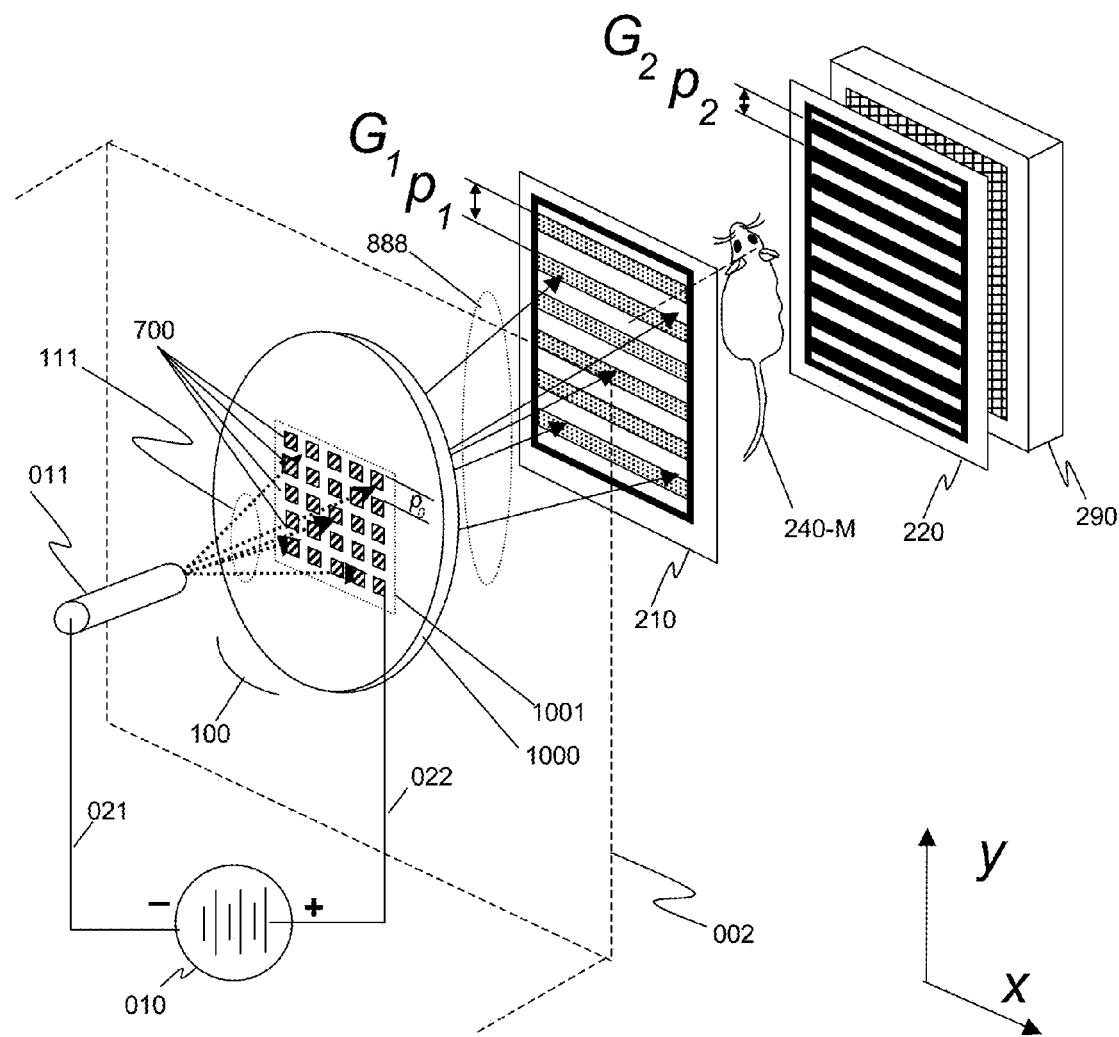
FIG. 14 illustrates a perspective view of an embodiment of the invention in which the object (a mouse) is placed between the gratings $G_1$ and $G_2$.

FIG. 14 illustrates an embodiment of the invention in which the object 240-M to be examined is placed between the gratings $G_1$ 210 and the detector 290. The microstructures 700 of x-ray generating material on the target as illustrated in FIG. 14 comprise sub-sources arranged in a 2-D periodic array in two orthogonal directions, but may be any periodic array that satisfies the coherence illumination condition of the beam-splitting grating $G_1$ 210, including a grid, a mesh, a checkerboard, or other periodic structures.

If the gratings comprise one-dimensional structures, the microstructures 700 in the source target 100 need only be periodic in the same direction as the 1-D arrays of $G_1$ 210 and $G_2$ 220 (i.e. the lines of microstructures 701 are ideally parallel to the lines of the gratings) but can have arbitrary or non-periodic structure in the perpendicular direction.

Figure 15:
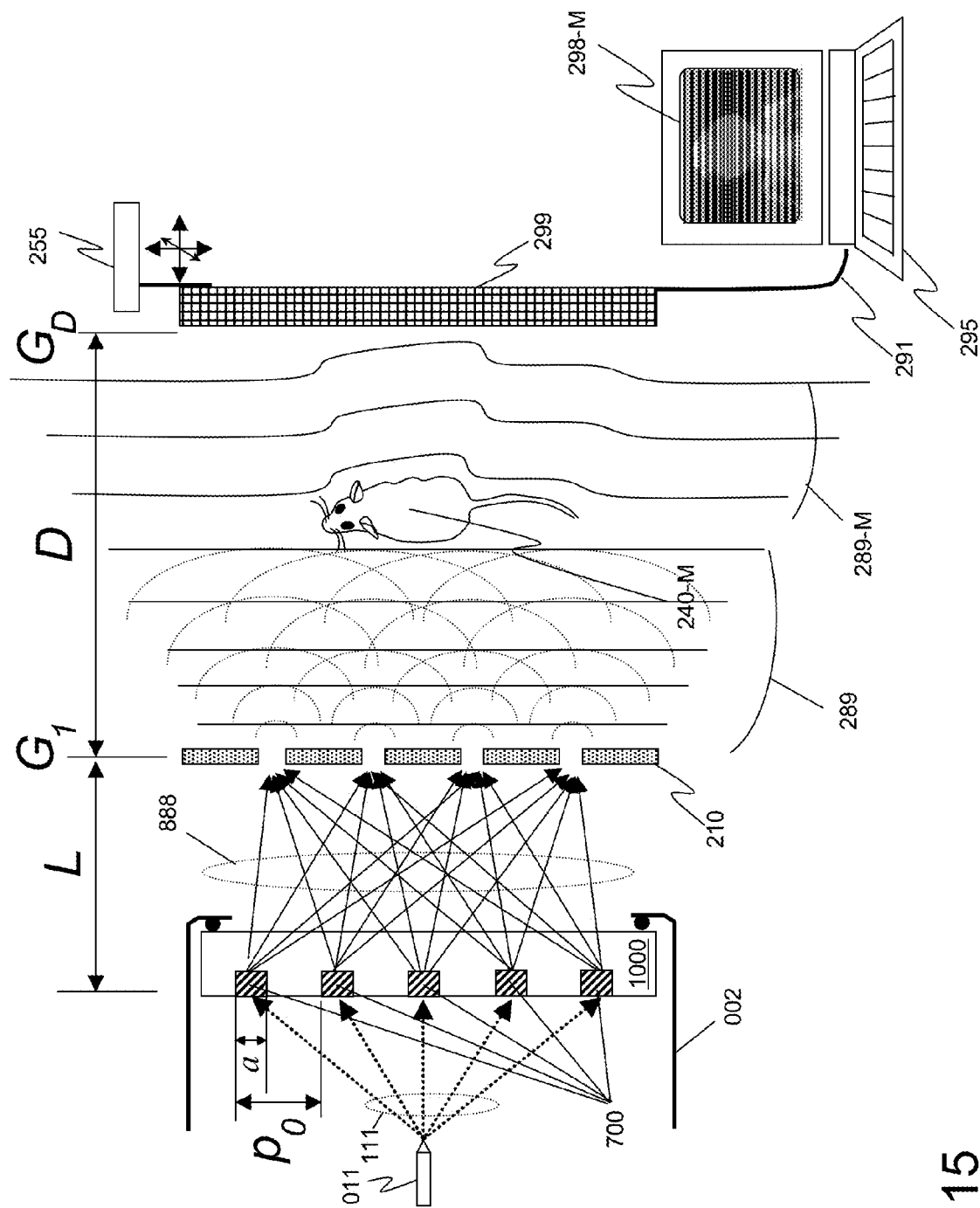
FIG. 15 illustrates a detailed schematic cross-section view of an embodiment of the invention in which a high-resolution detector is used without an analyzer grating.

FIG. 15 additionally illustrates an embodiment of the invention in which the there is no analyzer grating $G_2$ 220, but instead the detector 299 has a high resolution array $G_D$ with a pixel resolution equal to or better than one third (⅓) of the Talbot fringe period in the direction orthogonal to the grating lines. With this resolution, a single exposure image may be processed to obtain absorption, phase, and scattering contrast images simultaneously. This can be advantageous in that the intensity loss of 50% or more that typically occurs for x-rays passing through $G_2$ 220 is avoided, and the signal reaching the detector and therefore the signal-to-noise ratio is substantially higher.

In order to collect the multiple images for the calculation of detailed amplitude, differential phase, phase-contrast, and scattering contrast images for an object 240-M, the embodiment of FIG. 15 may additionally comprise a means 255 for translating the detector 290, not only in the two lateral directions parallel to the plane of the grating $G_1$, but also in direction defined along the path of x-ray propagation, to ensure that the detector 299 is placed at the correct multiple of the Talbot distance $T_D$.

Figure 16:
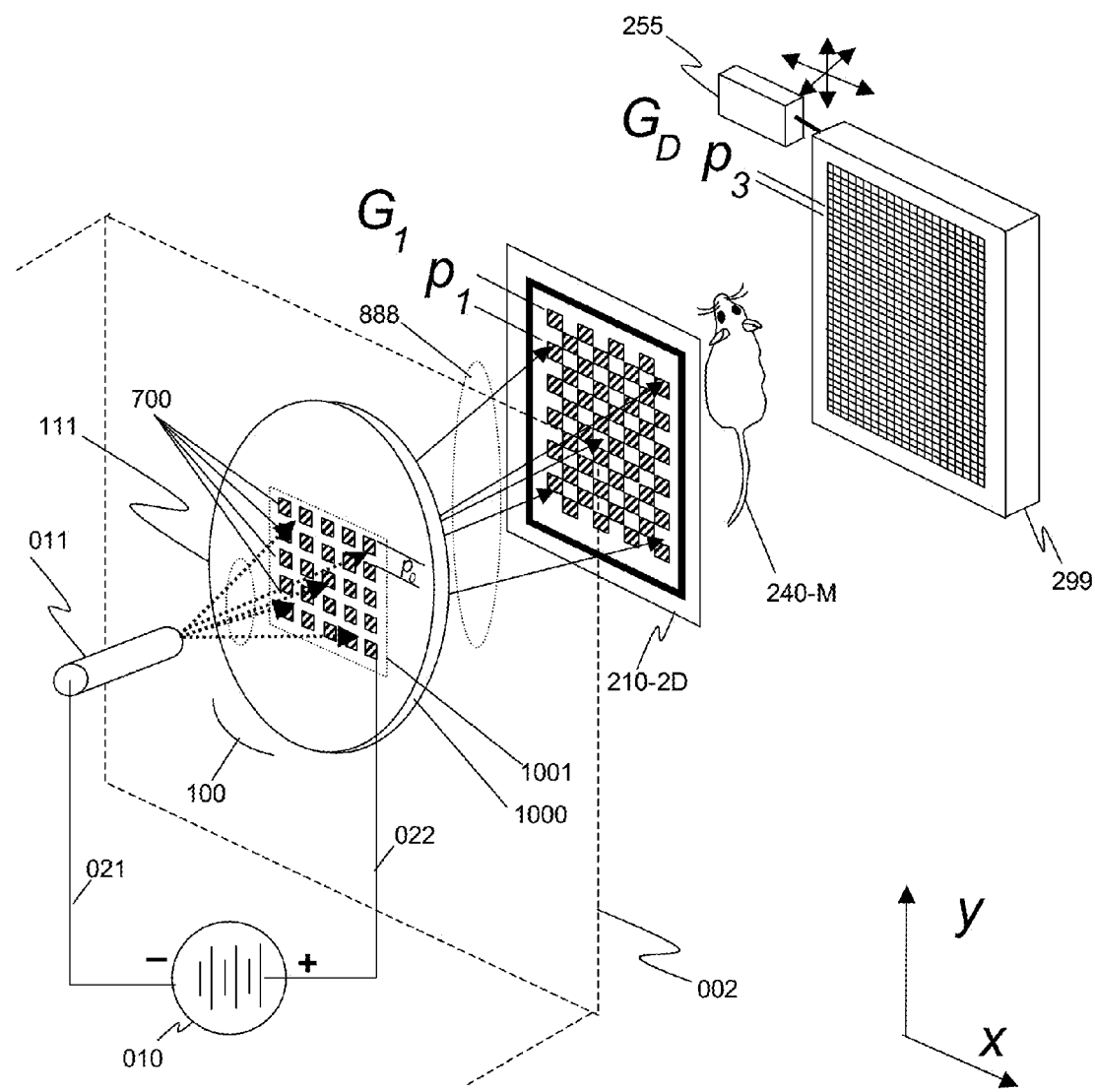
FIG. 16 illustrates a perspective view of an embodiment of the invention in which the object (a mouse) is placed between the grating $G_1$ and the detector, and the grating $G_1$ comprises a two-dimensional phase structure.
Figure 17:
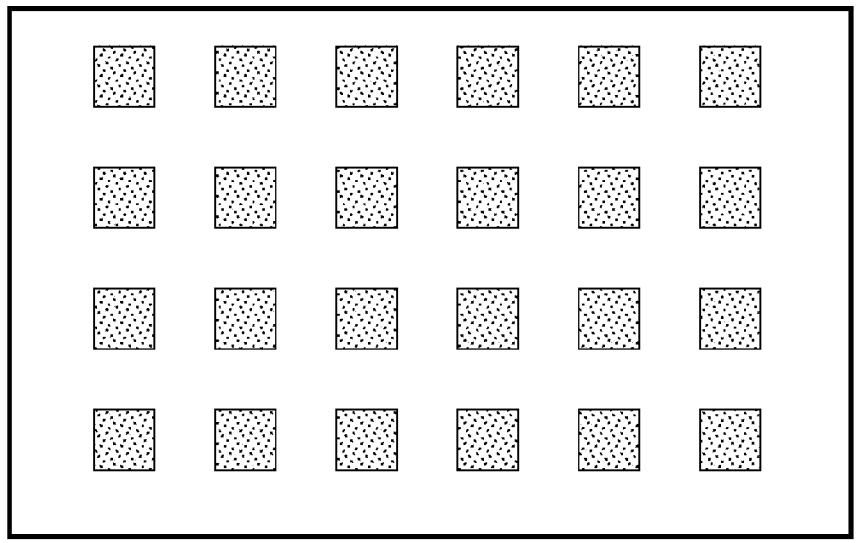
FIG. 17 illustrates a "mesh" 2-D pattern for a beam splitting grating used in some embodiments of the invention.
Figure 17:
Figure 17:
Figure 18:
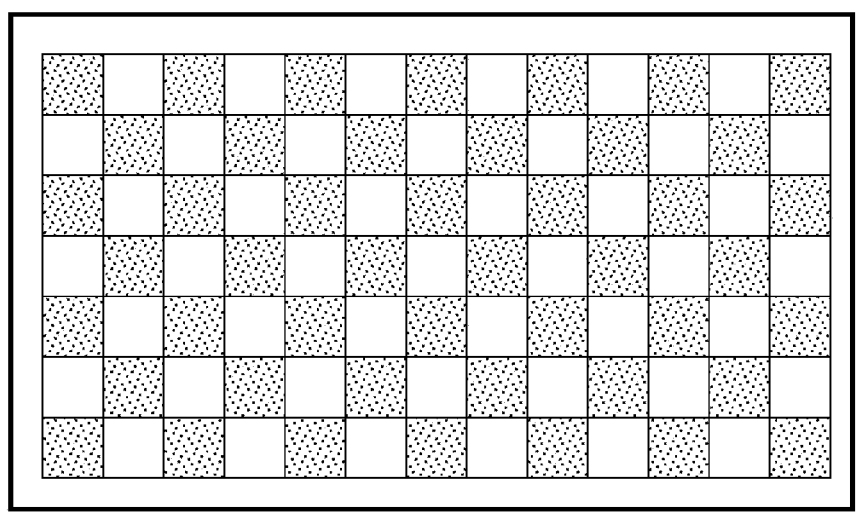
FIG. 18 illustrates a "checkerboard" 2-D pattern for a beam splitting grating used in some embodiments of the invention.
Figure 18:
Figure 18:

FIG. 16 illustrates an embodiment of the invention in which the beam splitting grating $G_1$ 210-2D comprises a two-dimensional periodic array, which may be either a transmission or a phase grating. When using a 2-D beam-splitting grating of this type, the patterns may be arranged in any one of a number of periodic patterns, including a mesh, such as the pattern illustrated in FIG. 17, or a checkerboard pattern, as illustrated in FIG. 18, In these illustrations, clear regions are non-phase shifted regions, while patterned regions represent regions with a relative phase shift. Different, or even opposite relative phase shifts, may also be used in some embodiments, i.e., the clear regions can be phased shifted while the patterned regions are not.

For use with an incident x-ray beam with a spectral bandwidth of less than ±15% around the mean energy, a beam splitting grating with a phase shift of $\pi$ radians and a line-to-space ratio of 1:1 may be preferred. For use with an incident beam with a spectral bandwidth greater than ±15%, a relative phase shift of $\pi/2$ radians may be preferred.

The beam splitting gratings in some embodiments may have a profile comprising 1-D stripes, such as a Ronchi profile or structures having a rectangular profile. The relative phase shift between the dark and clear stripes is preferably selected to be $\pi$ or $\pi/2$ radians, but may also be any integer multiple or fraction of $\pi$. Alternatively, the dark stripes may have low x-ray transmission so that the beam splitting grating is an absorption grating.

FIG. 16 illustrates the use of a 2-D beam splitting grating $G_1$ 210-2D in conjunction with a high-resolution detector 299, as was also shown in FIG. 15. To simultaneously obtain a differential phase contrast, phase contrast, absorption, scattering contrast images in two orthogonal directions, the geometric parameters, including the x-ray sub-source size a, the period $p_1$ of the grating $G_1$ 210-2D and the distance L, need to satisfy the coherence illumination condition of the grating $G_1$ in both directions. As before, the detector 299 has spatial resolution equal to or better than ⅓ of the Talbot fringe period in the two orthogonal directions in the image plane and is positioned to be aligned with the Talbot fringe pattern.

Such embodiments with 2-D patterns on the beam splitting grating $G_1$ 210-2D may also be used with the previously described lower resolution detector 290 in conjunction with a two-dimensional analyzer grating $G_2$ which may be phase stepped in two directions in any sequence so that the phase information is obtained in both orthogonal directions. Similar to the description of $G_1$ 210-2D above, this 2-D analyzer grating $G_2$ may be of any periodic structure such as a mesh, a checkerboard, or 2-D array of structures such as circles, triangles, squares, rectangles, etc.

Figure 19:
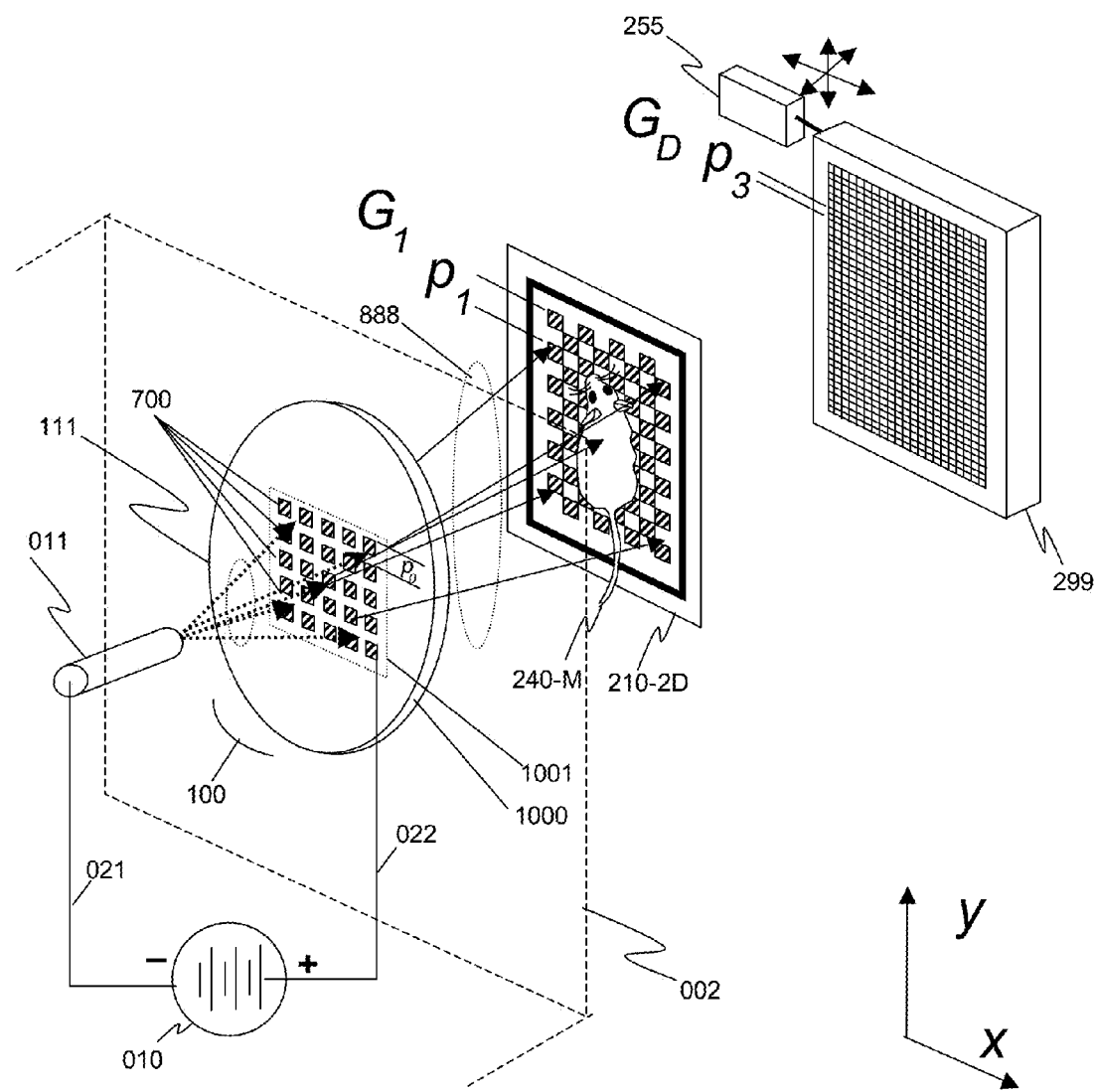
FIG. 19 illustrates a perspective view of an embodiment of the invention in which the object (a mouse) is placed between the source and the grating $G_1$, and the grating $G_1$ comprises a two-dimensional phase structure.

FIG. 19 represents an embodiment similar to FIG. 16, except that the object 240-M under examination is now placed between the x-ray source and the beam-splitting grating 210-2D.

Note that some of the embodiments are one-dimensional Talbot-Yun interferometers in which absorption, phase, and scattering information is obtained in one direction and incorporate one or more 1-D gratings in combination with a micro structured source target that is periodic in at least in the direction perpendicular to the grating line direction (but may be periodic in other directions as well). Other embodiments are two-dimensional Talbot-ST interferometers in which absorption, phase, and scattering information is obtained in two orthogonal directions (or all three dimensions by performing computed tomography using the 2-D Talbot-Yun setup).

Figure 20:
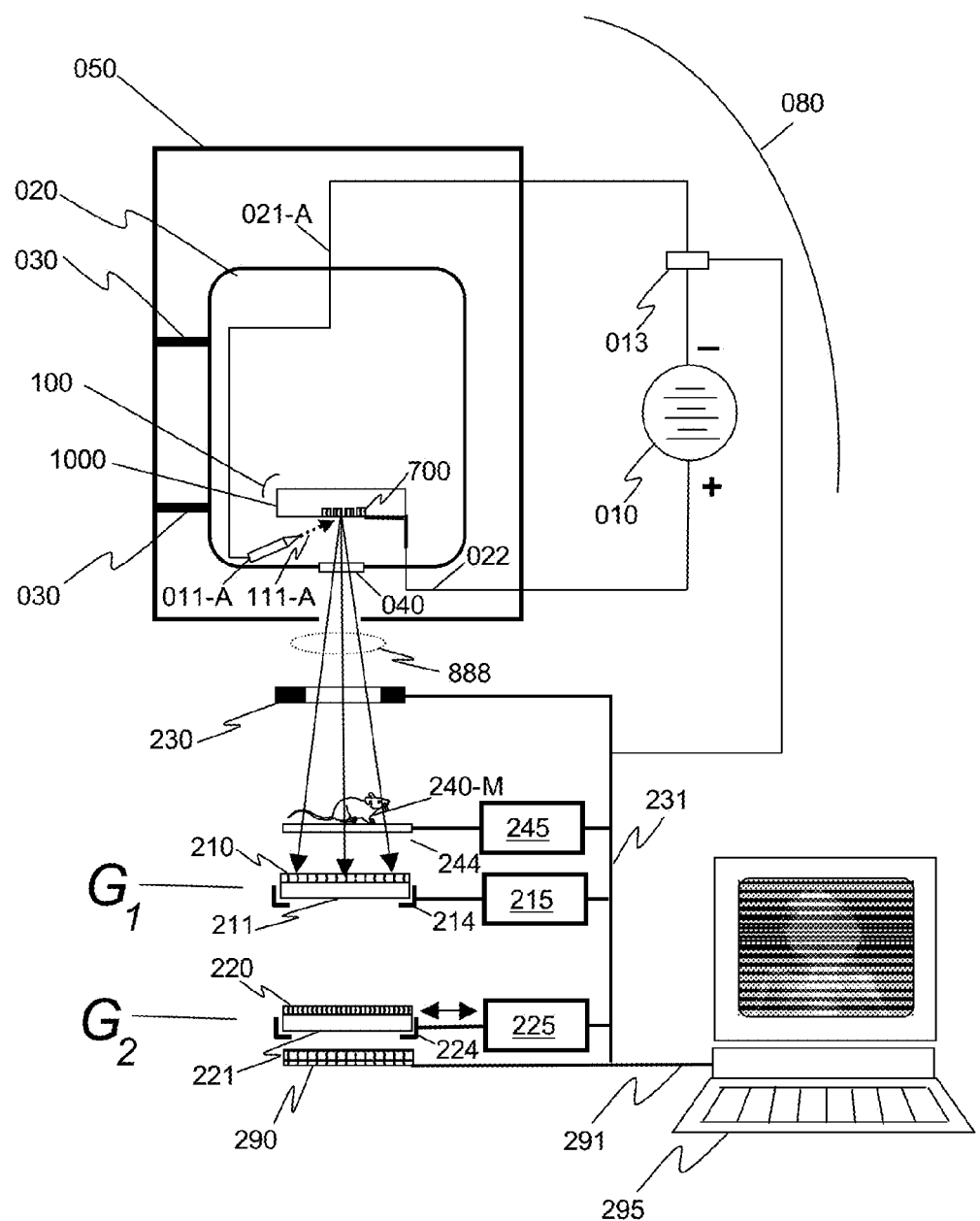
FIG. 20 illustrates a schematic cross-section view of an embodiment of the invention in which the target is mounted within the vacuum chamber.
Figure 21:
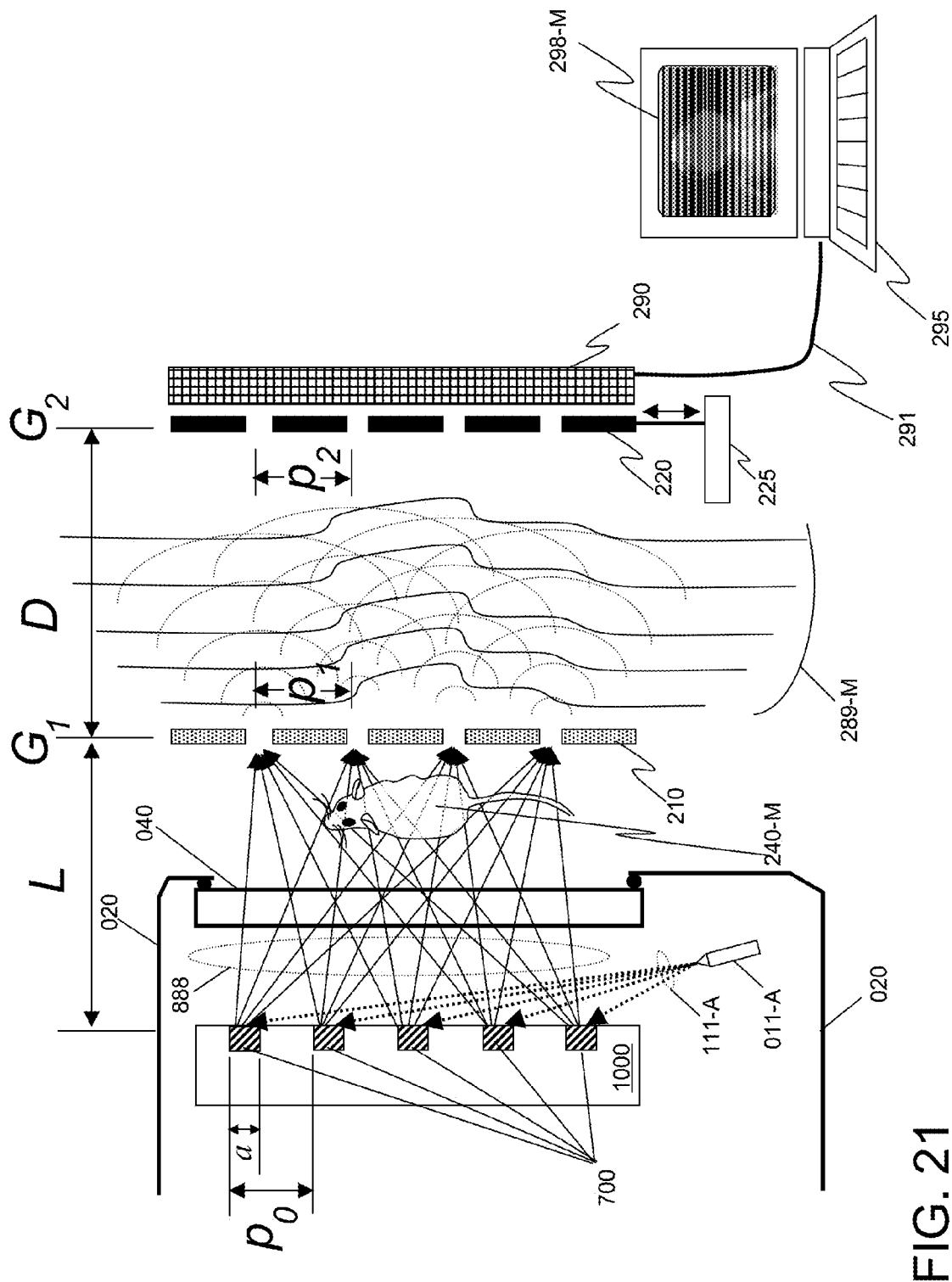
FIG. 21 illustrates a detailed schematic cross-section view of the embodiment of the invention shown in FIG. 20.

FIGS. 20 and 21 illustrate another embodiment of the invention in which the x-ray source 080 comprises a vacuum chamber 020 supported on mounts 030 within an x-ray shielding housing 050. The source 080 also comprises a target 100 comprising a substrate 1000 and a periodic pattern comprising x-ray sub-sources 700 mounted entirely within the vacuum chamber 020. As before, this embodiment also comprises a high voltage source 010, which has a negative terminal connected through a lead 021-A to an electron emitter 011-A, while the positive terminal is connected through one or more leads 022 to the microstructures in the target, allowing them to serve as an anode.

However, in this embodiment, the surface of the target 100 comprising the periodic array of x-ray sub-sources 700 comprising of x-ray generating material is facing a window 040 mounted in the wall of the vacuum chamber 020, and the electron emitter 011-A is aligned to emit a beam of electrons 111-A onto the surface of the target 100 comprising sub-sources 700 facing the window 040.

Figure 22:
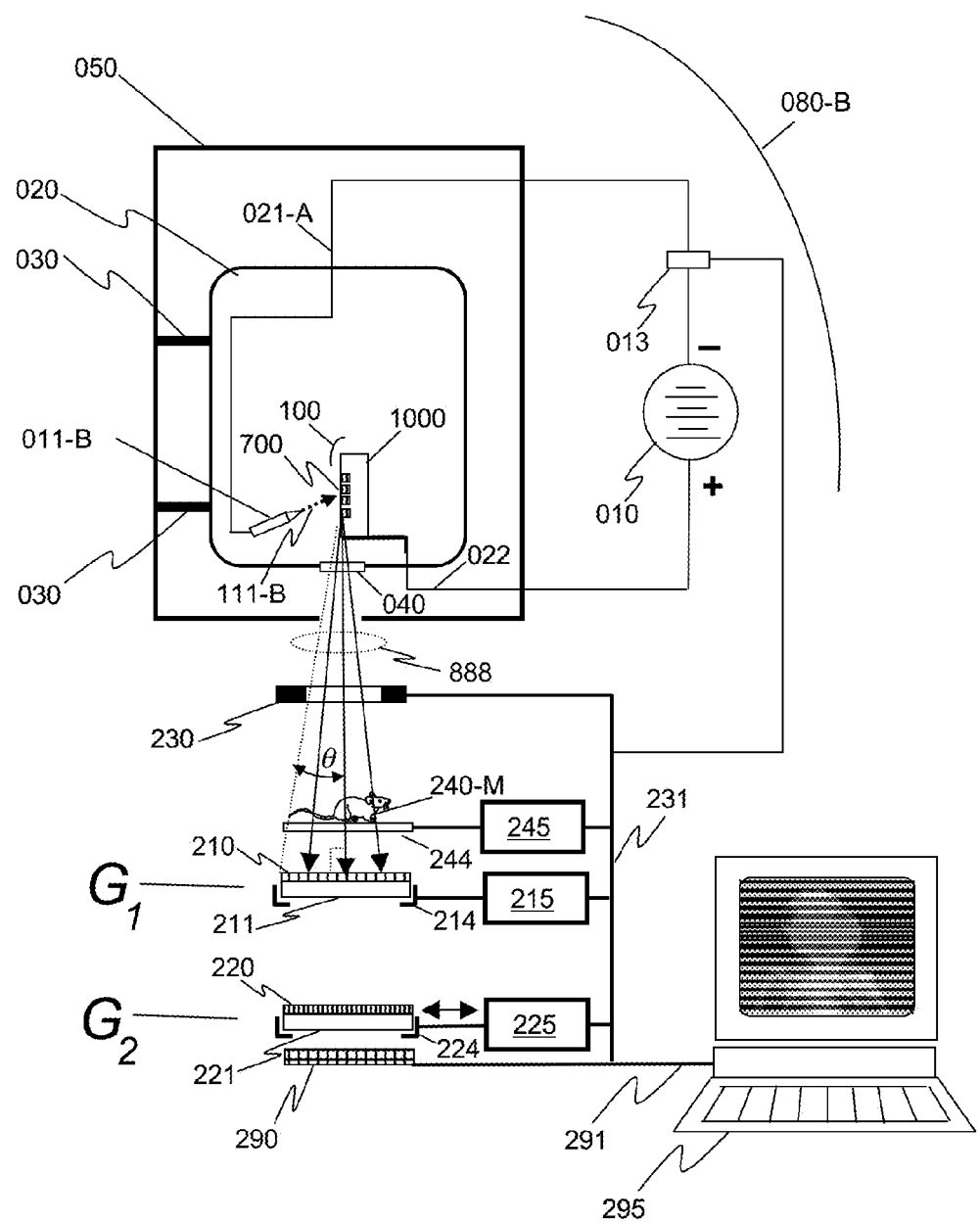
FIG. 22 illustrates a schematic cross-section view of an embodiment of the invention in which the target is mounted within the vacuum chamber and x-rays are generated using linear accumulation.
Figure 23:
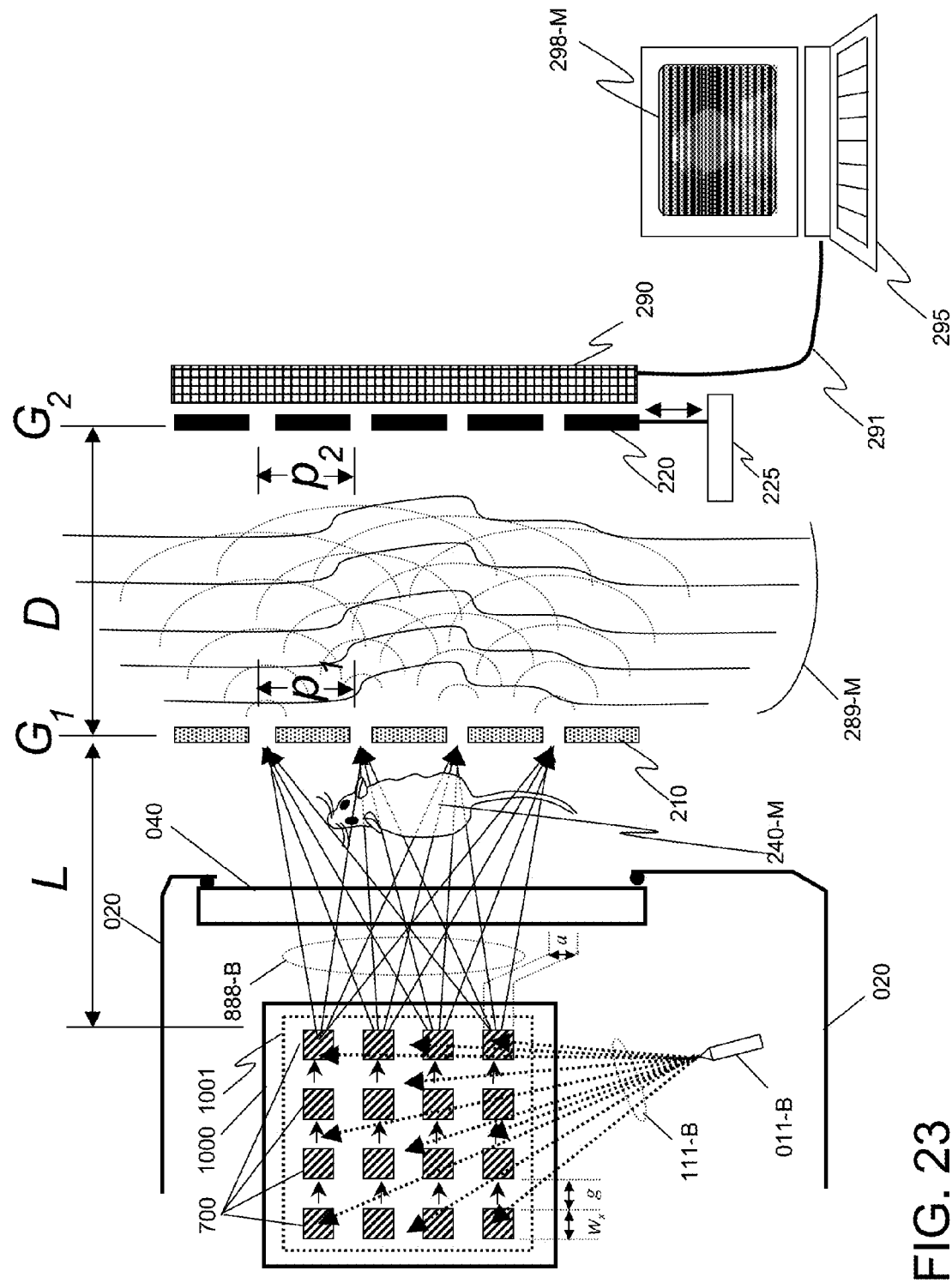
FIG. 23 illustrates a detailed schematic cross-section view of the embodiment of the invention shown in FIG. 22.

FIGS. 22 and 23 illustrate another embodiment of the invention in which the target 100 comprising a substrate 1000 and a periodic pattern comprising x-ray sub-sources 700 mounted entirely within the vacuum chamber 020. As before, this embodiment also comprises a high voltage source 010, which has a negative terminal connected through a lead 021-B to an electron emitter 011-B, while the positive terminal is connected through one or more leads 022 to the microstructures in the target, allowing them to serve as an anode.

However, in this embodiment, the surface of the target 100 comprising the periodic array of x-ray sub-sources 700 comprising x-ray generating material is oriented such that x-rays produced by some of the microstructures propagate towards other microstructures that are also producing x-rays, and a linear accumulation of x-rays 888-B from a plurality of microstructures 700 emerges from the target. The distance g between the microstructures and microstructures 700 emerges from the target. The distance g between the microstructures and the width $w_x$ in the propagation direction should be small enough such that the emission from the nth microstructure contributing to the accumulated x-rays can be considered as a single sub-source with dimension a of Eqn. 9, i.e.:

$$a \geq \tan\theta \cdot (n(g+w_x)) \qquad [\text{Eqn. 10}]$$

where a is the sub-source dimension that meets the coherence requirements of the system, and $\theta$ is one half of the field-of-view angle for the system.

Linear accumulation of x-ray sources as used in this embodiment of the invention is described more fully in the co-pending U.S. patent application entitled X-RAY SOURCES USING LINEAR ACCUMULATION by the inventors of the present invention (U.S. patent application Ser. No. 14/490,672 filed Sep. 19, 2014), which is hereby incorporated by reference in its entirety. Any of the source designs and configurations disclosed in the above referenced co-pending application may be considered for use as a component in any or all of the interferometric imaging systems disclosed herein.

Figure 24:
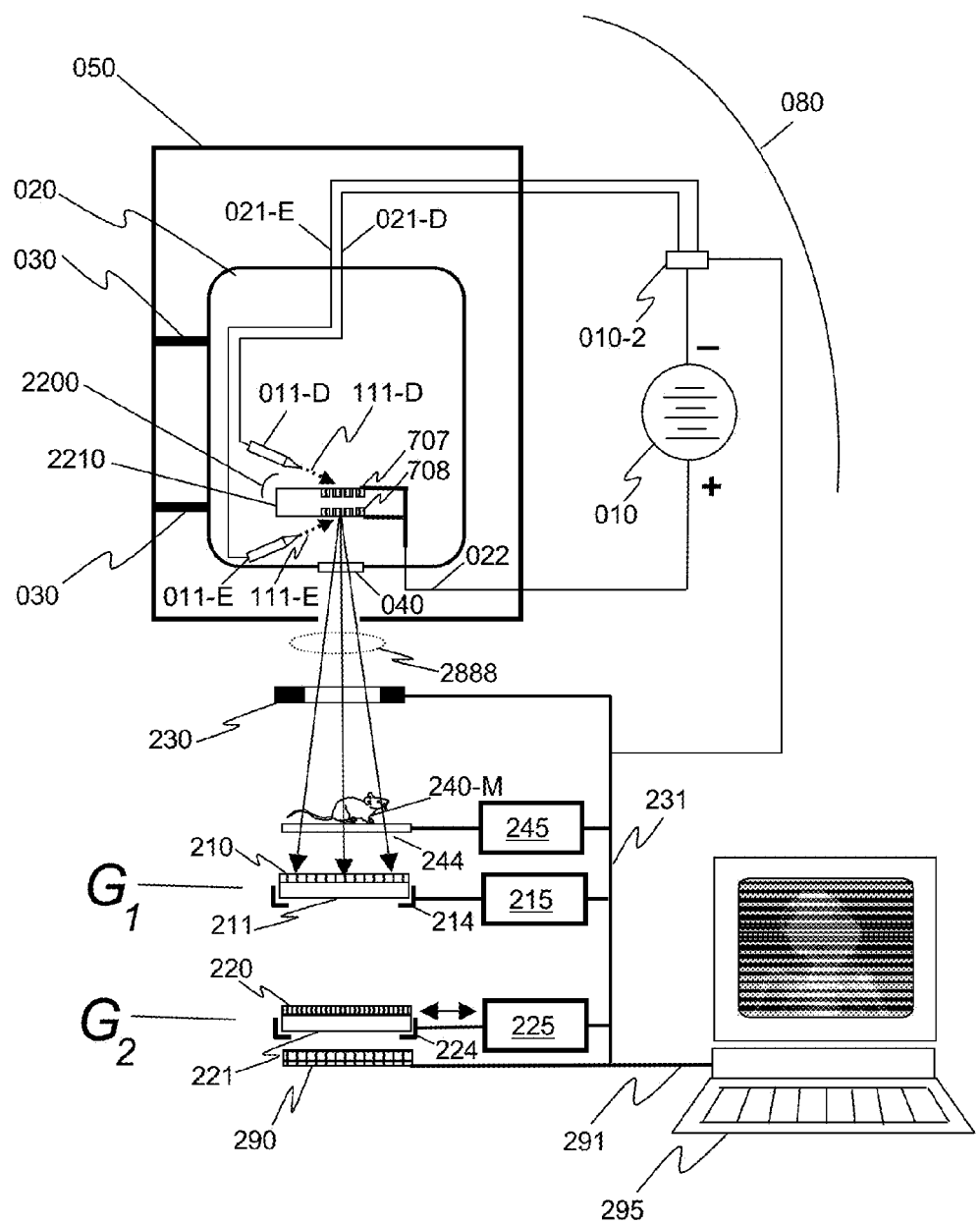
FIG. 24 illustrates a schematic cross-section view of an embodiment of the invention in which two electron beams bombard the target from both sides.
Figure 25:
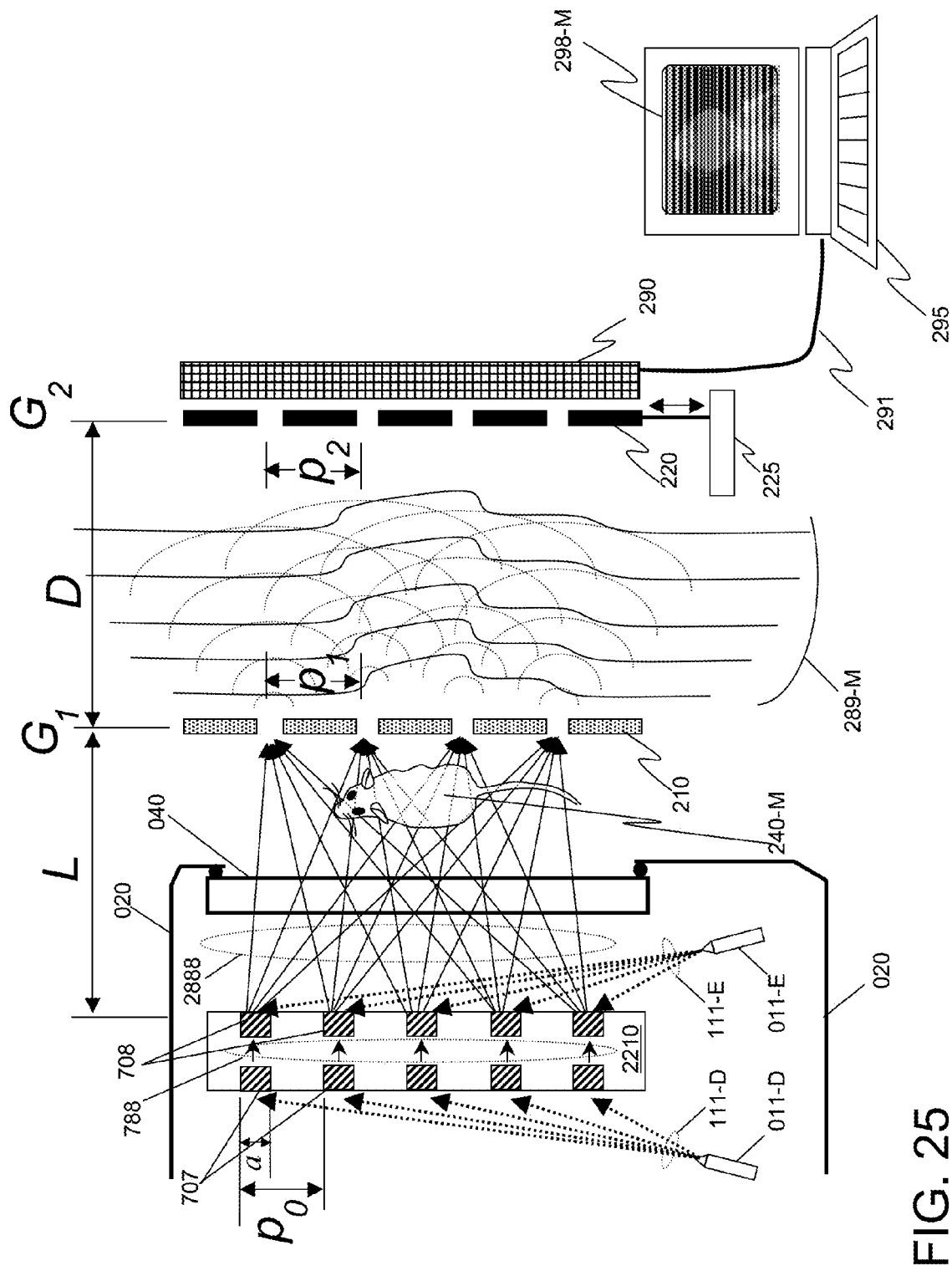
FIG. 25 illustrates a detailed schematic cross-section view of the embodiment of the invention shown in FIG. 24.

Likewise, FIGS. 24 and 25 illustrate another embodiment of the invention that utilizes linear accumulation of x-rays. In this embodiment, the x-ray source 080 includes a target 2200 comprising a substrate 2210 and a first set of sub-sources 707 and a second set of sub-sources 708 mounted entirely within the vacuum chamber 020. As before, this embodiment also comprises a high voltage source 010, but this high voltage source is connected to a junction 010-2 that provides high voltage to two electron emitters 011-D and 011-E through leads 021-D and 021-E, respectively. As shown in FIGS. 24 and 25, the first electron emitter 021-D provides an electron beam 111-D that bombards the first set of sub-sources 707, while the second electron emitter 021-E provides an electron beam 111-E that bombards the second set of sub-sources 708. Some of the x-rays 788 generated by the first set of sub-sources 707 and the second set of sub-sources 708 along the x-ray imaging beam axis combine to produce x-rays 2888 from the target 2200 will be augmented by the linear accumulation of x-rays from these two sets of x-ray sub-sources. In some embodiments, the separation between the two sets of sub-sources 707 and 708 may be smaller than 5 mm but larger than the source size in direction perpendicular to a line passing through the center of the two sub-sources. The periods of both the sub-sources 707 and 708 may be selected so that the associated Talbot fringes downstream of the beam splitting grating $G_1$ substantially overlap.

It will also be known to those skilled in the art that other embodiments of the invention comprising an x-ray source in which the target/anode under bombardment by electrons is moved, translated, or rotated to distribute the heat load are also possible.

Note: The illustrations of FIGS. 10 through 25 are not shown to scale, and are meant to illustrate the principle of the invention and not specific relationships between the microstructures 700, the target 100 and the various grating periods $p_1$ and $p_2$. The microstructures 700, 701, 707, 708 etc. may be on the order of microns in size, while the object under examination 240-M may be centimeters in size. Likewise, although these are illustrated in which an object with dimensions on the order of centimeters (a mouse) is shown, the techniques described are not limited to such objects, but may be used to examine even larger structures, or microscopic structures as well, as long as a suitable resolution for the detector and other elements of the interferometer are suitably constructed.

2. Fabrication of X-Ray Targets

Targets such as those to be used in x-ray sources according to the invention disclosed herein have been described in detail in the U.S. patent application entitled STRUCTURED TARGETS FOR X-RAY GENERATION by the inventors of the present invention (U.S. patent application Ser. No. 14/465,816, filed Aug. 21, 2014), which is hereby incorporated by reference in its entirety. Any of the target designs and configurations disclosed in the above referenced co-pending application may be considered for use as a component in any or all of the x-ray sources disclosed herein.

As described herein and in the above cited pending patent applications, the target used in the source of x-rays may comprise a periodic array of sub-sources. Each sub-source may be comprised of a single or multiple microstructures of x-ray generating material in thermal contact with, or preferably embedded in, a substrate selected for its thermal conductivity. When the microstructures are in good thermal contact with a substrate having a high thermal conductivity, higher electron current densities may be used to generate x-rays, since the excess heat will be drawn away into the substrate. The higher current densities will give rise to higher x-ray flux, leading to a higher brightness source. As described in the above co-pending patent applications, sources with microstructures of x-ray generating material may have a brightness more than 10 times larger than simpler constructions made from the same materials. Additional configurations in which multiple sub-sources are aligned to contribute x-rays on the same axis can multiply the brightness further through linear accumulation of the x-ray sub-sources.

It should also be noted here that, when the word "microstructure" is used herein, it is specifically referring to microstructures comprising x-ray generating material. Other structures, such as the cavities used to form the x-ray microstructures, have dimensions of the same order of magnitude, and might also be considered "microstructures". As used herein, however, other words, such as "structures", "cavities", "holes", "apertures", etc. may be used for these structures when they are formed in materials, such as the substrate, that are not selected for their x-ray generating properties. The word "microstructure" will be reserved for structures comprising materials selected for their x-ray generating properties.

Likewise, it should be noted that, although the word "microstructure" is used, x-ray generating structures with dimensions smaller than 1 micron, or even as small as nano-scale dimensions (i.e. greater than 10 nm) may also be described by the word "microstructures" as used herein as long as the properties are consistent with the geometric factors for sub-source size and grating pitches set forth in the various embodiments.

It should also be noted that here that, when the word "sub-source" is used it may refer to a single microstructure of x-ray generating material, or an ensemble of smaller microstructures that function similarly to a single structure for the purposes of Talbot interferometry.

The fabrication of these microstructured targets may follow well known processing steps used for the creation of embedded structures in substrates. If the substrate is a material with high thermal conductivity such as diamond, conventional lithographic patterning, such as focused ion beam lithography or electron beam lithography, using photoresists can produce micron sized structures, which may then be etched into the substrate using processes such as reactive ion etching (RIE). Deposition of the x-ray generating material into the etched structures formed in the substrate may then be carried out using standard deposition processes, such as electroplating, chemical vapor deposition (CVD), atomic layer deposition, or hot pressing.

The x-ray generating material used in the target should ideally have good thermal properties, such as a high melting point and high thermal conductivity, in order to allow higher electron power loading on the source to increase x-ray production. The x-ray generating material should additionally be selected for good x-ray production properties, which includes x-ray production efficiency (proportional to its atomic number) and in some cases, it may be desirable to produce a specific spectra of interest, such as a characteristic x-ray spectral line. For these reasons, targets are often fabricated using tungsten, with an atomic number Z=74. Table I lists several materials that are commonly used for x-ray targets, several additional potential target materials (notably useful for specific characteristic lines of interest), and some materials that may be used as substrates for target materials. Melting points, and thermal and electrical conductivities are presented for values near 300° K (27° C.). Most values are cited from the *CRC Handbook of Chemistry and Physics*, 90$^{th}$ ed. [CRC Press, Boca Raton, Fla., 2009]. Other values are cited from various sources found on the Internet. Note that, for some materials Ouch as sapphire for example) thermal conductivities an order of magnitude larger may be possible when cooled to temperatures below that of liquid nitrogen (77° K) [see, for example, Section 2.1.5, *Thermal Properties*, of E. R. Dobrovinskaya et al., *Sapphire: Material, Manufacturing, Applications*, Springer Science+Business Media, LLC, 2009].

TABLE I

Various Target and Substrate Materials and Selected Properties.

| Material (Elemental Symbol) | Atomic Number Z | Melting Point ° C. (1 atm) | Thermal Conductivity (W/(m ° C.)) | Electrical Conductivity (MS/m) |
|---|---|---|---|---|
| Common Target Materials: | | | | |
| Chromium (Cr) | 24 | 1907 | 93.7 | 7.9 |
| Iron (Fe) | 26 | 1538 | 80.2 | 10.0 |
| Cobalt (Co) | 27 | 1495 | 100 | 17.9 |
| Copper (Cu) | 29 | 1085 | 401 | 58.0 |
| Molybdenum (Mo) | 42 | 2623 | 138 | 18.1 |
| Silver (Ag) | 47 | 962 | 429 | 61.4 |
| Tungsten (W) | 74 | 3422 | 174 | 18.4 |
| Other Possible Target Materials: | | | | |
| Titanium (Ti) | 22 | 1668 | 21.9 | 2.6 |
| Gallium (Ga) | 35 | 30 | 40.6 | 7.4 |
| Rhodium (Rh) | 45 | 1964 | 150 | 23.3 |
| Indium (In) | 49 | 157 | 81.6 | 12.5 |
| Cesium (Cs) | 55 | 28 | 35.9 | 4.8 |
| Rhenium (Re) | 75 | 3185 | 47.9 | 5.8 |
| Gold (Au) | 79 | 1064 | 317 | 44.0 |
| Lead (Pb) | 82 | 327 | 35.3 | 4.7 |
| Other Potential Substrate Materials with low atomic number: | | | | |
| Beryllium (Be) | 4 | 1287 | 200 | 26.6 |
| Carbon (C): Diamond | 6 | * | 2300 | $10^{-19}$ |
| Carbon (C): Graphite ∥ | 6 | * | 1950 | 0.25 |
| Carbon (C): Nanotube (SWNT) | 6 | * | 3180 | 100.0 |
| Carbon (C): Nanotube (bulk) | 6 | * | 200 | |
| Boron Nitride (BN) | B = 5 N = 7 | ** | 20 | $10^{-17}$ |
| Silicon (Si) | 14 | 1414 | 124 | $1.56 \times 10^{-9}$ |
| Silicon Carbide (β-SiC) | Si = 14 C = 6 | 2798 | 0.49 | $10^{-9}$ |
| Sapphire (Al$_2$O$_3$) ∥ C | Al = 13 O = 8 | 2053 | 32.5 | $10^{-20}$ |

\* Carbon does not melt at 1 atm; it sublimes at ~3600° C.
\*\* BN does not melt at 1 atm; it sublimes at ~2973° C.

Figure 26:
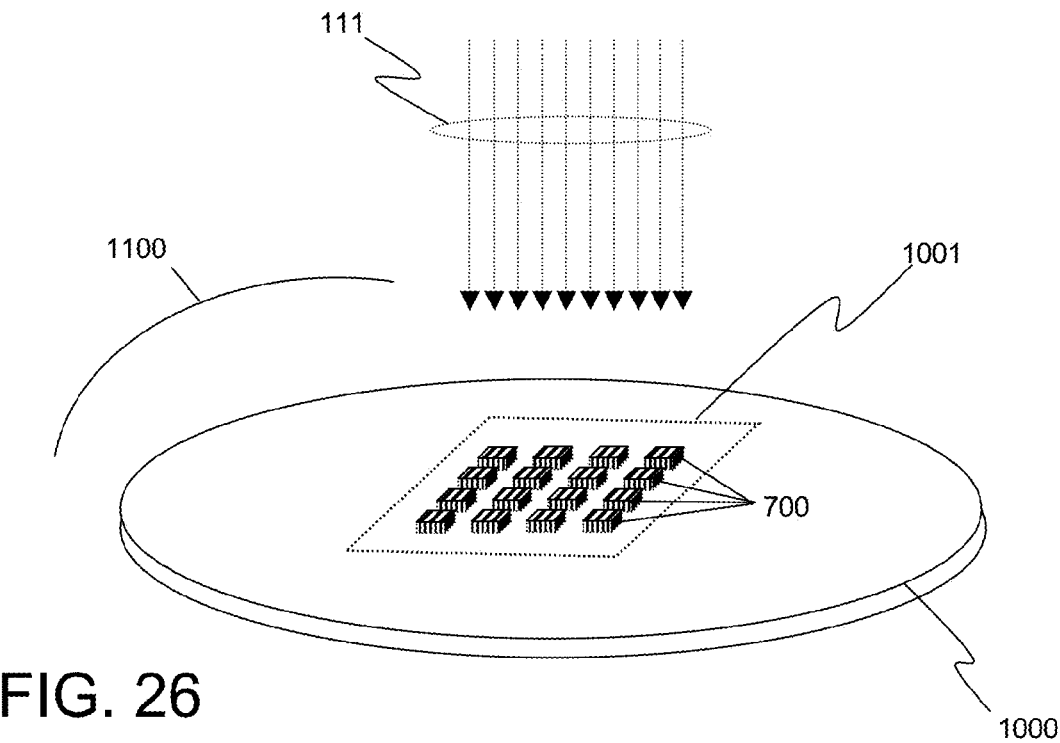
FIG. 26 illustrates a perspective view of a target comprising a grid of embedded rectangular target microstructures on a larger substrate that may be used in some embodiments of the invention.

FIG. 26 illustrates a target as may be used in some embodiments of the invention. In this figure, a substrate 1000 has a region 1001 that comprises an array of sub-sources 700 comprising microstructures of x-ray generating material (typically a metallic material), in which the sub-sources are arranged in a regular array of right rectangular prisms. In a vacuum, electrons 111 bombard the target from above, and generate heat and x-rays in the microstructures 700. The material in the substrate 1000 is selected such that it has relatively low x-ray production (efficiency is proportional to atomic number) and energy deposition rate (stopping power is proportional to density) for electrons in comparison to the x-ray generating microstructure material, and therefore will not generate a significant amount of heat and x-rays. This is typically achieved by selecting a low mass density and low atomic number (Z) material for the substrate.

The substrate 1000 material may also be chosen to have a high thermal conductivity, typically larger than 100 W/(m ° C.), and the microstructures are typically embedded within the substrate, i.e. if the microstructures are shaped as rectangular prisms, it is preferred that at least five of the six sides are in close thermal contact with the substrate 1000, so that heat generated in the microstructures 700 is effectively conducted away into the substrate 1000. However, targets used in other embodiments may have fewer direct contact surfaces. In general, when the term "embedded" is used in this disclosure, at least half of the surface area of the microstructure will be in close thermal contact with the substrate.

Note that the sub-source sizes and dimensions in some embodiments may be constrained by the same limitations as the periodicity $p_0$ of the grating $G_0$ in prior art. In other words, the spatial resolution achievable at the object position in the x-ray interferometric imaging systems as shown in FIGS. 9 through 25 is determined by the overall x-ray source size and the detector resolution, similar to the conditions described in the prior art interferometeric imaging systems, such as the Talbot-Lau system. Therefore, the maximum x-ray source size (width of each microstructure spot) is limited for a given detector resolution and a given imaging geometry as determined by the distance between the source and object and the distance between the object to the detector.

The line-to-space ratio of the arrays of sub-sources is a design parameter that should be considered in the design of any system. A large spatial coherence length is inversely proportional to the size of an x-ray source or sub-source. Because the fringe visibility of the Talbot interference fringes increases linearly with the relative ratio of the spatial coherence length of the illuminating x-ray beam to the period of the beam-splitting grating $p_1$ for a value of the ratio from 0.3 to 1, it is generally preferred to have a small source size. However, the x-ray production is inversely proportional to the area of the sub-source (e.g. a reduction in line width will lead to a decrease of x-ray production). Since the throughput of an imaging system is generally proportional to square of the contrast transfer function and only proportional to the x-ray flux, it is generally preferred to have a line-to-space ration less than 1:1. Some embodiments of the invention may use a line-to-space (i.e. x-ray generating material to substrate material) ratio between 1:5 and 1:2 (i.e. the relative area of the x-ray generating material may range from 20% to 33%).

A figure of merit (FOM) that may be helpful for the selection of materials for targets according to this invention is the ratio of x-rays produced by the microstructures to the x-rays produced by the electrons also bombarding the substrate. This figure of merit may be useful for the design of and selection of materials for the targets for the system, and should be taken into consideration in addition to the thermal conductivity of the substrate. As the electron energy deposition rate is proportional to the mass density and the x-ray production efficiency in a material is proportional to its atomic number, this figure of merit may be defined as follows:

$$FOM = \frac{Z_2 \times \rho_2}{Z_1 \times \rho_1} \qquad [\text{Eqn. 11}]$$

where Z is the atomic number and ρ is the density, and material 1 is the substrate and material 2 is the x-ray generating material.

TABLE II

Figure of Merit for x-ray material/substrate combinations.

| Substrate material | | | Microstructure material | | Figure of Merit |
|---|---|---|---|---|---|
| Material | Atomic # $Z_1$ | Mass density (g/cm³) | Material | Atomic # $Z_2$ | Mass density (g/cm³) | $\frac{Z_2 \times \rho_2}{Z_1 \times \rho_1}$ |
| SiC | 12.55 | 3.21 | Cu | 29 | 8.96 | 6 |
| Si | 14 | 2.33 | Cu | 29 | 8.96 | 8 |
| SiC | 12.55 | 3.21 | Mo | 42 | 10.2 | 11 |
| Diamond | 6 | 3.5 | Cu | 29 | 8.96 | 12 |
| Si | 14 | 2.33 | Mo | 42 | 10.2 | 13 |
| Diamond | 6 | 3.5 | Mo | 42 | 10.2 | 21 |
| SiC | 12.55 | 3.21 | W | 74 | 19.25 | 35 |
| Be | 4 | 1.85 | Cu | 29 | 8.96 | 35 |
| Si | 14 | 2.33 | W | 74 | 19.25 | 44 |
| Be | 4 | 1.85 | Mo | 42 | 10.2 | 59 |
| Diamond | 6 | 3.5 | W | 74 | 19.25 | 68 |
| Be | 4 | 1.85 | W | 74 | 19.25 | 193 |

A number of microstructures and substrate material combinations are listed below in Table II. Any of the following combinations may be used, but it is preferable that the materials are selected such that the FOM is greater than 12, and that the thermal conductivity of the substrate material is greater than 100 W/(m ° C.) at room temperature.

Figure 27:
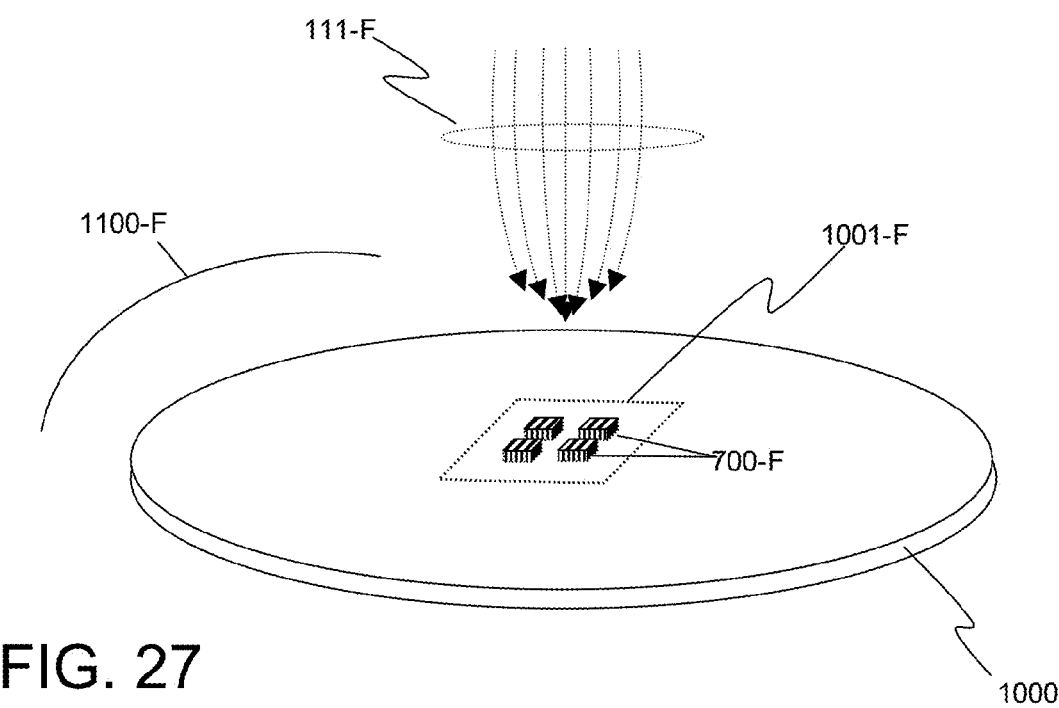
FIG. 27 illustrates a perspective view of a variation of a target comprising a grid of embedded rectangular target microstructures on a larger substrate for use with focused electron beam that may be used in some embodiments of the invention.

FIG. 27 illustrates another target as may be used in some embodiments of the invention in which the electron beam 111-F is directed by electrostatic lenses to form a more concentrated, focused spot. For this situation, the target 1100-F will still comprise a region 1001-F comprising an array of microstructures 700-F comprising x-ray material, but the size and dimensions of this region 1001-F can be matched to regions where electron exposure will occur. In these targets, the "tuning" of the source geometry and the x-ray generating material can be controlled such that the designs mostly limit the amount of heat generated to the micro structured region 1001-F, while also reducing the design and manufacturing complexity. This may be especially useful when used with electron beams focused to form a micro-spot, or by more intricate systems that form a more complex electron exposure pattern.

The depth of penetration of electrons into the material can be estimated by Pott's Law [P. J. Potts, Electron Probe Microanalysis, Ch. 10 of *A Handbook of Silicate Rock Analysis*, Springer Netherlands, 1987, p. 336)], which states that the penetration depth x in microns is related to the 10% of the value of the electron energy $E_0$ in keV raised to the 3/2 power, divided by the density of the material:

$$x\,(\mu m) = 0.1 \times \frac{E_0^{1.5}}{\rho} \qquad [\text{Eqn. 12}]$$

For less dense material, such as a diamond substrate, the penetration depth is much larger than for a material with greater density, such as most materials containing elements used for x-ray generation.

Using this formula, Table III illustrates some of the estimated penetration depths for some common x-ray target materials.

TABLE III

Estimates of penetration depth for 60 keV electrons into some materials.

| Material | Z | Density (g/cm³) | Penetration Depth (μm) |
|---|---|---|---|
| Diamond | 6 | 3.5 | 13.28 |
| Copper | 29 | 8.96 | 5.19 |
| Molybdenum | 42 | 10.28 | 4.52 |
| Tungsten | 74 | 19.25 | 2.41 |

The majority of characteristic Cu K x-rays are generated within the penetration depth. The electron interactions below that depth typically generate few characteristic K-line x-rays but will contribute to the heat generation, thus resulting in a low thermal gradient along the depth direction. It is therefore preferable in some embodiments to set a maximum thickness for the microstructures in the target in order to limit electron interaction in the material and optimize local thermal gradients. One embodiment of the invention limits the depth of the micro structured x-ray generating material in the target to between one third and two thirds of the electron penetration depth in the substrate at the incident electron energy. In this case, the lower mass density of the substrate leads to a lower energy deposition rate in the substrate material immediately below the x-ray generating material, which in turn leads to a lower temperature in the substrate material below. This results in a higher thermal gradient between the x-ray generating material and the substrate, enhancing heat transfer. The thermal gradient is further enhanced by the high thermal conductivity of the substrate material.

For similar reasons, selecting the thickness of the microstructures to be less than one half of the electron penetration depth in the substrate is also generally preferred for efficient generation of bremsstrahlung radiation, because the electrons below that depth have lower energy and thus lower x-ray production efficiency.

Note: Other choices for the dimensions of the x-ray generating material may also be used. In targets as used in some embodiments of the invention, the depth of the x-ray material may be selected to be 50% of the electron penetration depth in the substrate. In other embodiments, the depth of the x-ray material may be selected to be 33% of the electron penetration depth in the substrate. In other embodiments, the depth for the microstructures may be selected related to the "continuous slowing down approximation" (CSDA) range for electrons in the material. Other depths may be specified depending on the x-ray spectrum desired and the properties of the selected x-ray material.

Figure 28A:
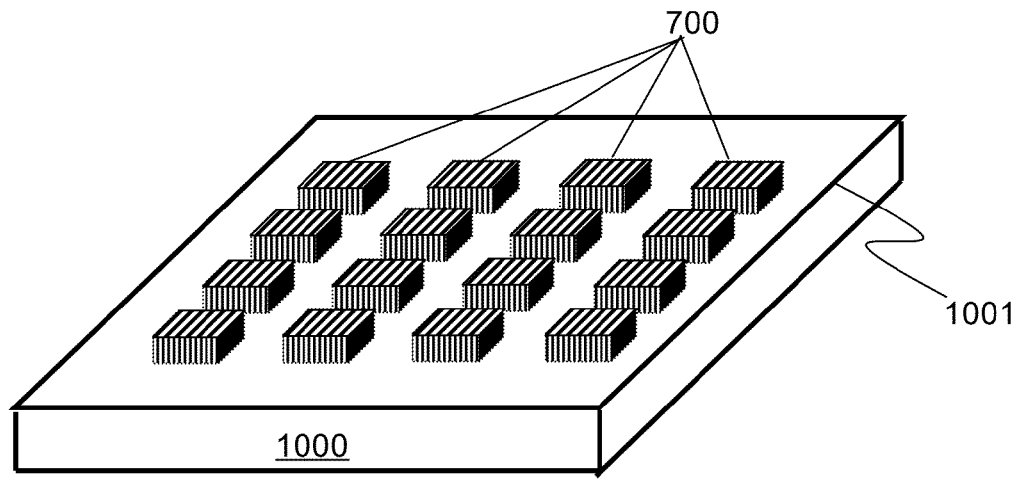
FIG. 28A illustrates a perspective view of a target comprising a grid of embedded rectangular target microstructures as used in some embodiments of the invention.
Figure 28B:
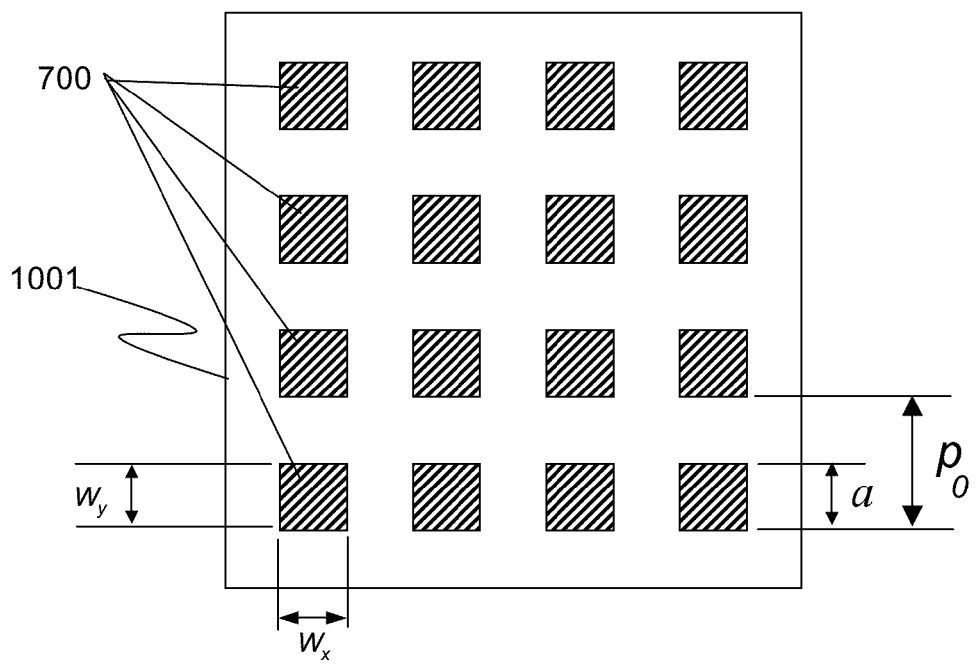
FIG. 28B illustrates a top view of the target of FIG. 28A.
Figure 28C:
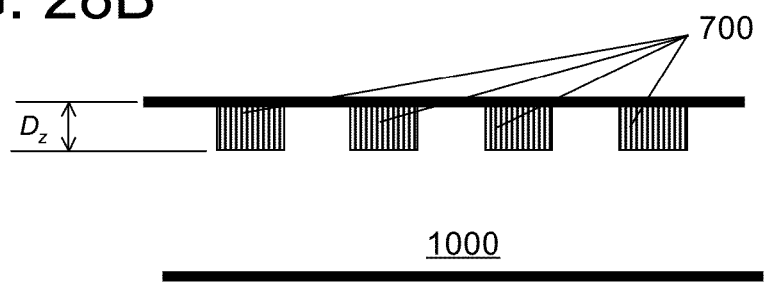
FIG. 28C illustrates a side/cross-section view of the target of FIGS. 28A and 28B.

FIG. 28 illustrates a region 1001 of a target as may be used in some embodiments of the invention that comprises an array of sub-sources 700 with microstructures in the form of right rectangular prisms comprising x-ray generating material arranged in a regular array. FIG. 28A presents a perspective view of the sixteen microstructures 700 for this target, while FIG. 28B illustrates a top down view of the same region, and FIG. 28C presents a side/cross-section view of the same region. (For the term "side/cross-section view" in this disclosure, the view meant is one as if a cross-section of the object had been made, and then viewed from the side towards the cross-sectioned surface. This shows both detail at the point of the cross-section as well as material deeper inside that might be seen from the side, assuming the substrate itself were transparent [which, in the case of diamond, is generally true for visible light].)

In these targets, the microstructures have been fabricated such that they are in close thermal contact on five of six sides with the substrate. As illustrated, the top of the microstructures 700 are flush with the surface of the substrate, but other targets in which the microstructure is recessed may be fabricated, and still other targets in which the microstructures present a topographical "bump" relative to the surface of the substrate may also be fabricated.

An alternative target as may be used in some embodiments of the invention may have several microstructures of right rectangular prisms simply deposited upon the surface of the substrate. In this case, only the bottom base of the prism would be in thermal contact with the substrate. For a structure comprising the microstructures embedded in the substrate with a side/cross-section view as shown in FIG. 28C with depth $D_z$ and lateral dimensions in the plane of the substrate of $W_x$ and $W_y$, the ratio of the total surface area in contact with the substrate for the embedded microstructures vs. deposited microstructures is $$\frac{A_{Embedded}}{A_{Deposited}} = 1 + 2D\frac{(W+L)}{(W \times L)} \qquad [\text{Eqn. 13}]$$

With a small value for D relative to W and L, the ratio is essentially 1. For larger thicknesses, the ratio becomes larger, and for a cube (D=W=L) in which 5 equal sides are in thermal contact, the ratio is 5. If a cap layer of a material with similar properties as the substrate in terms of mass density and thermal conductivity is used, the ratio may be increased to 6.

Figure 29A:
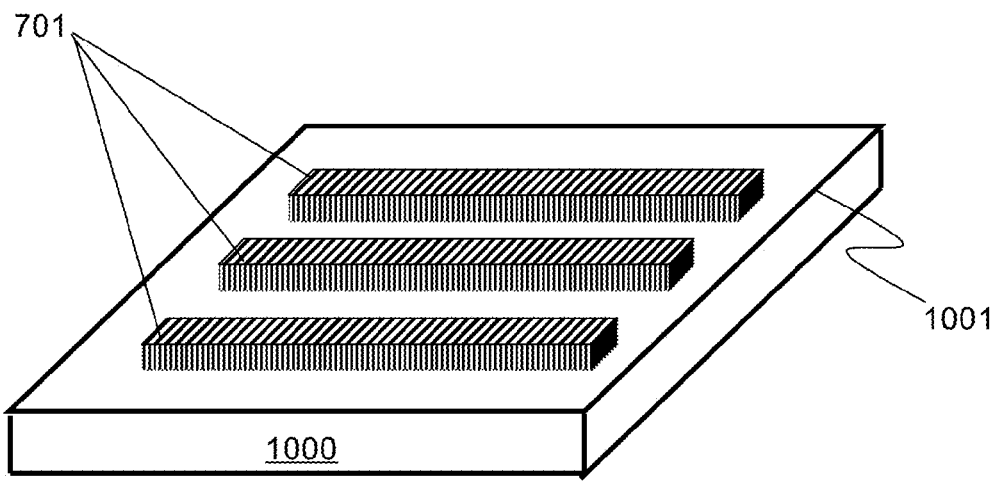
FIG. 29A illustrates a perspective view of a target comprising a set of embedded rectangular target microstructures forming a periodic linear pattern as used in some embodiments of the invention.
Figure 29B:
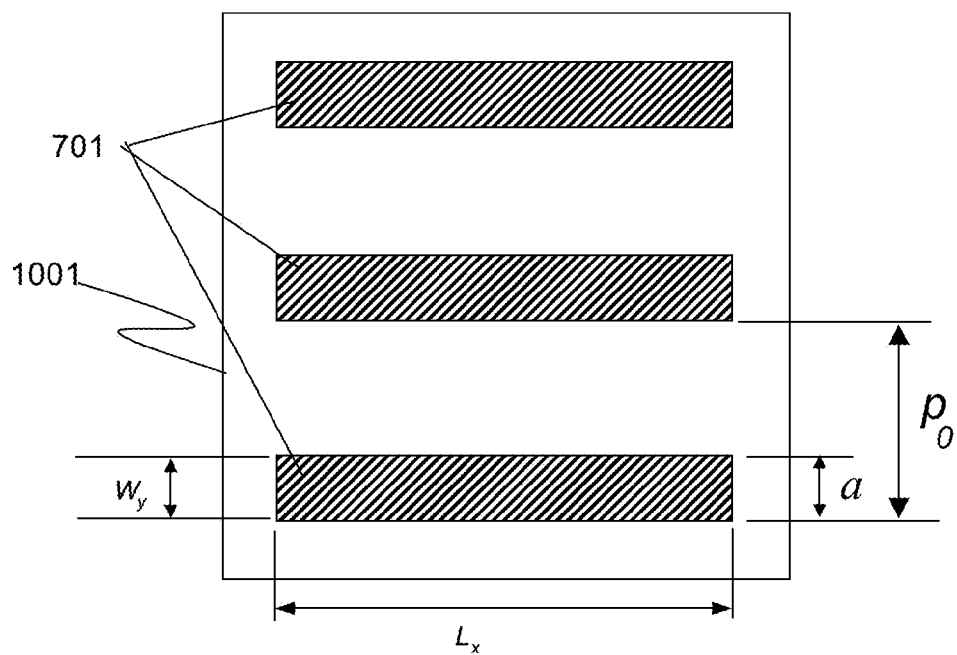
FIG. 29B illustrates a top view of the target of FIG. 29A.
Figure 29C:
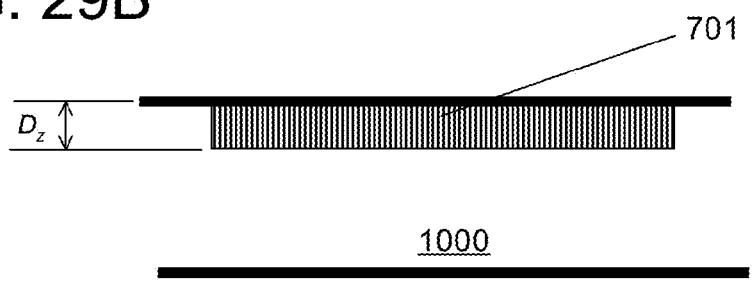
FIG. 29C illustrates a side/cross-section view of the target of FIGS. 29A and 29B.

FIG. 29 illustrates a region 1001 of a target as may be used in some embodiments of the invention, such as that previously illustrated in FIG. 13, that comprises an array of linear sub-sources 701 with microstructures in the form of right rectangular prisms comprising x-ray generating material arranged in a regular array. FIG. 29A presents a perspective view of the three microstructures 701 for this target, while FIG. 29B illustrates a top down view of the same region, and FIG. 29C presents a side/cross-section view of the same region.

In this embodiment, the lateral dimensions in the plane of the substrate are a width and length $W_x$ and $L_y$. The effective sub-source size a will correspond to the width $W_x$.

Figure 30:
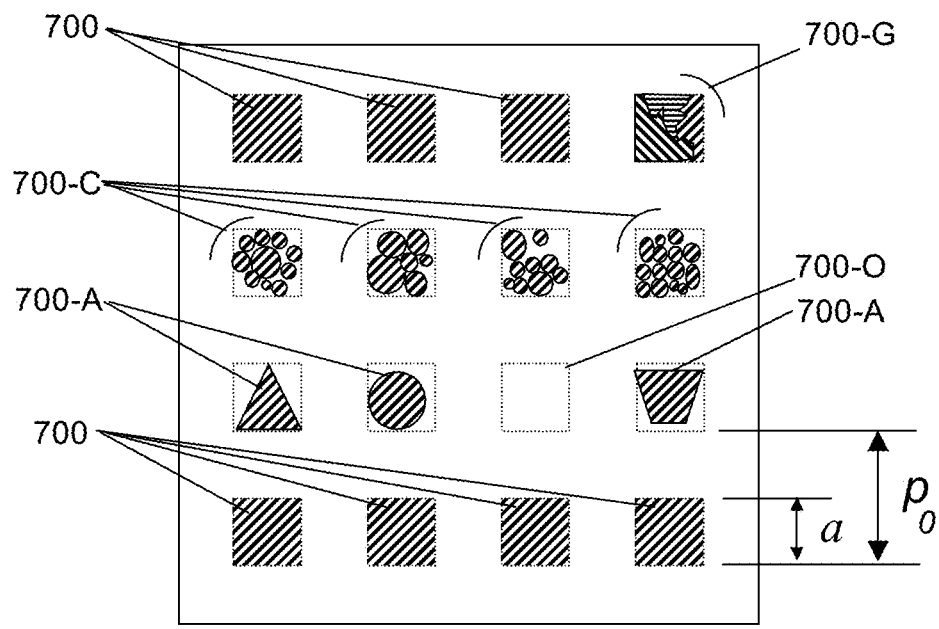
FIG. 30 illustrates variations in target structure for a target as shown in FIGS. 28A-C that may arise from processing variations.
Figure 31:
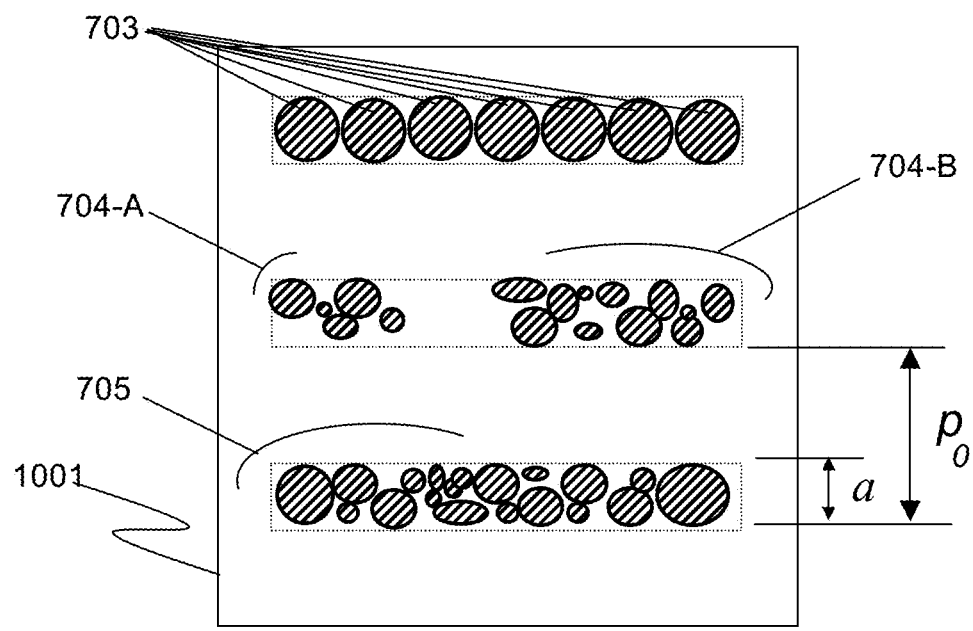
FIG. 31 illustrates variations in target structure for a target as shown in FIGS. 29A-C that may arise from processing variations.

FIGS. 30 and 31 illustrate a practical issue that may arise in forming the targets such as those illustrated in FIGS. 28 and 29. FIG. 30 illustrates variations possible with the grid of x-ray generating microstructures 700 as illustrated in FIG. 28, and FIG. 31 illustrates variations possible with the linear x-ray generating microstructures 701 as illustrated in FIG. 29.

In FIG. 30, odd-shaped microstructures 700-A of other geometric shapes may be formed. Likewise, voids 700-0 may also appear where certain structures may be expected. Other deposition processes, for example deposition using pre-formed particles of x-ray generating material may create ensemble clusters of particles 700-C that, when bombarded with electrons, may still act as x-ray sub-sources similar in function to those that are produced by a uniform structure. Also shown in FIG. 30 is a microstructure with multiple crystal structures and grain boundaries 700-G that again may still produce x-rays similar to those that are produced by a uniform structure, but may be considered to comprise an ensemble of microstructures.

The effective x-ray sub-source size in all of these situations may be approximated using the size parameter a, even though the microstructures comprise particles that are considerable smaller.

FIG. 31 shows examples of ensemble microstructures as may occur when fabricating linear microstructures 701. If uniform pre-fabricated particles of x-ray generating material are created and coated onto the substrate, an ensemble of particles 703 of x-ray generating material may be formed. In other processes, if non-uniform particles are used, clusters of particles 704-A and 704-B may form, in some cases with a non-uniform distribution that may include gaps of voids. In other processes, an ensemble of particles 704 of x-ray generating material may approximate a line source of x-rays.

All of these ensembles, when bombarded with electrons, may still act as x-ray sub-sources similar in function to those that are produced by a uniform linear structure. The effective source size in these situations may be approximated using the size parameter a, even though the microstructures comprise particles that are considerable smaller.

Figure 32:
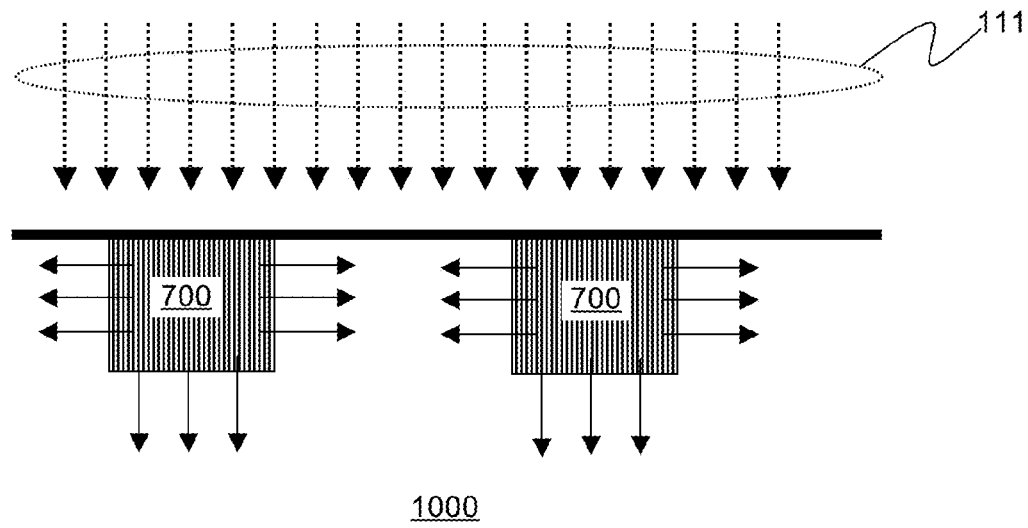
FIG. 32 illustrates a cross-section view of a portion of the target of FIGS. 28A-C and/or FIGS. 29A-C, showing thermal transfer to a thermally conducting substrate under electron beam exposure according to the invention.

The heat transfer that may occur under electron bombardment is illustrated with representative arrows in FIG. 32, in which the heat generated in sub-sources 700 embedded in a substrate 1000 is conducted out of the microstructures comprising the sub-sources 700 through the bottom and sides (arrows for transfer through the sides out of the plane of the drawing are not shown). The amount of heat transferred per unit time ($\Delta Q$) conducted through a material of area A and thickness d given by:

$$\Delta Q = \frac{\kappa \cdot A \cdot \Delta T}{d} \qquad [\text{Eqn. 14}]$$

where κ is the thermal conductivity in W/(m ° C.) and $\Delta T$ is the temperature difference across thickness d in ° C. Therefore, an increase in surface area A, a decrease in thickness d and an increase in $\Delta T$ all lead to a proportional increase in heat transfer.

Figure 33:
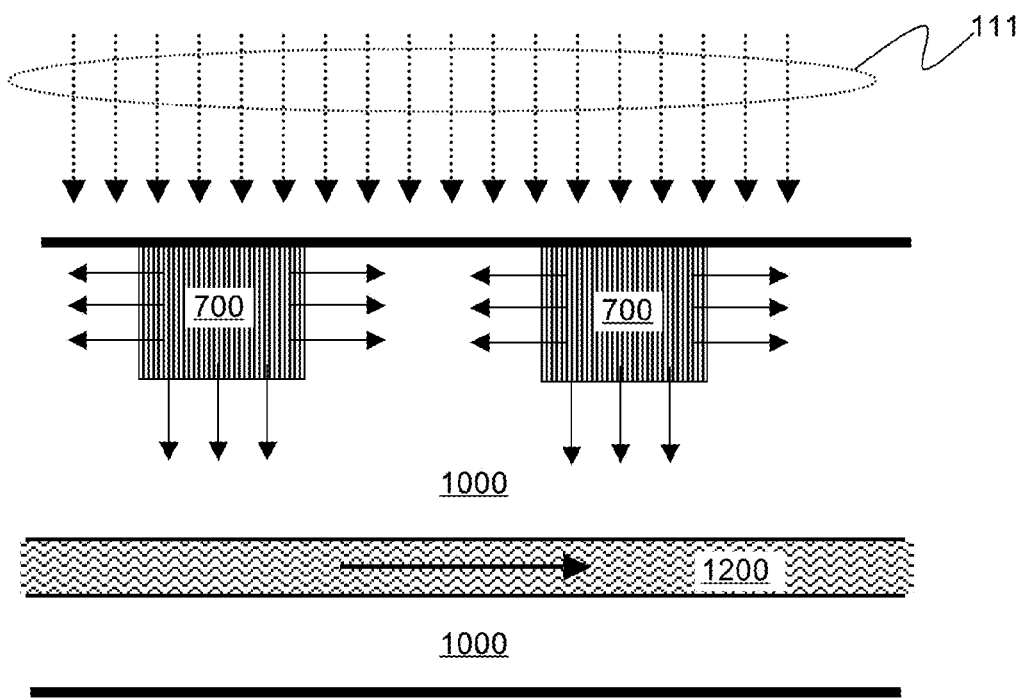
FIG. 33 illustrates a cross-section view of a variation of the target of FIGS. 28A-C, FIGS. 29A-C and/or FIG. 32 comprising a substrate with a thermal cooling channel according to the invention.

An alternative embodiment is illustrated in FIG. 33, in which the substrate additionally comprises a cooling channel 1200. Such cooling channels may be a prior art cooling channel, as discussed above, using water or some other cooling fluid to conduct heat away from the substrate, or may be fabricated according to a design adapted to best remove heat from the regions near the embedded microstructures 700.

Other target structures for various embodiments may be understood or devised by those skilled in the art, in which the substrate may, for example, be bonded to a heat sink, such as a copper block, for improved thermal transfer. The copper block may in turn have cooling channels within it to assist in carrying heat away from the block. Alternatively, the substrate may be attached to a thermoelectric cooler, in which a voltage is applied to a specially constructed semiconductor device. In these devices, the flow of current causes one side to cool while the other heats up. Commercially available devices, such as Peltier coolers, can produce a temperature difference of up to 70° C. across the device, but may be limited in their overall capacity to remove large amounts of heat from a heat source. Heat pipes containing a heat transfer fluid that evaporates and condenses, as are used for cooling CPU chips in server farms when compact design is a consideration, may also be used to cool the substrate.

Alternatively, the substrate can be attached to a cryogenic cooler, such as a block containing channels for the flow of liquid nitrogen, or be in thermal contact with a reservoir of liquid nitrogen or some other cryogenic substance, such as an antifreeze solution, to provide more extreme cooling. When the substrate comprises a material such as diamond, sapphire, silicon, or silicon carbide, thermal conductivity generally increases with decreasing temperature from room temperature. In such a case, designing the target so that it can withstand cooling to these lower temperatures may be preferred.

Figure 34:
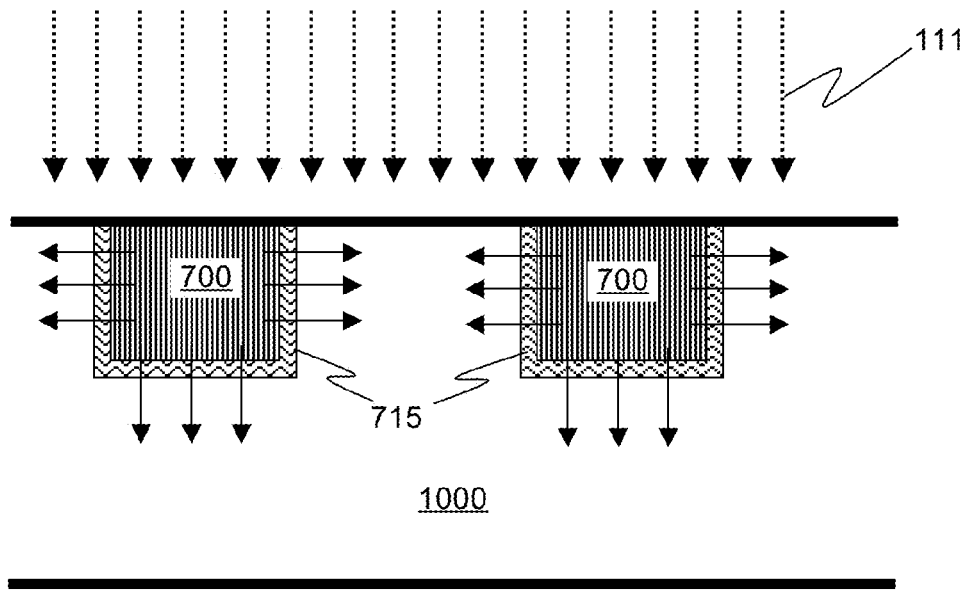
FIG. 34 illustrates a cross-section view of another variation of the target of FIGS. 28A-C and/or FIGS. 29A-C comprising an adhesion layer according to the invention.

FIG. 34 illustrates an alternative example of a target that may be used in embodiments of the invention in which the cavities formed in the substrate 1000 are first coated with an adhesion layer 715 (preferably of minimal thickness) before embedding the x-ray generating material that forms the microstructures 700. Such an adhesion layer may be appropriate in cases where the bond between the x-ray material and the substrate material is weak. The adhesion layer may also act as a buffer layer when the difference between thermal expansion coefficients for the two materials is large. For some choices of materials, the adhesion layer may be replaced or extended (by adding another layer) with a diffusion barrier layer to prevent the diffusion of material from the microstructures into the substrate material (or vice versa). For embodiments in which an adhesion and/or diffusion barrier layer is used, the selection of materials and thicknesses should consider the thermal properties of the layer as well, such that heat flow from the microstructures 700 to the substrate 1000 is not significantly impeded or insulated by the presence of the adhesion layer 715.

Figure 35:
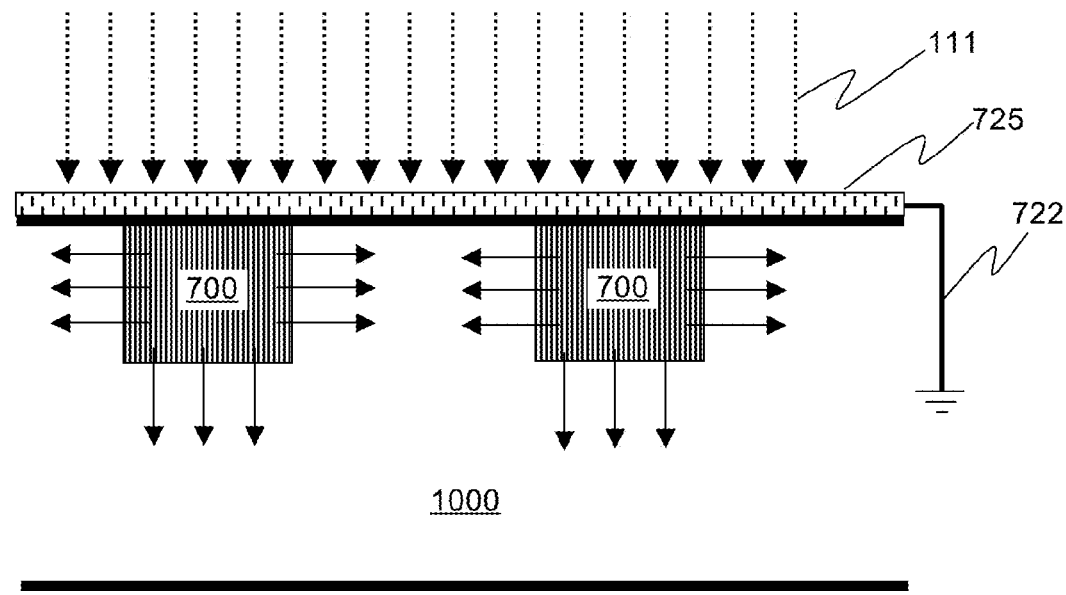
FIG. 35 illustrates a cross-section view of another variation of the target of FIGS. 28A-C and/or FIGS. 29A-C comprising an electrically conducting overcoat according to the invention.

FIG. 35 illustrates an alternative example of a target that may be used in an embodiment in which an electrically conducting layer 725 has been added to the surface of the target. When bombarded by electrons, the excess charge needs a path to return to ground for the target to function effectively as an anode. If the target as illustrated in FIGS. 28 and 29 were to comprise only discrete, unconnected microstructures 700 within an electrically insulating substrate material (such as undoped diamond), under continued electron bombardment, significant charge would build up on the surface. The electrons from the cathode would then not collide with the target with the same energy, or might even be repelled, diminishing the generation of x-rays.

This can be addressed by the deposition of a thin layer of conducting material that is preferably of relatively low atomic number, such as aluminum (Al), beryllium (Be), carbon (C), chromium (Cr) or titanium (Ti), that allows electrical conduction from the discrete microstructures 700 to an electrical path 722 that connects to a positive terminal relative to the high voltage supply. This terminal as a practical matter is typically the electrical ground of the system, while the cathode electron source is supplied with a negative high voltage.

Figure 36:
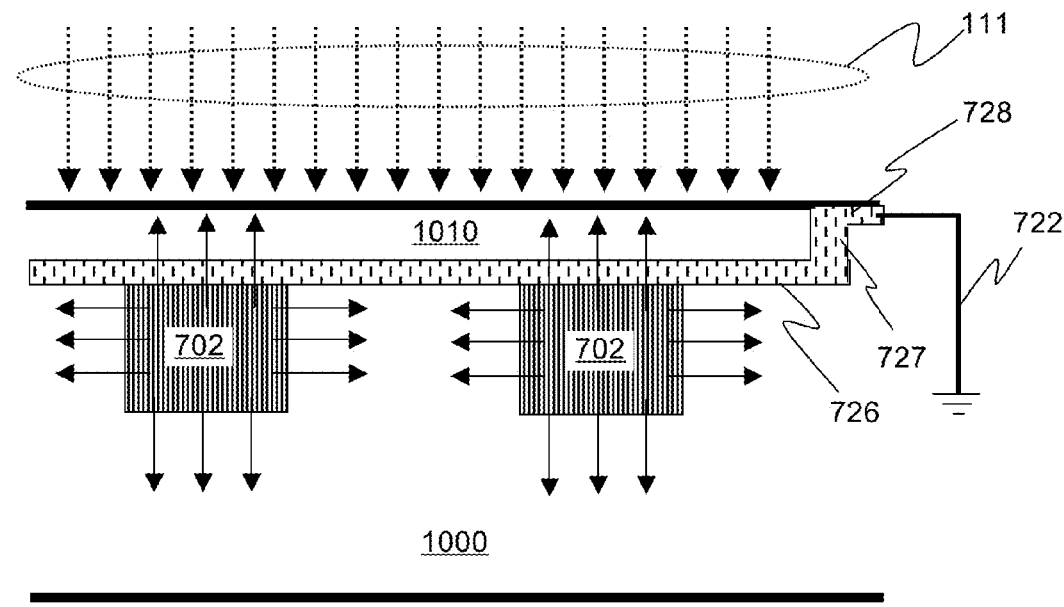
FIG. 36 illustrates a cross-section view of another variation of the target of FIGS. 28A-C and/or FIGS. 29A-C comprising buried x-ray material according to the invention.

FIG. 36 illustrates another example of a target that may be used in an embodiment of the invention, in which the sub-sources 702 are embedded deeper, or buried, into the substrate 1000. Such an embedded microstructure may be further covered by the deposition of an additional layer 1010, which may be, for example, diamond, providing the same heat transfer properties as the substrate. This allows heat to be conducted away from all sides of the buried sub-source 702. For such a situation and when the additional layer 1010 does not have sufficient electrical conductivity, it is advisable to provide a path 722 to ground for the electrons incident on the structure, which may be in the form of an embedded conducting layer 726 laid down before the deposition of the additional layer 1010. In some embodiments, this conducting layer 726 will have a "via" 727, or a vertical connection, often in the form of a pillar or cylinder, that provides an electrically conducting structure to link the embedded conducting layer 726 to an additional conducting layer 728 on the surface of the target, which in turn is connected to the path 722 to ground, or the high voltage supply.

Figure 37:
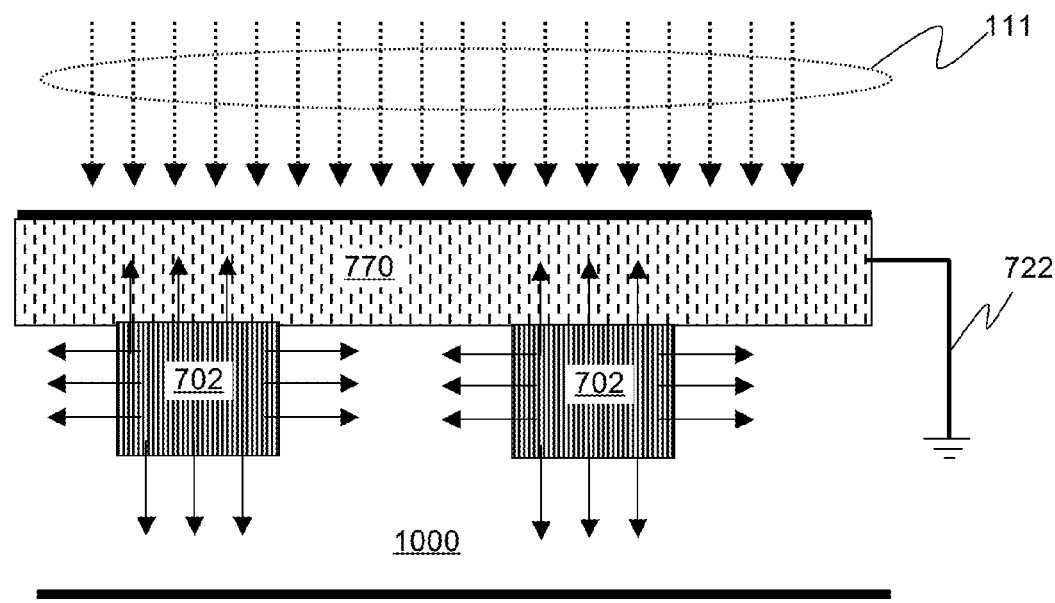
FIG. 37 illustrates a cross-section view of another variation of the target of FIGS. 28A-C and/or FIGS. 29A-C comprising buried x-ray material and a thick thermally and electrically conducting overcoat according to the invention.

FIG. 37 illustrates another example of a target that may be used in embodiments of the invention, in which the sub-sources 702 are again buried within the substrate. However, in this embodiment, instead of first providing an electrically conducting layer followed by the deposition of an additional cap layer, in this embodiment only a single layer 770 is deposited, selected for a combination of electrical properties and thermally conducting properties. This may be, for example, a deposition of carbon nanotubes (Z=6) oriented vertically relative to the surface, such that they conduct both heat and electrons away from the buried microstructures 702. This single layer 770 may in turn be connected to a path 722 to ground to allow the target to serve as an anode in the x-ray generation system. Alternatively, the material of the layer 770 may be selected to comprise aluminum (Al), beryllium (Be), chromium (Cr), or copper (Cu).

Figure 38:
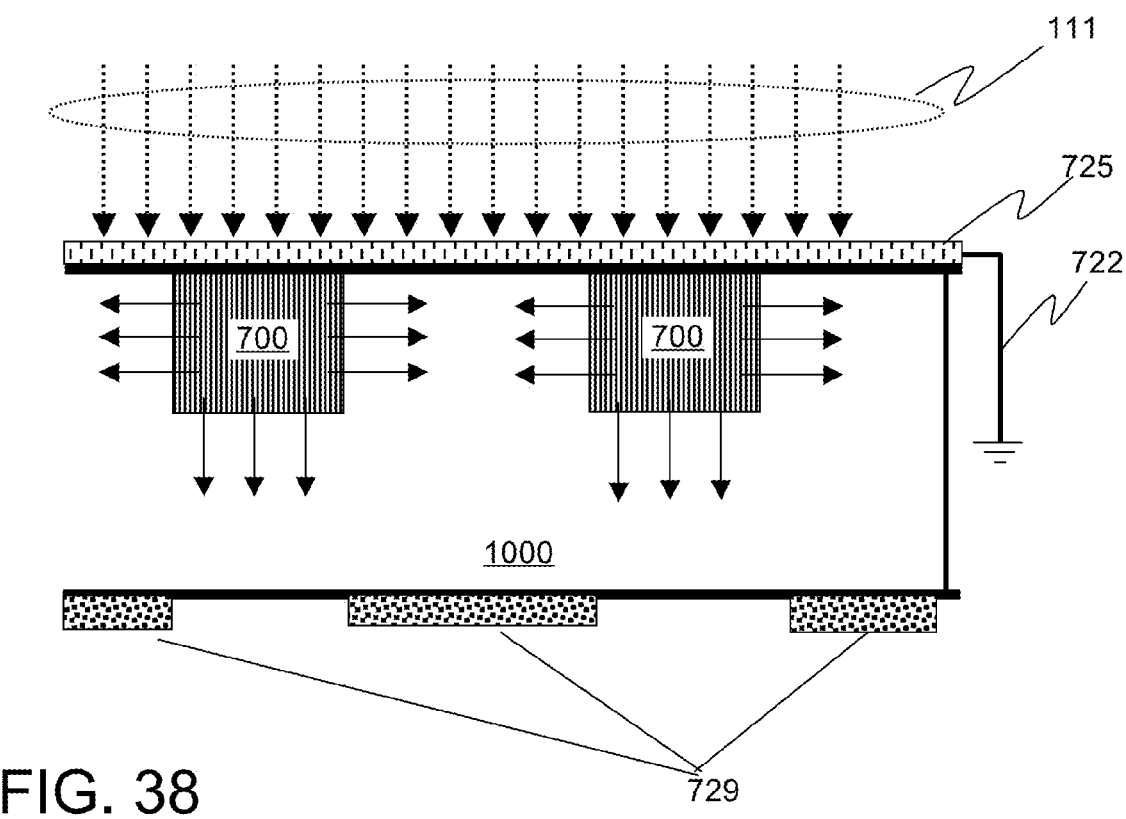
FIG. 38 illustrates a cross-section view of another variation of the target of FIGS. 28A-C and/or FIGS. 29A-C comprising an additional blocking structures on the back surface of the substrate, to block the transmission of x-rays produced by the substrate.
Figure 39:
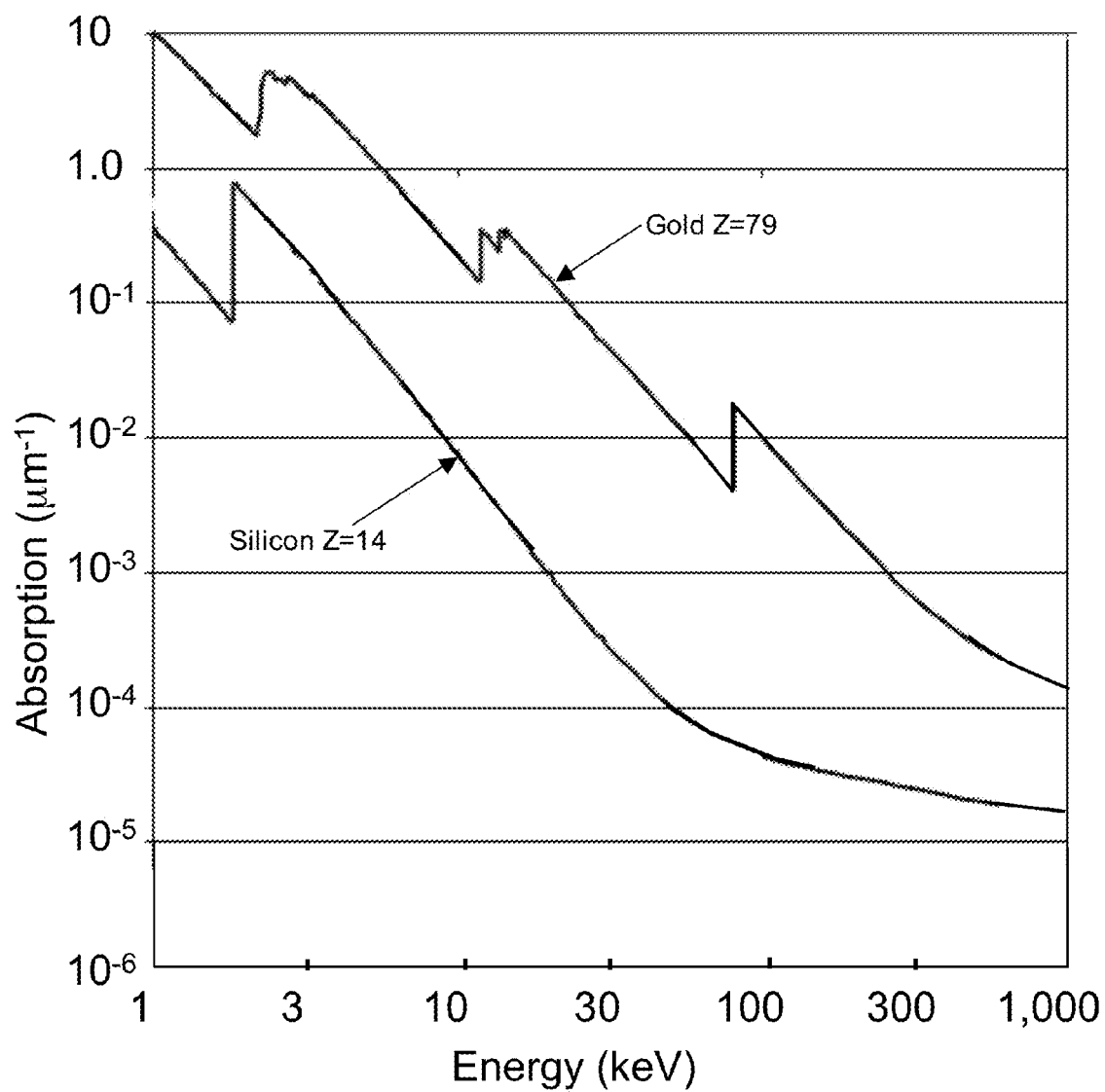
FIG. 39 illustrates a plot of the x-ray absorption of gold and silicon as a function of x-ray energy.

FIG. 38 illustrates another variation of an embodiment, in which additional patterns of blocking material 729 have been deposited on the backside of the target substrate 1000. If the figure of merit for the selected material combination, as discussed above in Table II, is not large, there may still be significant x-rays generated by the substrate that will reduce contrast in the image. These substrate-generated x-rays can be blocked by a deposition of a suitable material, such as gold, as blocking structures 729. Gold (Z=79) has a strong x-ray absorption, as illustrated in FIG. 39. Processes to deposit these blocking structures may comprise standard deposition processes, and an alignment step may be needed to ensure alignment with the x-ray generating structures on the opposite side.

It should be clear to those skilled in the art that although several embodiments have been presented separately in FIGS. 26-38, and various processes for their manufacture will be presented later, the elements of these embodiments may be combined with each other, or combined with other commonly known target fabrication methods known in the art. For example, the buried sub-sources 702 of FIG. 37 may also comprise multiple grains of microstructures, as was illustrated in FIGS. 30 and 31. Likewise, the adhesion layer 715 as illustrated in FIG. 34 may also be applied to fabrication of embedded sub-sources 700 as shown in FIG. 35. The separation of these alternatives is for illustration only, and is not meant to be limiting for any particular process.

Although the sub-sources illustrated in FIGS. 26-38 have been shown as regularly spaced patterns with uniform size and shape, a regular pattern of sub-sources having non-uniform size and shape, can also be used in some embodiments of the invention. Additionally, each sub-source within a regular periodic pattern may further be comprised of multiple smaller microstructures of non-uniform sizes and shapes. These smaller microstructures may be non-regular and do not necessarily need to have similar x-ray emission characteristics or strength, so as long as the larger sub-sources that each group of microstructures comprise are periodic in nature.

Likewise, although some embodiments have been described with microstructures in, for example, the shape of right rectangular prisms, fabrication processes may create structures that have walls at angles other than 90°, or do not have corners that are exactly right angles, but may be rounded or beveled or undercut, depending on the artifacts of the specific process used. Embodiments in which the microstructures are essentially similar with the shapes described herein will be understood by those skilled in the art to be disclosed, even if process artifacts lead to some deviation from the shapes as illustrated or described.

In other embodiments of the system, a periodic attenuating grating $G_0$ such as are used in the prior art Talbot-Lau interferometers may also be used in conjunction with the source of the invention, so that the x-rays produced by the substrate material surrounding the sub-sources are further attenuated, allowing greater monochromaticity and therefore higher spatial coherence for the source. The apertures of the grating should be coincident with projections of the microstructured x-ray sub-sources, or may, in some embodiments, be placed at a Talbot fractional or integer distance downstream of the source and with the apertures coincident with the source self-images. It is preferable that the grating $G_0$ is of high atomic number and relatively low aspect ratio, for ease of manufacturability.

3. Additional Embodiments

3.1. An Additional Absorption Grid

Additional embodiments may comprise an additional absorption grid, with features and placement designed to reduce scattered radiation (such as Compton scattering and elastic scattering from fine structures with dimensions substantially smaller than the resolution of an imaging system) that contributes to the background in x-ray imaging and reduction of image contrast in many x-ray imaging techniques, including the various embodiments discussed above or various x-ray absorption imaging techniques. The ratio of the intensity of the scattered radiation to the intensity of the primary radiation used forming the images is particularly significant in imaging examinations where a large quantity of scatter is created, e.g., those involving a large volume of tissue being irradiated and those requiring high energy x-rays, thus limiting the efficacy of disease diagnosis for obese patients or for dense body parts (e.g. craniofacial, dense breast tissue, etc.). Current art in antiscattering grids typically comprise high radiation absorption septa (typically fabricated using high Z materials like lead) interlaced with a medium with high radiation transmission (such as aluminum or fiber material). It is typically specified by the grid ratio (ratio of the height of the structures and the interspacing between them), period, and septum width. Use of an antiscattering grid, however, requires a greater radiation exposure to the patient as a fraction of primary beam is also attenuated by the septa.

A common drawback for existing antiscattering grids is that the septa also absorb the useful primary x-rays transmitted through the object, resulting in an undesirable reduction of the image signal and therefore an increased radiation dose to the sample or patient.

The embodiments of the invention as previously disclosed above may also be augmented by the use of an antiscattering grid having a pattern of septa determined by specific imaging setup designed to use the Talbot effect. One embodiment of the invention comprises an antiscattering grid positioned between the beam splitting grating $G_1$ and the detector. The period of the grid spacing and the position may be determined so that the septa are at positions that should be the nodes in the Talbot carpet. The antiscattering grid preferably absorbs the scattered radiation while permitting efficient transmission of the primary radiation, resulting in reduction of background noise and increase in image contrast. The antiscattering grid may comprise simple 1-D structures for the septa, but may also be designed to have 2-D or even 3-D structures tuned to the Talbot interference pattern with which they are intended to be used.

Figure 40:
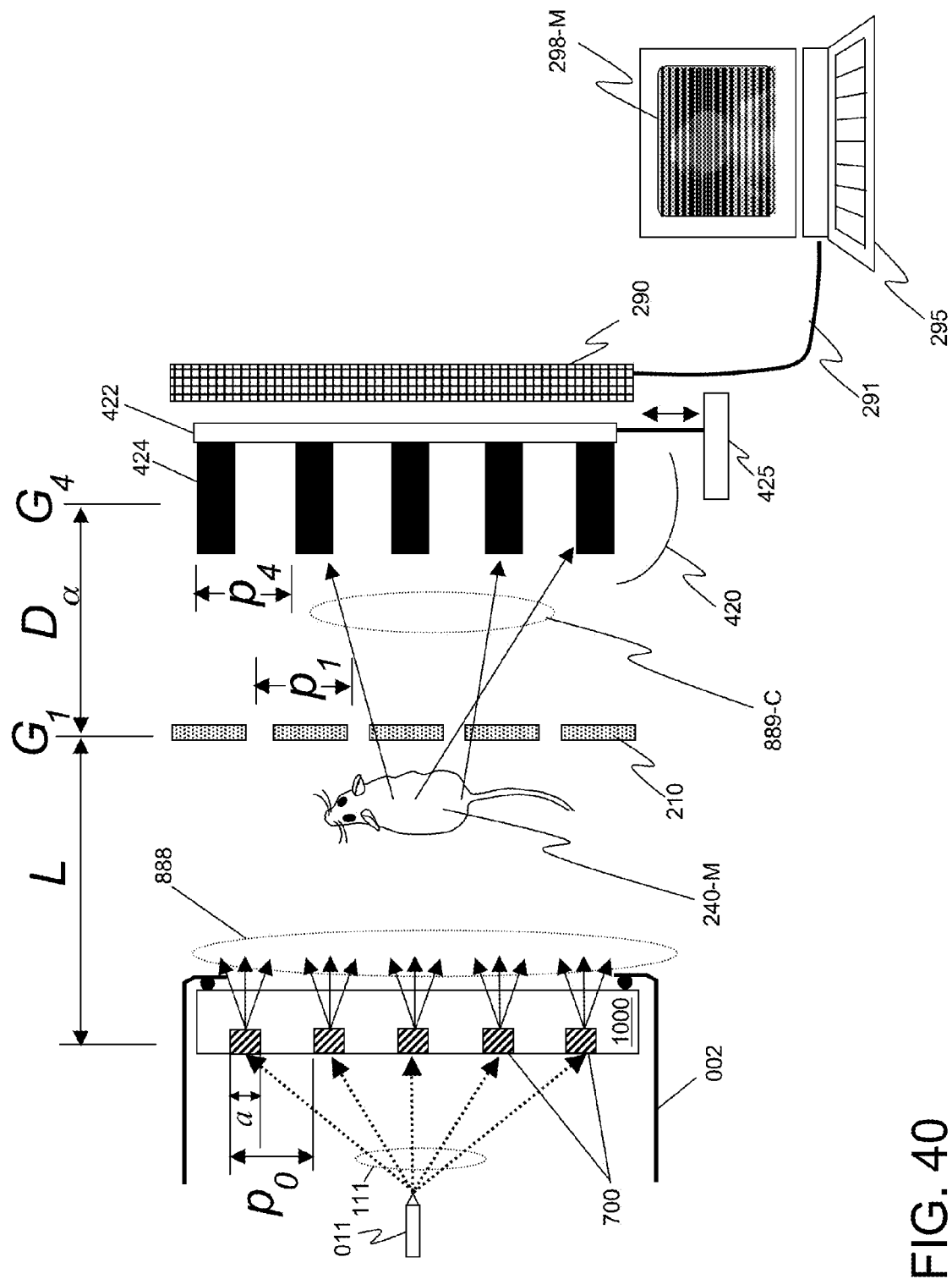
FIG. 40 illustrates a detailed schematic cross-section view for an embodiment of the invention in which an additional antiscattering grating is used.

An embodiment of the invention incorporating an antiscattering grid is illustrated in FIG. 40. As in the other embodiments illustrated in this disclosure, x-rays 888 are generated from microstructured regions 700 comprising x-ray generating material upon bombardment with an electron beam 111. The generated x-rays are transmitted through a sample, in this case a mouse 240-M, and the transmitted x-rays are detected on a detector 290. However, in passing through the mouse 240-M, Compton scattering and other undesired scattering phenomena may occur, producing x-rays 889-C that may propagate at many different angles and reduce the absorption image contrast.

The insertion of an anti-scatter grid 420 helps to attenuate the scattered x-rays, while passing the majority of the x-rays that contribute to image formation. Here, the antiscattering grid 420, designated as $G_4$, is positioned at a distance $D_\alpha$ from the beam splitting grating 210, designated as $G_1$. The antiscattering grid 420 will typically comprise a substrate 422 that is made from a material mostly transparent to x-rays (such as aluminum or a carbon fiber material), upon which a number of absorbing structures 424 comprising material that absorbs x-rays, such as gold, tin, platinum, tungsten, tantalum, nickel, lead, copper, gadolinium, or some other high Z material, have been arranged in a periodic manner. The thickness of the absorbing structures 424 is determined by the X-ray imaging energy which is in turn determined by application; for example, for imaging at 40 keV of infants, the thickness of such structures may be on the order of several hundred microns for lead. In some embodiments, the substrate and absorbing structures may both be fabricated from a single wafer or block of high Z material. The space between the absorbing structures 424 may comprise only air, or may have another low Z material deposited therein. In such embodiments, the distance $D_\alpha$ from the beam splitting grating $G_1$ will be set such that the position is at one of the fractional Talbot distances, i.e.

$$D_\alpha = D_N = N \frac{p_1^2}{8\lambda} = \frac{N}{16} D_T \qquad \text{[Eqn. 15]}$$

where $D_N$ is the fractional Talbot distance for a plane wave illumination, $\lambda$ is the mean x-ray wavelength, and N is referred to as a Talbot fractional order.

The period of the structures in the antiscattering grid may be set to be $$p_4 = K p_0 \frac{D_\alpha}{L} \qquad \text{[Eqn. 16]}$$

where $p_0$ is the period of the microstructured source, L the distance between the x-ray sources 700 and the beam splitting grating 210, and K is a scaling factor which is equal to 1 when the beam-splitting grating introduces a phase shift of $\pi/2$, and is equal to ½ when the beam-splitting grating introduces a phase shift of $\pi$.

The antiscattering grid may be a 1-D grating, or a 2-D grating, with the periods in the x and y axes corresponding using Eqn. 16 above with the corresponding (e.g., horizontal and vertical) periods in the beam splitting grating. In some embodiments, the absorbing septa will be arranged with an aspect ratio of >5:1, i.e. with features 5 times or more higher than the width of the gap between features, and the normal-incidence transmission of the absorbing regions will be less than 10%. Septa may be designed such that the ratio of the area of the septa to the total area ranges from 20-50%. The position may be controlled by a controller 425 that may allow the antiscattering septa to be aligned with the interference fringes formed by the beam splitting grating 210.

Some scattered x-rays may still propagate at angles and in directions that allow it to be transmitted through the apertures in the antiscattering grid. However, by placing the antiscattering grid such that the absorbing structures are co-positioned with the nodes of the Talbot fringe pattern, nearly 100% of the Talbot fringe pattern may be transmitted, while 50% to 75% or more of the scattered x-rays may be absorbed. In some embodiments, the absorbing structures are not matched to each node but may instead be matched to integer multiples of the nodes.

Further reduction in scattered x-rays may be achieved by including a second antiscattering grid. This second grid may be placed at the same Talbot distance in close proximity to the first antiscattering grating, effectively increasing the absorption and aspect ratio of the features, or it may be positioned at another Talbot distance using the same design consideration as discussed in the previous embodiments.

Figure 41:
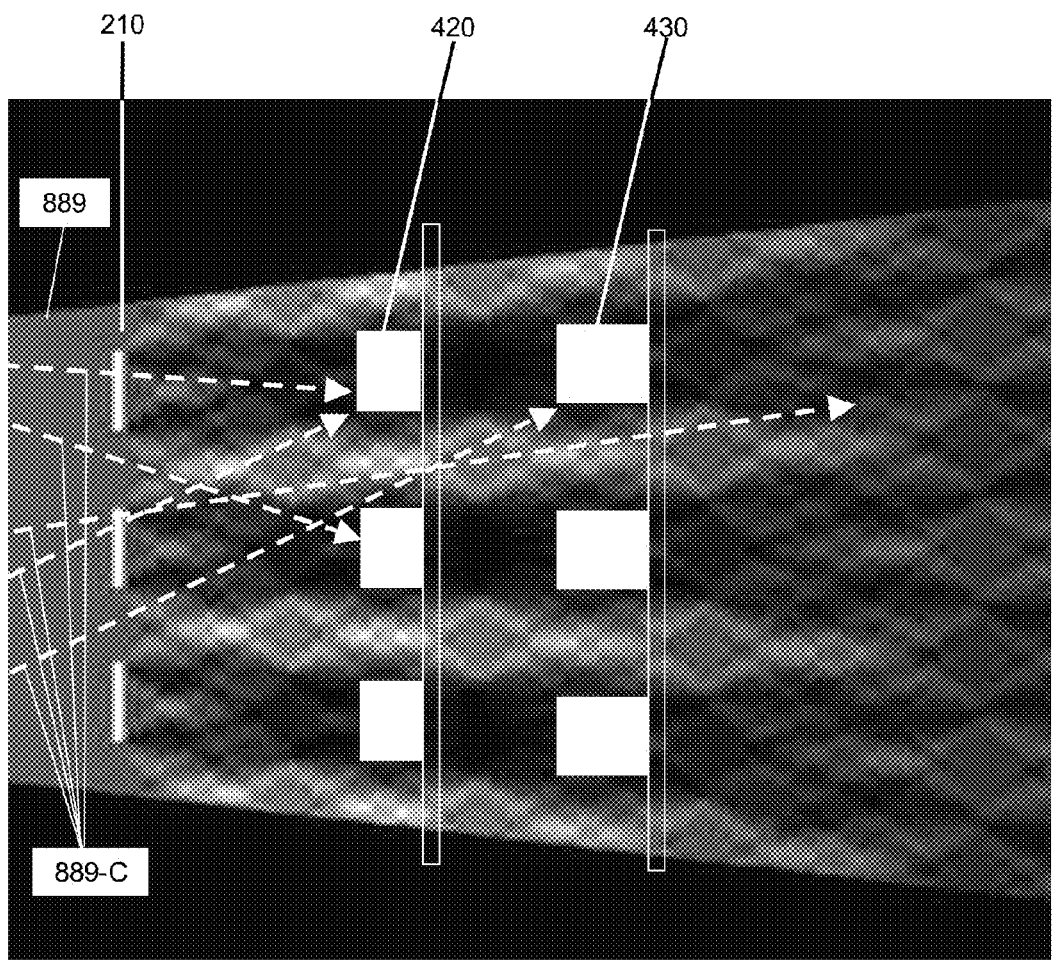
FIG. 41 illustrates a cross-section of the placement of antiscattering gratings within a Talbot interference pattern.

FIG. 41 illustrates the placement of two antiscattering grids in the Talbot image of a phase grating. The Talbot pattern as illustrated corresponds to a 1:1 $\pi/2$ phase grating, as has been previously presented in references such as "X-Ray Phase Imaging withTalbot Interferometry" by A Momose et al. in *BIOMEDICAL MATHEMATICS: Promising Directions in Imaging, Therapy Planning, and Inverse Problems* (Medical Physics Publishing, Madison Wis., 2010), pp. 281-320.

The x-rays 889 transmitted through a sample enter from the left and fall onto the 1:1 $\pi/2$ phase grating 210. Under spatially coherent illumination, the grating produces a Talbot carpet, as discussed in the previous embodiments. At the third fractional Talbot distance (N=3), an absorption grating 420 is placed and positioned so that the absorbing features, designated by a set of white boxes denoting x-ray blocking material in FIG. 41, are aligned with the nodes of the Talbot carpet. At the fifth fractional Talbot distance (N=5), another absorption grating 430 is placed and positioned so that the absorbing features, designated by a set of white boxes denoting x-ray blocking material in FIG. 41, are aligned with the nodes of the Talbot carpet. Scattered x-rays 889-C, illustrated by white arrows, will mostly be blocked by these absorption gratings 420 and 430, while the intensity of the Talbot pattern remains relatively unchanged. It should be noted that the formation of Talbot carpet as illustrated corresponds to one in which the beam splitting grating is illuminated with x-rays having sufficient spatial coherence.

The designs and patterns on the antiscattering grids will correspond to the patterns fabricated into the beam splitting gratings. For example, if the mesh pattern of FIG. 17 is used as the beam splitting grating $G_1$, the antiscattering grid may also be arranged in a mesh pattern. If the checkerboard pattern of FIG. 18 is used as the beam splitting grating $G_1$, the antiscattering grid may also be arranged in a checkerboard pattern. Or, if the checkerboard pattern of FIG. 18 is rotated 45° to form a diamond pattern, the antiscattering grid may also be arranged in a rotated checkerboard (diamond) pattern. Additional embodiments may further include other periodic structures such as honeycomb structures.

Figure 42:
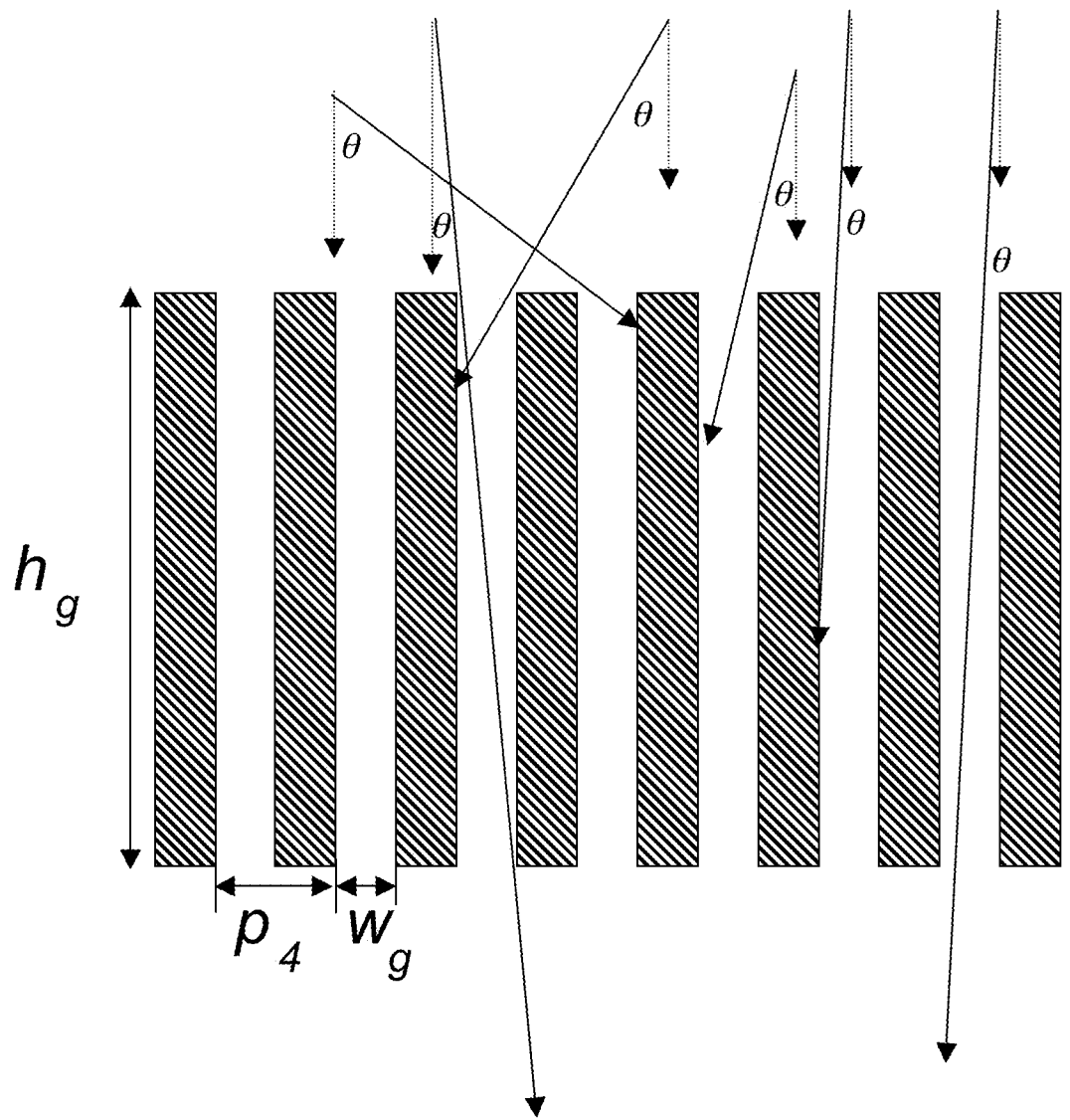
FIG. 42 illustrates a schematic cross-section of an antiscattering grating.

The transmission through the antiscattering grid is a function of the aspect ratio and the relative size of the absorbing features. This is illustrated in FIG. 42. The height of the grating is given by $h_g$, while the width of the apertures between absorbing structures is $w_g$ and the period of the antiscatter grating is $p_4$. Scattered x-rays with a propagation angle $\theta$ from normal such that $$\tan(\theta) < (w_g/h_g) \quad \text{[Eqn. 17]}$$

will generally pass through the grid if they happen to not hit one of the absorbing structures end on. Transmission for normal incidence x-rays will be given by the ratio of the area of absorbing and non-absorbing structures. For the case of a 50/50 grid, where $p_4 = 2w_g$, the best transmission will be 50%. In this case, the transmission of scatter ration at small scattering angles with respect to the primary radiation is the same as the primary radiation, there is not preferential absorption of the scatter radiation. For scatter radiation with scattering angles greater than $$\theta = \tan^{-1}(w_g/h_g) \quad \text{[Eqn. 18]}$$

the antiscattering grid preferentially absorbs scatter radiation.

Figure 43:
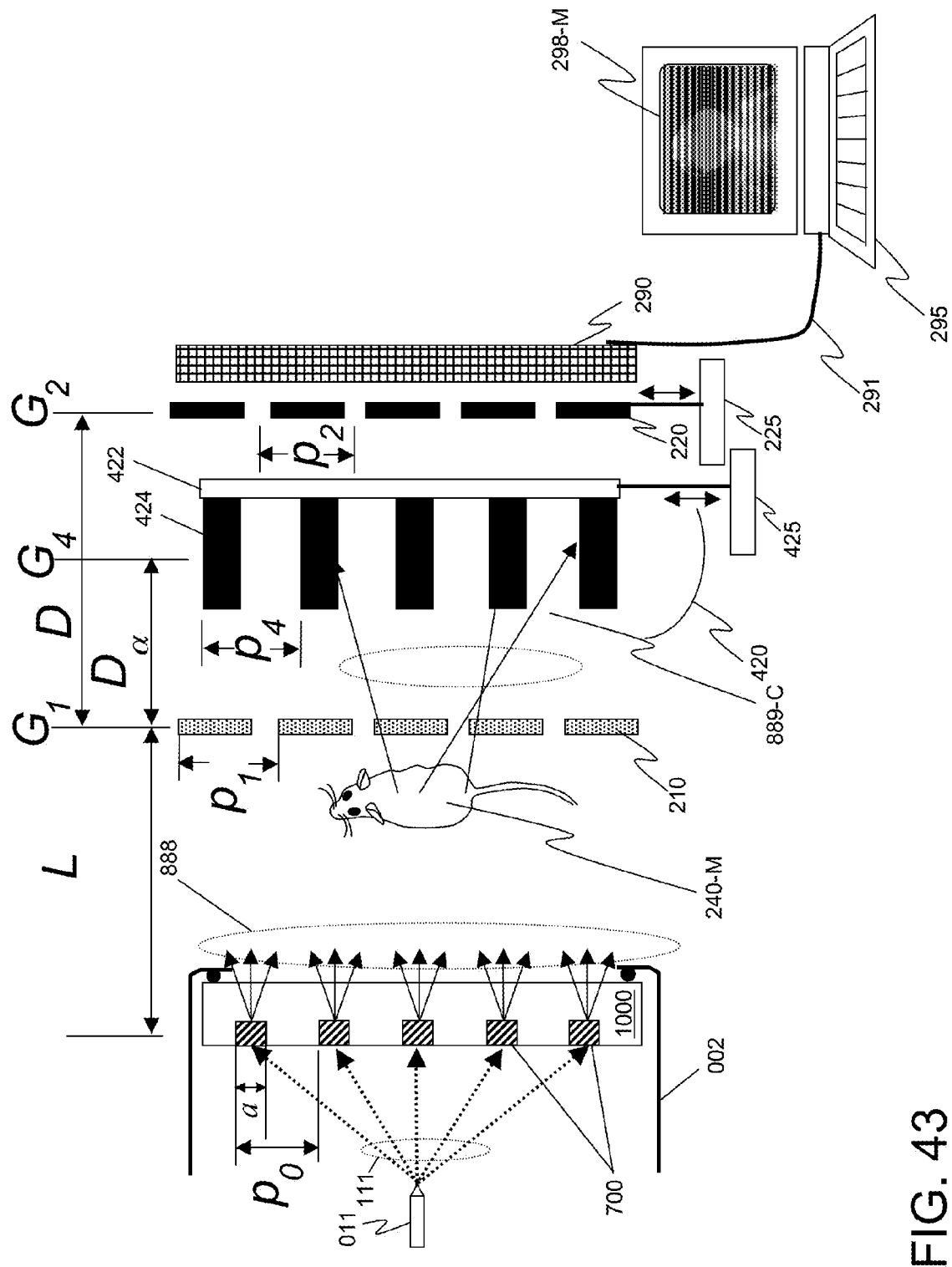
FIG. 43 illustrates a detailed schematic cross-section view for an embodiment of the invention in which an additional antiscattering grating is used along with an analyzer grating at the detector.

In some embodiments, the antiscattering grid may be used in addition to an analyzer grating $G_2$ for the detector. Such an embodiment is illustrated in FIG. 43. Using such a configuration, multiple embodiments of the invention enable one to obtain additional information about the sample.

The embodiment as illustrated in FIG. 43 comprises an x-ray source 002 with microstructured periodic array sub-sources as disclosed in various embodiments, a beam splitting grating $G_1$ 210, an antiscattering grid $G_4$ 420, and a detector 290, without the analyzer grating $G_2$. In absence of the beam splitting grating 210 and the antiscattering grid 420, this imaging system is similar to most conventional x-ray imaging systems, except for the microstructured x-ray source 002, which is usually an extended x-ray source. The current art of antiscattering grid is ineffective for absorbing scattered radiation with small scattering angles with respect to the primary radiation because it has a significant fraction of the area that are transparent to both the scatter radiation and primary radiation. This becomes particularly significant for observing subjects such as babies or uncompressed breasts, in which scattering such as Compton scattering can be 5× greater than the signal carrying absorption contrast information. According to embodiments of the invention, scattered radiation can be preferentially absorbed by placing the antiscattering grid at one of the fractional Talbot distances and positioning the absorbing features at the nodes of the corresponding Talbot carpet. This embodiment is particularly important for imaging objects having large volume using high energy x-rays, such as clinical x-ray imaging and security inspection.

According to another embodiment of the invention, a dark-field image may be recorded by the detector 290 without the analyzer grating 220 by placing the antiscattering grid 420 at one of the fractional Talbot distances and positioning the absorbing features at the antinodes (or integer multiples of the antinodes) of the corresponding Talbot carpet. Another dark-field image can be recorded by the detector 290 without the absorption grid 420 but with the analyzer grating 220 aligned so that its absorbing parts are aligned to the antinodes of the Talbot carpet. Because two different dark-field images are obtained at different distances from the beam splitting grating 210, they will contain different spatial information about the object.

According to another embodiment of the invention, by placing an antiscattering grid at one of the fractional Talbot distances and positioning its absorbing features at the nodes of the corresponding Talbot carpet, several established phase contrast imaging techniques usually done without the antiscattering grid can be used, including differential phase contrast imaging, phase stepping to obtain simultaneous phase, absorption, and scattering images, and imaging using a high spatial resolution detector without phase stepping.

3.2. Detector MTF and DQE

Variations in the detector configuration and positioning may also contribute to improvements in the signal-to-noise ratio for x-ray systems constructed according to the invention. The figures of merit that may be impacted by the selection of detector properties are the modulation transfer function (MTF) and the detection quantum efficiency (DQE).

The presence of Compton scattering, as described above, may contribute to the degradation of these figures of merit. However, other factors may also impact MTF and DQE. The achievable MTF and DQE of a detector depend on different physical processes. The intrinsic physical processes to all x-ray array detectors include the interaction (traveling) range of the photoelectrons produced by the ionizing radiation, production of secondary x-ray fluorescence produced by the ionization/de-excitation of atoms in the detector sensing material by the incident x-rays, and parallax blurring resulting from the finite thickness of the sensing material at oblique incidence angles with respect to the surface normal. Reabsorption of Compton scattered radiation and secondary fluorescence x-rays by the materials of the detector can also contribute to the reduction of MTF and DQE, but this contribution is usually negligible.

Additional processes in actual detectors may also contribute to the reduction of MTF and DQE. For direct conversion digital array detectors (such as amorphous selenium-photoconductor-based flat panel detector), lateral diffusion of charge carriers may contribute to the reduction of MTF ad DQE. For indirect conversion digital array detectors comprising a layer of a phosphor material (such as $Gd_2O_2S$) ora scintillator material (such as column-grown CsI fibers), light spread due to scattering can contribute significantly to the reduction of the MTF and DQE in the detector.

For all digital array detectors, the fill factor (the percent of the effective detection area) will also contribute to the reduction of MTF and DQE, which can be especially problematic with small detector pixels. For all the factors contributing to the reduction of MTF and DQE, these effects get worse with increasing detector resolution (smaller pixels), and may lead to many design compromises and tradeoffs, including: the compromise between scintillator/phosphor thickness (and, therefore, its quantum detection efficiency); spatial resolution limitations due to light scattering induced image blurring; and considerations and trade-offs between improving resolution (smaller pixels) with detector parameters such as fill factor, material mass density (to which the photoelectron range is inversely proportional), and the elemental composition of the detector sensing material which determines the range of the characteristic fluorescence x-rays.

Most of the detrimental factors to MTF and DQE make a maximum contribution when the radiation is incident near or at the edges of the detector pixels. Thus an improvement in MTF and DQE may be achieved if all the incident radiation is directed to be incident at the center of the detector pixels.

Commonly deployed position-sensitive detectors do not have intrinsic angle sensing/rejection capability. Scattered radiation (including small-angle scattering by fine structures in the object as well as Compton scattering) is part of the undesirable image background, producing "counts" in the detector that are indistinguishable from the "counts" due to the desired radiation.

Therefore, the use of a system comprising a detector that rejects or reduces the scattered radiation can increase the image contrast and the DQE of the system.

3.3. Embodiments with a Modified Detector

As discussed above, the scattered radiation may be blocked by placing an absorption grid or grating aligned such that the absorption regions correspond to the dark Talbot fringes.

Likewise, it is also possible to select the detector grid spacing and positioning so that the centers of the rows (and/or columns) are aligned with the centers of the antinodes of the Talbot fringes, such that the area between sensor pixels (which by definition is made to be transparent to the incident x-rays) correspond to the position of the nodes of the Talbot carpet. By using a detector with such a spacing and alignment, the scattered x-rays that would normally be absorbed by the detector are not absorbed. As a consequence, the noise associated with them in the sensor pixels due to photoelectrons, reabsorption of secondary fluorescence x-rays, and Compton scattering, will be absent, and the signal-to-noise ratio is improved.

Figure 44:
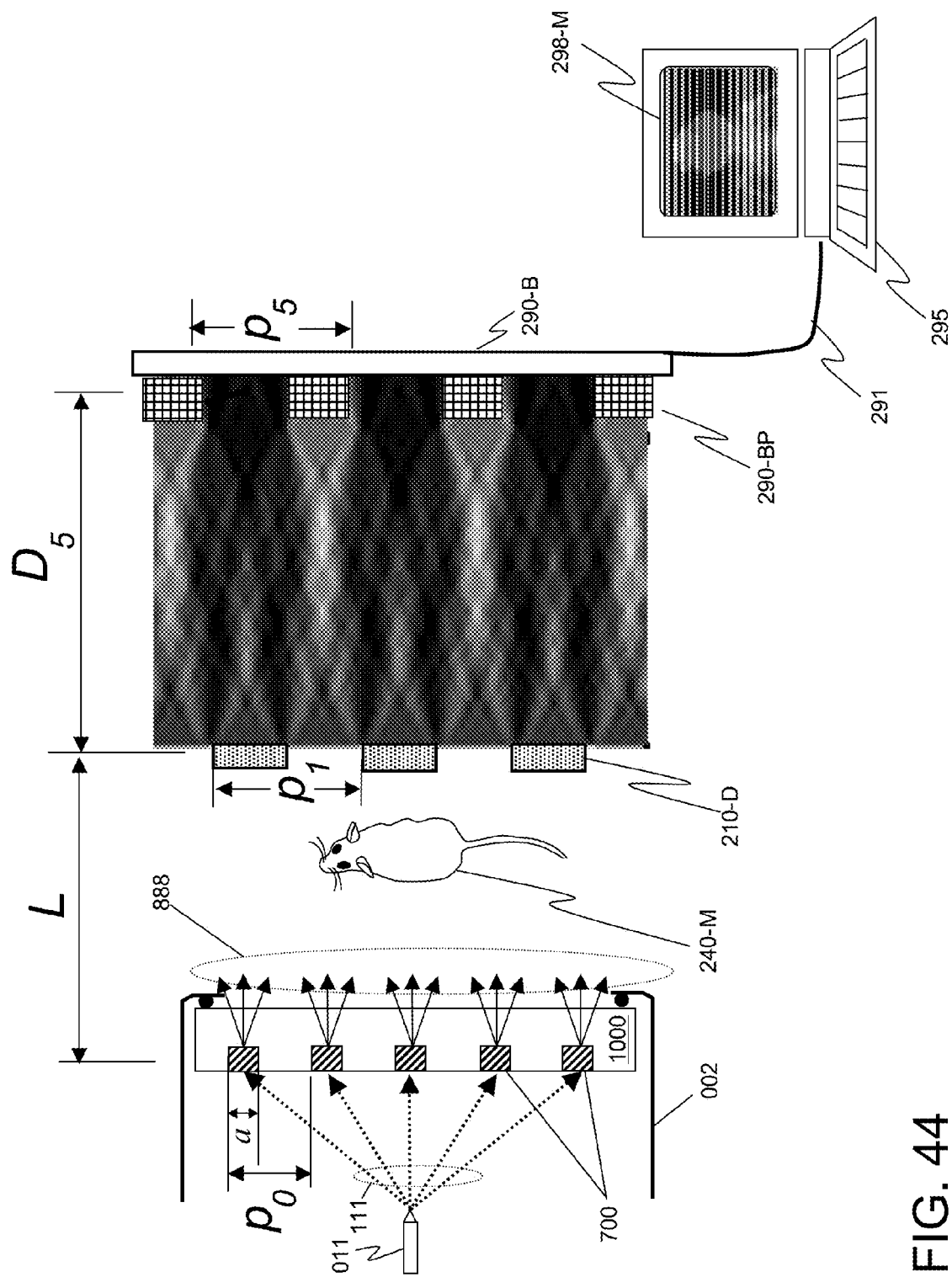
FIG. 44 illustrates a schematic cross-section view for an embodiment of the invention in which the detector elements are aligned with the high intensity portions of the Talbot interference pattern.

FIG. 44 illustrates a system in which the detector is so arranged. As in previous embodiments, the x-rays 888 generated by a source comprising a plurality of microstructured sub-sources 700 arranged in a regular pattern (i.e. a set of lines or an array) generate x-rays that propagate through an object to be examined 240-M and fall onto a beam-splitting grating 210-D. The beam-splitting grating is generally a one- or two-dimensional phase-shifting grating, with spacing and period $p_1$ of the grating having a relationship to the spacing of the sub-sources as described in Eqn. 9 above. The Talbot pattern as illustrated corresponds to a beam splitting grating 210-D having a 1:1 π/2 phase shifting pattern, as illustrated in, for example, "X-Ray Phase Imaging with Single Phase Grating" by Y. Takeda et al., *Jpn. J. Appl. Phys.* vol. 46, 2007, pp. L89-L91.

A detector comprising various sensor pixels 290-BP connected electronic backplane 290-B produces signals related to the number of x-rays detected, and that signal passes through a connector 291 to a data processing system 295 for analysis. The detector is positioned at one of the fractional Talbot distances, i.e.

$$D_S = D_N = N_S \frac{p_1^2}{8\lambda} = \frac{N_S}{16} D_T \qquad [\text{Eqn. 19}]$$

where $D_N$ is the fractional Talbot distance for a plane wave illumination, λ is the mean x-ray wavelength, and $N_S$ is the Talbot fractional order (N=1, 2, 3, . . . ) at which the detector is placed.

The spacing $p_5$ of the sensor pixels is then selected to correspond to the Talbot spacing for the corresponding beam-splitting grating $G_1$. The relationship is given by:

$$p_5 = Kp_0 \frac{D_5}{L} \qquad [\text{Eqn. 20}]$$

where $p_0$ is the period of the microstructured source, L the distance between the x-ray sources 700 and the diffraction grating 210-D, and K is a scaling factor which is equal to 1 when the beam-splitting grating introduces a phase shift of $\pi/2$, and is equal to ½ when the beam-splitting grating introduces a phase shift of $\pi$.

Figure 45:
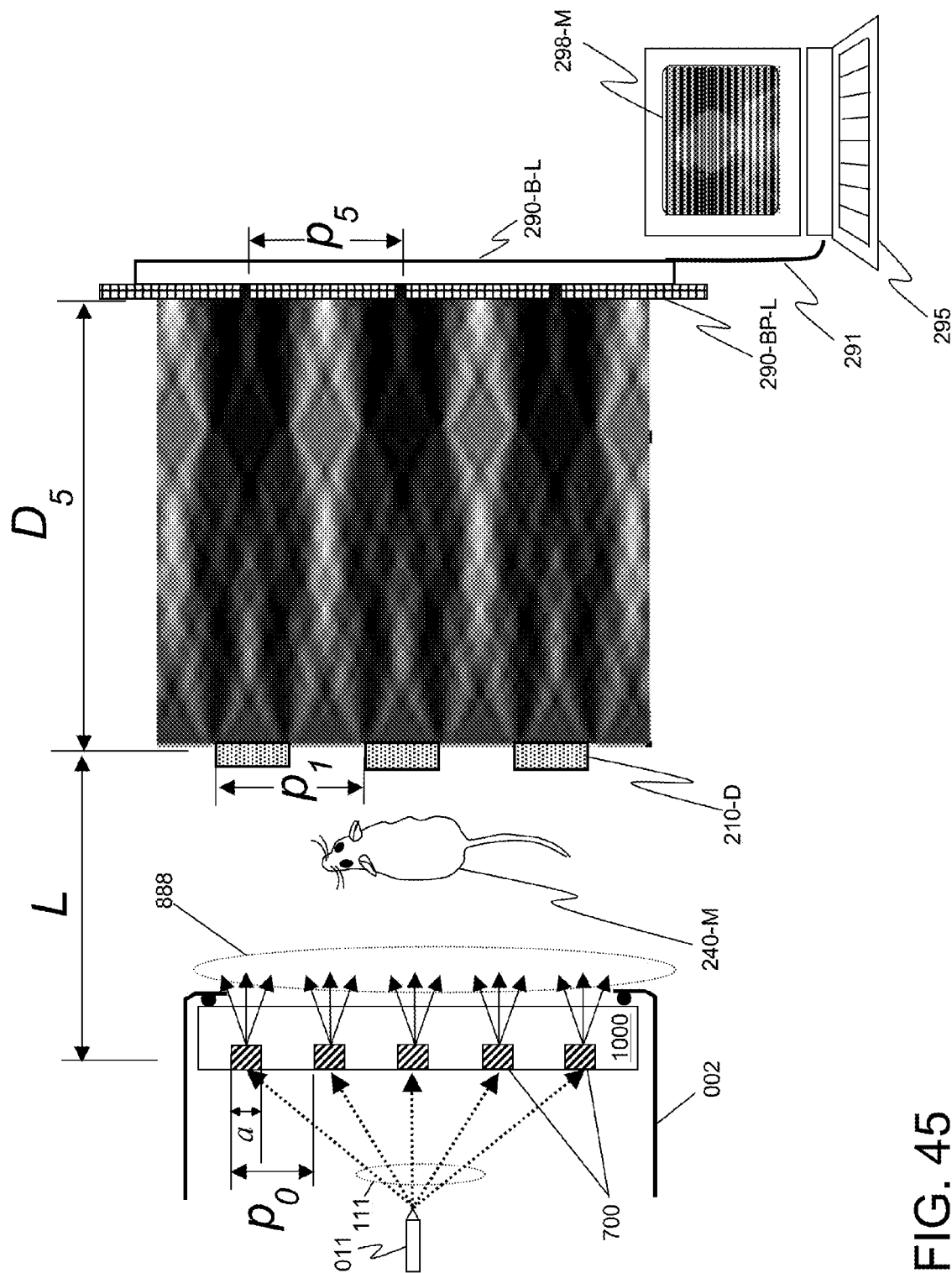
FIG. 45 illustrates a schematic cross-section view for an embodiment of the invention in which a beamsplitting grating is placed upstream of a detector such that the detector elements are aligned with the high intensity (antinodes) of the Talbot interference pattern.

FIG. 45 illustrates another embodiment in which the grating 210-D is used to produce a Talbot interference pattern. The detector 290-B-L comprises pixels 290-BP-L in which the majority of the area of the detector comprises pixels, with only a small gap between pixels. The detector 290-B-L is placed at a predetermined Talbot distance (fractional or odd integer) such that the antinodes (regions of constructive interference) of the Talbot pattern is incident on or near the center of each detector pixel 290-BP-L. Thus the detector has a periodicity that corresponds to the period of the Talbot pattern. Such a grating and detector scheme may be used with the microstructured source previously mentioned, or with any other source with sufficient lateral coherence, such as a microfocus source.

The designs and patterns on the detector grids will correspond to the patterns fabricated into the beam splitting gratings. For example, if the checkerboard pattern of FIG. 18 is used as the beam splitting grating $G_1$, the detector grid may also be arranged in a checkerboard pattern. Or, if the mesh pattern of FIG. 17 is used as the beam splitting grating $G_1$, the detector grid may also be arranged in a mesh pattern. If the checkerboard pattern of FIG. 18 is rotated 45° to form a diamond pattern, the detector grid may also be arranged in a rotated checkerboard (diamond) pattern.

3.4. "Single Shot" Talbot Techniques

Existing x-ray imaging systems for clinical, security inspection, and nondestructive test use primarily absorption contrast (difference in attenuation between neighboring features). It has been long recognized that x-ray phase contrast (difference in phase shift between neighboring features) can be significantly larger than absorption contrast for most materials at high energy x-rays, especially for low Z materials. Recently, scattering contrast (difference in small angle scattering strength between neighboring features) has been recognized for imaging sub-resolution features within an imaging resolution element (such as pores and fine structures of dimension less than the imaging resolution). It is highly desirable to be able to simultaneously obtain in a single shot (exposure) an absorption contrast image in combination with at least one of a differential phase contrast image, phase contrast image, or scattering contrast image.

Several researchers have developed single-shot x-ray phase contrast imaging techniques that use beam splitting gratings and an analyzer grating slightly rotated with respect to the beam splitting grating, and then using a Fourier transform image analysis technique to arrive at a phase contrast image. The drawback of this technique is that the image spatial resolution is substantially compromised. Additional developments include further variants of single-shot techniques [see, for example, H. Wen, E. E. Bennett, M. M. Hegedus, and S. C. Carroll, "Spatial harmonic imaging of X-ray scattering—initial results," *IEEE Trans. Med. Imaging* vol. 27(8), 997-1002 (2008); and H. Wen, E. E. Bennett, M. M. Hegedus, and S. Rapacchi, "Fourier X-ray scattering radiography yields bone structural information," *Radiology* vol. 251(3), 910-918 (2009)], which they called the "spatial harmonic method". In these references, a single projection image containing a transmission grating (grid) will have several distinct harmonic peaks in the spatial frequency domain. Inverse Fourier transformation of these peaks results in harmonic images. The relative weight between absorption and diffraction-caused attenuations differs among these images, and therefore provide sufficient information to extract separate absorption and diffraction images. Raw images obtained by both single-shot techniques do not contain separate absorption and dark-field (scattering) images, and require image analysis to obtain images from different contrast mechanisms.

3.5. Embodiments with Two Modified Detectors (for "Single Shot" Techniques)

In other embodiments of the invention, a system with two detectors, one positioned at one of the fractional Talbot distances and aligned with its grid (active pixels), spacing (transparent areas between the active pixels) and positioning so that the centers of the rows (and/or columns) are aligned with the centers of the antinodes of the Talbot fringes, while the other positioned at another one of the fractional Talbot distance downstream of the first detector and aligned with its grid (active pixels), spacing (areas between the active pixels, preferably transparent) and positioning so that the centers of the rows (and/or columns) are aligned with the centers of the nodes of the Talbot fringes. By using a pair of detectors with such a spacing and alignment, both the absorption and the scattering (dark-field) images may be collected at the same time, in a "single shot". In some embodiments, the positions of the two detectors can be reversed, but the spacing between the active pixels of the upstream detector in this case should still be sufficiently transparent to x-rays.

Figure 46:
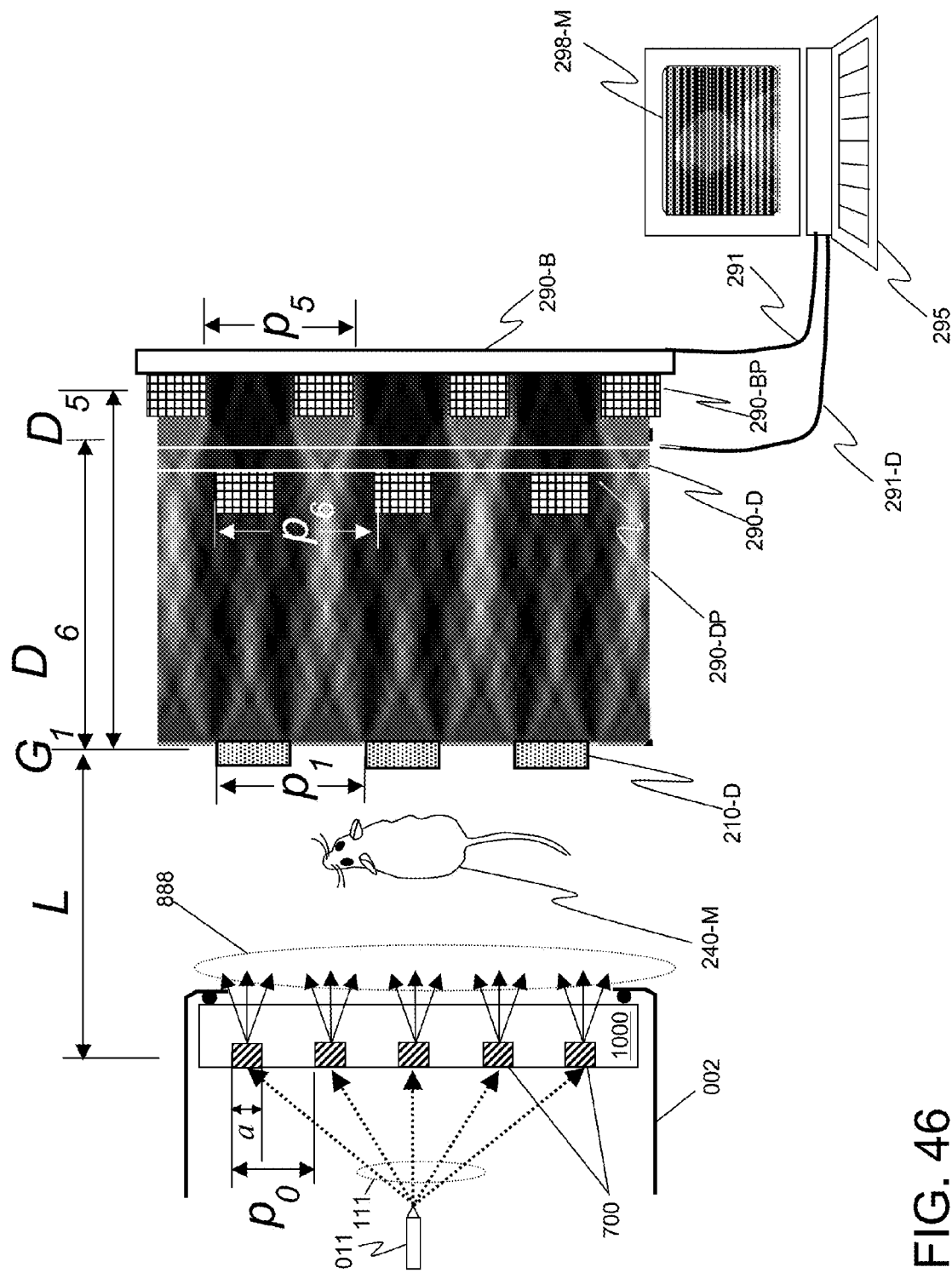
FIG. 46 illustrates a schematic cross-section view for an embodiment of the invention comprising both a bright field and dark field detector.

FIG. 46 illustrates a system in which a pair of detector is so arranged. As in previous embodiments, the x-rays 888 generated by a source comprising a plurality of microstructured sub-sources 700 arranged in a regular pattern (i.e. a set of lines or an array) generate x-rays that propagate through an object to be examined 240-M and fall onto a beam-splitting grating 210-D. The beam-splitting grating is generally a one- or two-dimensional phase-shifting grating, with spacing and period $p_1$ of the grating having a relationship to the spacing of the sub-sources as described in Eqn. 9 above.

One detector comprising various sensor pixels 290-BP connected electronic backplane 290-B produces signals related to the number of x-rays detected, and that signal passes through a connector 291 to a data processing system 295 for analysis. As above, the detector is positioned at one of the fractional Talbot distances, i.e.

$$D_5 = D_N = N_5 \frac{p_1^2}{8\lambda} = \frac{N_5}{16} D_T \qquad [\text{Eqn. 21}]$$

where $D_N$ is the fractional Talbot distance for a plane wave illumination, $\lambda$ is the mean x-ray wavelength, and $N_5$ is the Talbot fractional order (N=1, 2, 3, . . . ) at which the first detector is placed. The active pixels (indicated by the hatched boxes) of the detector 290-BP are aligned with the antinodes of the corresponding Talbot carpet. The areas between the active pixels are preferably transparent, but not necessary.

As above, the spacing $p_5$ of the sensor pixels is then selected to correspond to the Talbot spacing for the corresponding beam-splitting grating $G_1$. The relationship is given by $$p_5 = K p_0 \frac{D_5}{L} \quad \text{[Eqn. 22]}$$

where $p_0$ is the period of the microstructured source, L the distance between the x-ray sources 700 and the diffraction grating 210-D, and K is a scaling factor which is equal to 1 when the beam-splitting grating introduces a phase shift of $\pi/2$, and is equal to ½ when the beam-splitting grating introduces a phase shift of $\pi$.

However, in this embodiment, the system also comprises a second detector comprising various sensor pixels 290-DP connected electronic backplane 290-D that produces signals related to the number of x-rays detected for the dark field, and that signal passes through a connector 291-D to a data processing system 295 for analysis. As above, the detector is positioned at one of the fractional Talbot distances, i.e.

$$D_6 = D_N = N_6 \frac{p_1^2}{8\lambda} = \frac{N_6}{16} D_T \quad \text{[Eqn. 23]}$$

where $D_N$ is the fractional Talbot distance for a plane wave illumination, $\lambda$ is the mean x-ray wavelength, and $N_6$ is the Talbot fractional order (N=1, 2, 3, . . . ) at which the second detector is placed. The active pixels (indicated by the hatched boxes) of the detector 290-DP are aligned with the nodes of the corresponding Talbot carpet. The areas between the active pixels need to be sufficiently transparent to x-rays.

As above, the spacing $p_6$ of the sensor pixels of the second detector is then selected to correspond to the Talbot spacing for the corresponding beam-splitting grating $G_1$. The relationship is given by $$p_6 = K p_0 \frac{D_6}{L} \quad \text{[Eqn. 24]}$$

where $p_0$ is the period of the microstructured source, L the distance between the x-ray sources 700 and the diffraction grating 210-D, and K is a scaling factor which is equal to 1 when the beam-splitting grating introduces a phase shift of $\pi/2$, and is equal to ½ when the beam-splitting grating introduces a phase shift of $\pi$.

The designs and patterns on the detector grids will correspond to the patterns fabricated into the beam splitting gratings. For example, if the checkerboard pattern of FIG. 18 is used as the beam splitting grating $G_1$, the detector grids may also be arranged in a checkerboard pattern. Or, if the mesh pattern of FIG. 17 is used as the beam splitting grating $G_1$, the detector grids may also be arranged in a mesh pattern. If the checkerboard pattern of FIG. 18 is rotated 45° to form a diamond pattern, the detector grids may also be arranged in a rotated checkerboard (diamond) pattern.

With this arrangement, the partially transmitting second detector 290-DP records a dark-field x-ray image due to a combination of scattering contrast (x-rays scattered by small-angle scattering by sub-resolution features) and/or refraction (phase) contrast from sharp features with a large phase gradient, while the first (image) detector 290-BP records an image with a combination of an absorption contrast image and/or a refraction (phase) contrast image from features with a small phase gradient. Alternatively, a partially transmitting grating with reverse property from the preceding partially transmitting grating can be used. In this configuration, the images recorded by the partially transmitting detector and the image detector are reversed compared to the preceding detector arrangement.

The ratio of half of the period of the Talbot interference fringe or pattern to the fractional Talbot distance provides a first angular measure which can be used as an approximate measure for substantial presence of scattered/refracted x-rays in the nodes of the Talbot fringes or pattern. By selecting the Talbot fractional orders for the placement of the partially transmitting detector and the main detector and geometric parameters of the beam splitting grating period, distances between the source, beam splitting grating, and x-ray wavelength, one can optimize sub-resolution feature sizes or desired phase gradient of large features for preferentially higher contrast imaging.

Figure 47:
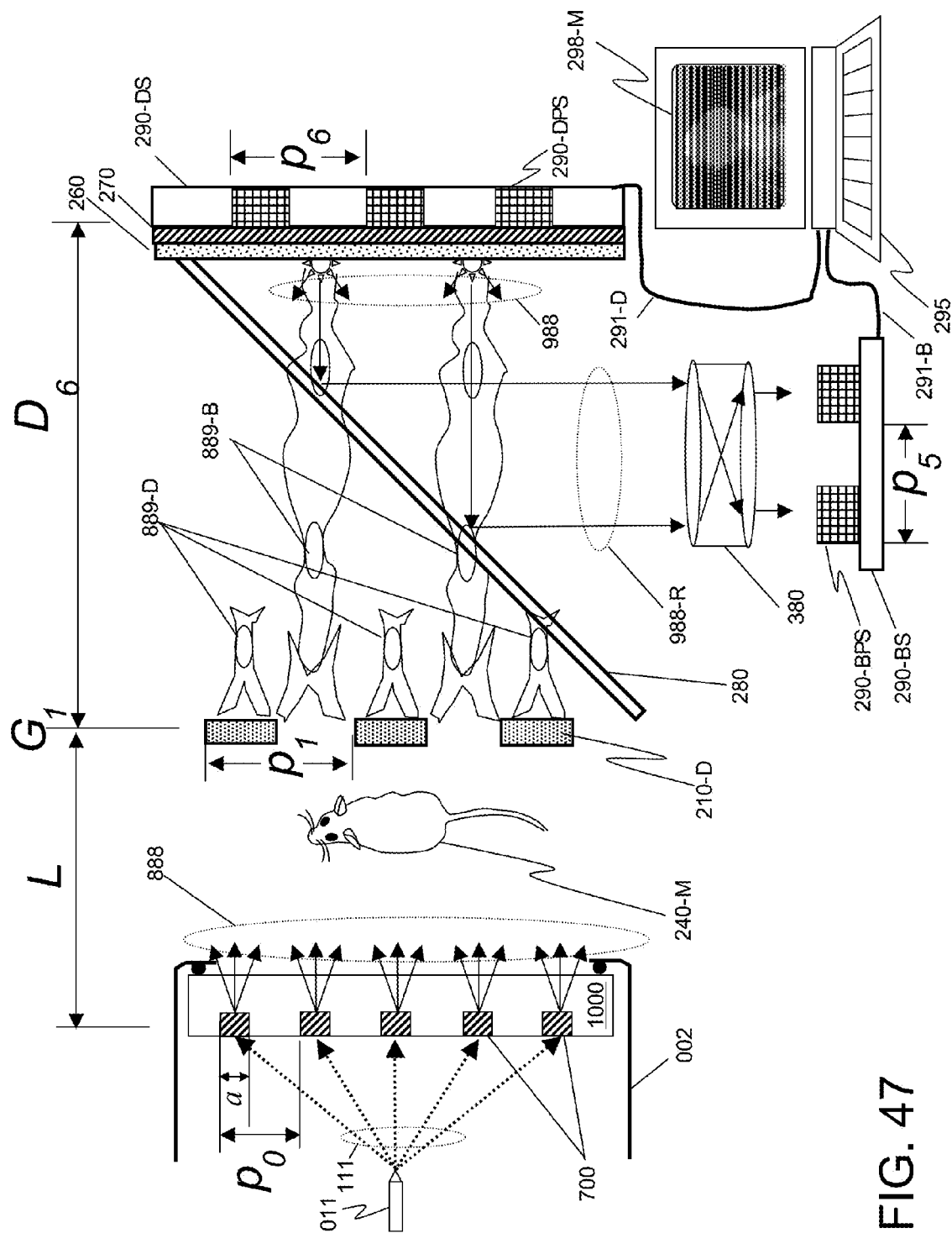
FIG. 47 illustrates a schematic cross-section view for an embodiment of the invention comprising both a bright field and dark field detector, in which a scintillator is used to convert x-rays to visible/UV photons.

An alternative embodiment of a two detector "single shot" system is illustrated in FIG. 47. Here, the bright Talbot Fringes 889-B and dark Talbot regions 889-D are illustrated as propagating away from a beam splitting phase grating with period $p_1$. At a suitable distance away, typically at a multiple of the fractional Talbot distance, a detector 290-DS comprising a scintillator 260 and additionally a reflective coating 270 is placed. The reflective coating is such that the visible light 988 generated when the scintillator absorbs x-rays and emits visible or near UV light is reflected to the scintillator. The detector 290-DS detects the x-rays that are transmitted through the scintillator 260 and the reflector 270, and may additionally comprise sensor pixels 290-DPS that are placed at in a regular array with period $p_6$ such that their positions will correspond to the nodes of the Talbot pattern. This detector 290-DS may in turn produce signals related to the number of x-rays detected in the nodes due to scattering by features with dimensions smaller than the resolution element of the imaging system, and these signals pass through a connector 291-D to a data processing system 295 for analysis.

The scintillator 260 may also be coated in a 1-D or 2-D pattern, so that visible or near UV photons are generated only in regions corresponding to high x-ray intensity (i.e. the antinodes of the Talbot fringes).

The system also comprises a beamsplitter 280 that transmits x-rays but reflects visible and/or UV Photons, and a visible/UV imaging system 380 (e.g. a lens or a microscope objective) that forms an image of the bright field portions of the Talbot interference pattern. The visible/UV photons 998 emitted by the scintillator reflect off this beamsplitter, and the reflected visible/UV photons 988-R are formed into an image by the visible/UV imaging system onto a bright field detector 290-BS. The visible/UV detector may have a uniform array of pixels, or may have selected regions with a period $p_5$ with positions arranged to correspond to the images of the bright field portions of the Talbot pattern. The visible/UV detector 290-BS produces signals related to the number of x-rays detected in the antinodes of the Talbot fringes, and that signal passes through a connector 291-B to a data processing system 295 for analysis.

In this manner, both bright field and dark field information are gathered in parallel, without the detectors blocking each other, as may be the case for the pair of detectors as was shown in FIG. 46.

4. Fabrication of Gratings

Fabrication of the gratings used in embodiments of the invention may be made using known prior art fabrication processes such as those previously described by Christian David [C. David et al., "Fabrication of diffraction gratings for hard x-ray phase contrast imaging", *Microelectron. Eng.* 84, 1172-1177, 2007].

Gratings for x-rays may be fabricated using silicon substrates, with etched changes in topography to induce phase changes and depositions of a higher Z material, such as gold (Au, Z=79), to induce absorption changes. The x-ray absorption properties for gold and silicon are illustrated in FIG. 39.

Figure 48:
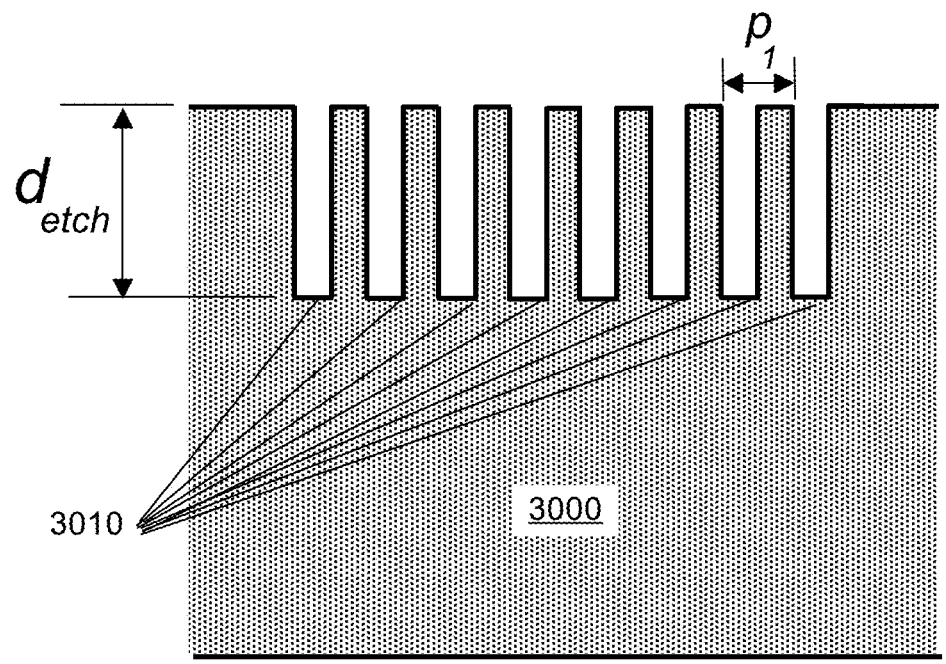
FIG. 48 illustrates a possible structure of an x-ray phase grating according to some embodiments of the invention.

As shown in FIG. 48, a periodic pattern 3010 may be etched into a silicon substrate 3000 to create a structure which introduces a periodic phase shift for x-rays falling at normal incidence. The phase shift depends on the etch depth, with a phase-shift of π radians for normal incidence x-rays achieved when the following condition is met:

$$d_{etch} = \frac{1}{2}\frac{\lambda}{|n-1|} = \frac{1}{2}\frac{\lambda}{\delta} \qquad [\text{Eqn. 25}]$$

Values for δ for silicon at several x-ray energies, along with the depth etched structures need to a phase-shift of π radians are shown in Table IV.

A typical grating fabrication process comprises coating a <110> oriented silicon wafer with a photoresist, and patterning the resist using conventional photolithography, focused ion beam lithography, or electron beam lithography. The silicon then undergoes an etching process such as wet etching in, for example, a potassium hydroxide (KOH) solution, or reactive ion etching (RIE), with the etching selectively occurring only for portions of the silicon not masked by the resist. The etch depth may be controlled by adjusting the time of the etch process. Other variations of the etching process will be known to those skilled in the art of semiconductor processing and manufacturing.

TABLE IV

Etch depth for Silicon phase shift of π radians.

| X-ray Energy (keV) | Wavelength λ (nm) | δ | π phase shift depth (μm) |
|---|---|---|---|
| 3.0 | 0.413 | 5.43E−05 | 3.81 |
| 5.0 | 0.248 | 1.98E−05 | 6.26 |
| 8.048 | 0.154 | 7.58E−06 | 10.17 |
| (Cu Kα) | | | |
| 10.0 | 0.124 | 4.89E−06 | 12.69 |
| 17.48 | 0.0709 | 1.59E−06 | 22.36 |
| (Mo Kα) | | | |
| 30.0 | 0.0413 | 5.36E−07 | 38.52 |
| 50.0 | 0.0248 | 1.93E−07 | 64.31 |
| 59.39 | 0.0209 | 1.37E−07 | 76.32 |
| (W Kα) | | | |
| 100.0 | 0.0124 | 4.82E−08 | 128.74 |

Figure 49:
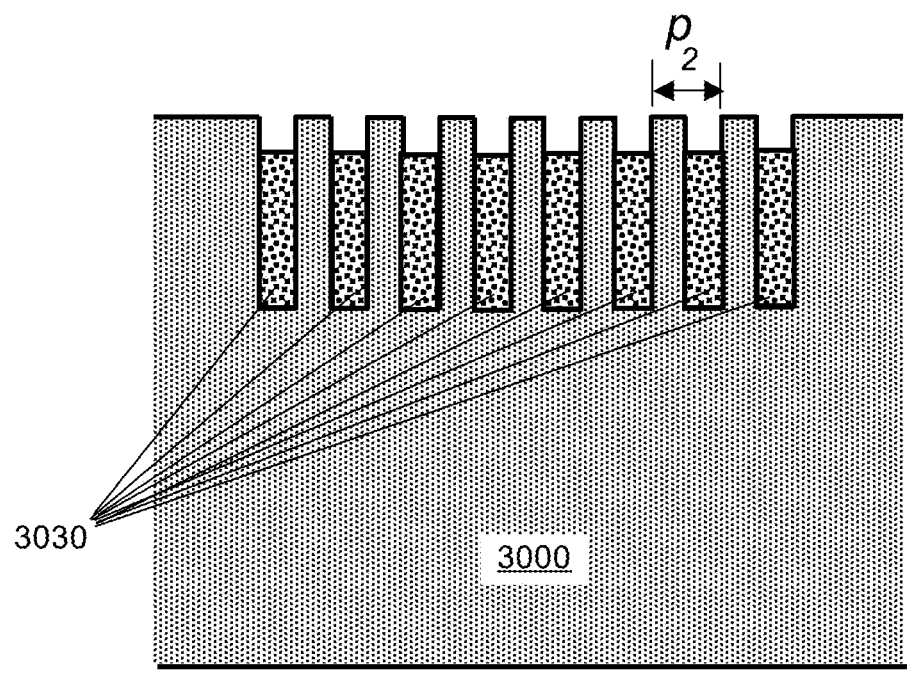
FIG. 49 illustrates a possible structure of an x-ray absorption grating according to some embodiments of the invention.

Absorption gratings such as those used for $G_2$ may be fabricated by initially creating a silicon phase grating, as described above, and then depositing an x-ray absorbing material, such as gold, into the grooves already patterned in the silicon. This is illustrated in FIG. 49, in which an amount of x-ray absorbing material 3030 such as gold has filled the grooves created in a silicon substrate 3000. One process for the deposition of gold into the silicon grooves involves a standard electroplating processes. To ensure that gold is only deposited into the grooves, a sacrificial layer of aluminum may initially be deposited at an angle, and a seed layer ~50 nm thick comprising Chromium (Cr) and gold (Au) are then deposited. A phosphoric acid treatment removes all the material deposited on the tops of the silicon structures, leaving seed material only in the bottom of the grooves in the silicon. Standard electroplating may follow, with growth of gold occurring only onto the deposited seed layers. Deposition of gold at hundreds of microns can create absorption gratings with a transmission modulation of 75% or more. Absorption will, however, depend on the x-ray energy and the absorption coefficient for the material, as was illustrated in FIGS. 1 and 39. Other methods for making x-ray absorption gratings will be known to those skilled in the art.

For some applications and for certain x-ray wavelengths, crystal gratings may also be used.

It should be noted that the antiscattering grids or gratings disclosed with these embodiments of the invention can be fabricated using any number of lithographic pattering techniques known to those skilled in the art as well.

5.0 Detector Properties

The detector may be any one of a number of detectors used to form x-ray images. One type of commonly used x-ray detector comprises a fluorescent screen or scintillator, such as one comprising a layer of cesium iodide (CsI), thallium doped CsI, yttrium aluminium garnet (YAG) or gadolinium sulfoxylate (GOS), that emits visible photons when exposed to x-rays. The visible photons are then detected by an electronic sensor that converts visible intensity into electronic signals, often with the additional formation of a relay image using visible optics that enlarge and magnify the intensity pattern of the photons emitted by the fluorescent screen. With the relay optics, the electronic detector need not comprise a high resolution sensor itself, and inexpensive commercial CCD detectors or complementary metal-oxide-semiconductor (CMOS) sensor arrays with, for example, 1024×1024 pixels, each 24 μm×24 μm square, may be used.

Commercial flat panel digital x-ray sensors in which a layer of scintillator material is placed in close proximity to (or even coated onto) an array of conventional optical image sensors are manufactured by, for example, Varian Inc. of Palo Alto, Calif. and General Electric, Inc. of Billerica, Mass. Other configurations of image sensors may be known to those skilled in the art. In embodiments in which a G2 analyzer grating is used, it is preferable to use highly efficient, fast read-out detectors such as flat panel detectors, used for medical and industrial uses. For many applications, using a flat panel detector with a resolution larger than 20 microns will require that an analyzer grating $G_2$ with a period equal to the Talbot fringe period be placed in the x-ray beam path before the detector.

A second approach is to use an electronic sensor that directly creates an electrical signal in response to the absorption of x-rays, by, for example, the creation of direct electron-hole pairs in amorphous selenium (a-Se). These are then converted into electronic signals using an array of thin-film transistors (TFTs). Such direct flat panel detectors (FPDs) such as the Safire FPD of Shimadzu Corp. of Kyoto, Japan, are commercially available.

6.0. Variations

Embodiments may further comprise other components typically included in Talbot interferometer, including spectral filters to obtain a desired x-ray energy bandwidth and positioning control systems for all the various components of the system.

It should be noted that certain terms used within this disclosure will be well known to those skilled in the art, such as grids or gratings. In the descriptions here, grids and gratings are terms that may be used interchangeably, and are not meant to be restrictive to a particular grid, period, or pattern.

Likewise, it should be noted that certain terms used within this disclosure will be well known to those skilled in the art, such as Talbot fringes, interference patterns, or "carpets". In the descriptions here, interference patterns, fringes, or "carpets" are terms that may be used interchangeably, and are not meant to be restrictive to any particular intensity pattern.

Likewise, it should be noted that certain terms used within this disclosure will be well known to those skilled in the art, such as septa for the absorbing structures of antiscattering grids. In the descriptions here, septa or septum or structure are terms that may be used interchangeably in reference to the absorbing structures of the antiscattering grid, and are not meant to be restrictive to any particular ratio of height to width, or to imply a solely one-dimensional geometry.

With this application, several embodiments of the invention, including the best mode contemplated by the inventors, have been disclosed. It will be recognized that, while specific embodiments may be presented, elements discussed in detail only for some embodiments may also be applied to others.

While specific materials, designs, configurations and fabrication steps have been set forth to describe this invention and the preferred embodiments, such descriptions are not intended to be limiting. Modifications and changes may be apparent to those skilled in the art, and it is intended that this invention be limited only by the scope of the appended claims.

We claim:

1. An x-ray transmission imaging system comprising:
   a source of x-rays comprising:
      a vacuum chamber;
      an emitter for an electron beam; and
      an electron target comprising:
         a substrate comprising a first material and, embedded in the substrate,
         at least a plurality of discrete structures comprising a second material selected for its x-ray generating properties,
         and in which said plurality of discrete structures; are arranged within a periodic pattern of sub-sources;
   a stage to position and orient an object to be examined;
   an x-ray detector comprising a two-dimensional array of x-ray detecting elements, positioned to detect x-rays transmitted through the object to be examined;
   said x-ray transmission system additionally comprising:
   a scattering rejection apparatus placed between the position of the object to be examined and the detector, comprising:
      a beam-splitting x-ray grating comprising periodic structures that form an x-ray phase-shifting grating positioned to diffract x-rays generated by the sub-sources of x-rays so that a Talbot interference pattern is formed by the interaction of the x-rays generated by the source of x-rays with the beam splitting grating; and
   an antiscattering grid having a periodic array of septa comprising an x-ray absorbing material positioned between the beam splitting x-ray grating and the detector; and
   a controller for adjusting the position of the anti-scattering grid relative to the Talbot interference pattern;
   in which the dimensions and periodicity of the septa of the antiscattering grid are selected to correspond to the dimensions of the Talbot interference pattern, and the septa of the antiscattering grid are positioned such that the septa are aligned with the nodes of the Talbot interference pattern.

2. The x-ray transmission imaging system of claim 1, in which
   the x-ray phase shifting grating comprises structures to introduce a phase-shift of approximately $\pi$ radians for a predetermined x-ray wavelength.

3. The x-ray transmission imaging system of claim 1, in which
   the x-ray phase shifting grating comprises structures to introduce a phase-shift of approximately $\pi/2$ radians for a predetermined x-ray wavelength.

4. The x-ray transmission imaging system of claim 1, in which
   the periodic structures of the x-ray phase-shifting grating have a period $p_1$ related to a dimension a for at least one of the discrete structures of the x-ray target by:

$$p_1 < \frac{\lambda L}{a}$$

where $\lambda$ is a predetermined x-ray wavelength,
   and L is the distance between the target and the beam-splitting x-ray grating.

5. The x-ray transmission imaging system of claim 1, in which the septa of the antiscattering grid comprise
   a high Z material selected from the group consisting of: tin, platinum, gold, tungsten, tantalum, molybdenum, nickel, lead, copper and gadolinium.

6. The x-ray transmission imaging system of claim 1, in which
   the antiscattering grid additionally comprises a substrate comprising an x-ray transparent material.

7. The x-ray transmission imaging system of claim 1, in which
   one or more of the septa have a height that is greater than 5 times the width of the gap between said one or more of the septa and its neighboring septa.

8. The x-ray transmission imaging system of claim 1, in which
   the period of the septa of the antiscattering grid is an integer multiple of the lateral period of the Talbot interference pattern.

9. The x-ray transmission imaging system of claim 1, additionally comprising:
   a second antiscattering grid comprising an x-ray absorbing material positioned between the first antiscattering grid and the detector.

10. The x-ray transmission imaging system of claim 1, in which the contrast of the Talbot interference pattern is greater than 20%.

11. The x-ray transmission imaging system of claim 1, in which
the plurality of discrete structures are arranged in a two-dimensional periodic pattern of sub-sources.

12. The x-ray transmission imaging system of claim 11, in which
the two-dimensional periodic pattern of sub-sources comprises a mesh pattern.

13. The x-ray transmission imaging system of claim 11, in which
the two-dimensional periodic pattern of sub-sources comprises a checkerboard.

14. The x-ray transmission imaging system of claim 11, in which
the x-ray phase shifting grating comprises a two-dimensional periodic pattern of phase-shifting structures.

15. The x-ray transmission imaging system of claim 1, additionally comprising:
an analyzer grating having periodic structures of x-ray absorbing material positioned between the antiscattering grid and the detector.

16. The x-ray transmission imaging system of claim 1, in which
the Talbot interference pattern comprises diverging interference fringes.

* * * * *